US006972324B2

(12) United States Patent
Adolf et al.

(10) Patent No.: US 6,972,324 B2
(45) Date of Patent: Dec. 6, 2005

(54) ANTIBODIES SPECIFIC FOR CD44V6

(75) Inventors: Günther Adolf, Vienna (AT); Elinborg Ostermann, Vienna (AT); Erik Patzelt, Purkersdorf (AT); Marlies Sproll, Gauting (DE); Karl-Heinz Heider, Stockerau (AT); John J. Miglietta, Bethel, CT (US); Augustinus Antonius Maria Silvester Van Dongen, Utrecht (NL)

(73) Assignees: Boehringer Ingelheim Pharmaceuticals, Inc., Ridgefield, CT (US); Boehringer Ingelheim International, GmbH, Ingelheim am Rhein (DE)

(*) Notice: Subject to any disclaimer, the term of this patent is extended or adjusted under 35 U.S.C. 154(b) by 23 days.

(21) Appl. No.: 10/147,849

(22) Filed: May 20, 2002

(65) Prior Publication Data

US 2003/0190319 A1 Oct. 9, 2003

Related U.S. Application Data

(60) Provisional application No. 60/323,075, filed on Sep. 19, 2001, and provisional application No. 60/325,147, filed on Sep. 26, 2001.

(30) Foreign Application Priority Data

May 18, 2001 (EP) .............................................. 01112237

(51) Int. Cl.$^7$ .............................................. C07K 16/00
(52) U.S. Cl. .............................. 530/388.85; 530/387.3; 530/391.3; 424/133.1; 424/156.1
(58) Field of Search .......................... 530/391.3, 387.1, 530/387.3, 388.85; 424/130, 133.1, 156.1, 155.1

(56) References Cited

U.S. PATENT DOCUMENTS

| 4,897,255 | A | 1/1990 | Fritzberg et al. |
| 5,082,930 | A | 1/1992 | Nicolotti et al. |
| 5,242,679 | A | 9/1993 | Fritzberg et al. |
| 5,616,468 | A | 4/1997 | Salmi et al. |
| 5,648,267 | A | 7/1997 | Reff |
| 5,681,927 | A | 10/1997 | Fritzberg et al. |
| 5,733,779 | A | 3/1998 | Reff |
| 5,916,561 | A | 6/1999 | Adolf et al. |
| 6,010,865 | A | 1/2000 | Ponta et al. |
| 6,338,835 | B1 * | 1/2002 | Shochat et al. |

FOREIGN PATENT DOCUMENTS

| AU | 726704 | 6/1997 |
| CA | 2281934 | 9/1998 |
| EP | 0 188 256 B1 | 7/1986 |
| EP | 0 239 400 A2 | 9/1987 |
| EP | 0 247 866 B1 | 12/1987 |
| EP | 0 284 071 B1 | 9/1988 |
| EP | 0284071 * | 9/1988 |
| EP | 0 368 684 A1 | 5/1990 |
| EP | 0 438 310 A1 | 7/1991 |
| EP | 0 481 790 A2 | 4/1992 |
| WO | WO 87/02671 A1 | 5/1987 |
| WO | WO 90/07861 A1 | 7/1990 |
| WO | WO 92/05274 A1 | 4/1992 |
| WO | WO 92/07075 A1 | 4/1992 |
| WO | WO 92/11018 A1 | 7/1992 |
| WO | WO 92/22653 A1 | 12/1992 |
| WO | WO 93/05804 A1 | 4/1993 |
| WO | WO 94/11523 A2 | 5/1994 |
| WO | WO 94/12631 A1 | 6/1994 |
| WO | WO 95/00851 A1 | 1/1995 |
| WO | WO 95/33771 A1 | 12/1995 |
| WO | WO 97/09351 A1 | 3/1997 |
| WO | WO 97/21104 A1 | 6/1997 |
| WO | WO 98/39034 A2 | 9/1998 |

OTHER PUBLICATIONS

Fundamental Immunology 242 (William E. Paul, M.D. ed., 3d ed. 1993).*
Rudikoff et al., PNAS 79:1979, 1982.*
Rieger et al., Glossary of Genetics of Cytogenetics, Classical and Molecular, 4th Ed., Springer–Verlay, Berlin, 1976.*
Boulianne, G.L., et al., "Production of functional chimaeric mouse/human antibody," Nature 312:643–646, Macmillan Publishers, Ltd. (1984).
Chothia, C., and Lesk, A.M., "Canonical Structures for the Hypervariable Regions of Immunoglobulins," J. Mol. Biol. 196:901–917, Academic Press, Ltd. (1987).
Günthert, U., et al., "A New Variant of Glycoprotein CD44 Confers Metastatic Potential to Rat Carcinoma Cells," Cell 65:13–24, Cell Press (1991).
Haisma, H.J., et al., "Iodination of Monoclonal Antibodies for Diagnosis and Radiotherapy Using a Convenient One Vial Method," J. Nucl. Med. 27:1890–1895, The Society of Nuclear Medicine, Inc. (1986).
Hayden, M.A., and Mandecki, W., "Laboratory Methods. Gene Synthesis by Serial Cloning of Oligonucleotides," DNA 7:571–577, Mary Ann Liebert, Inc. (1988).
Heider, K.–H., et al., "A Human Homologue of the Rat Metastasis–associated Variant of CD44 is Expressed in Colorectal Carcinomas and Adenomatous Polyps," J. Cell. Biol. 120:227–233, Rockefeller University Press (1993).
Heider, K.–H., et al., "Differential Expression of CD44 Splice Variants in Intestinal– and Diffuse–Type Human Gastric Carcinomas and Normal Gastric Mucosa," Cancer Res. 53:4197–4203, American Association for Cancer Research (1993).

(Continued)

Primary Examiner—Larry R. Helms
(74) Attorney, Agent, or Firm—Sterne, Kessler, Goldstein & Fox PLLC

(57) ABSTRACT

The present invention belongs to the field of oncology. The invention relates to antibodies with specified sequence which are specific for an epitope which is coded by the variant exon v6 of the CD44 gene and to derivatives of said antibody. The invention also provides nucleic acid molecules encoding said antibody proteins. The invention furthermore pertains to methods for producing said antibody proteins. The invention also provides pharmaceutical compositions comprising said antibody proteins. The invention furthermore is concerned with the use in the manufacture of a medicament for the treatment of cancer.

68 Claims, 5 Drawing Sheets

OTHER PUBLICATIONS

Heider, K.-H., et al., "Splice Variants of the Cell Surface Glycoprotein CD44 Associated with Metastatic Tumour Cells are Expressed in Normal Tissues of Humans and Cynomolgus Monkeys," *Eur. J. Cancer* 31A:2385–2391, Elsevier Science, Ltd. (1995).

Heider, K.-H., et al., "Characterization of a high–affinity monoclonal antibody specific for CD44v6 as candidate for immunotherapy of squamous cell carcinomas," *Cancer Immunol. Immunother.* 43:245–253, Springer–Verlag (1996).

Himmler, A., et al., "Molecular Cloning and Expression of Human and Rat Tumor Necrosis Factor Receptor Chain (p60) and Its Soluble Derivative, Tumor Necrosis Factor–Binding Protein," *DNA Cell Biol.* 9:705–715, Mary Ann Liebert, Inc. (1990).

Hofmann, M., et al., "CD44 Splice Variants Confer Metastatic Behavior in Rats: Homologous Sequences Are Expressed in Human Tumor Cell Lines," *Cancer Res.* 51:5292–5297, American Association for Cancer Research (1991).

Huston, J.S., et al., "Protein engineering of antibody binding sites: Recovery of specific activity in an anti–digoxin single–chain FV analogue produced in *Escherichia coli*," *Proc. Natl. Acad. Sci. USA* 16:5879–5883, National Academy Press (1988).

Hu, Shi–zhen, et al., "Minibody: A Novel Engineered Anti-Carcinoembryonic Antigen Antibody Fragment (Single–Chain Fv–$C_H3$) Which Exhibits Rapid, High–Level Targeting of Xenografts," *Cancer Res.* 56:3055–3061, American Association For Cancer Research (1996).

Koopman, G., et al., "Activated Human Lymphocytes and Aggressive Non–Hodgkin's Lymphomas Express a Homologue of the Rat Metastasis–associated Variant of CD44," *J. Exp. Med.* 177:897–904, Rockefeller University Press (1993).

Kortt, A.A., et al., "Single–chain Fv fragments of anti–neuraminidase antibody NC10 containing five– and ten–residue linkers form dimers and with zero–residue linker a trimer," *Protein Eng.* 10:423–433, Oxford University Press (1997).

Kugelman, L.C., et al., "The Core Protein of Epican, a Heparan Sulfate Proteoglycan on Keratinocytes, Is an Alternative Form of CD44," *J. Invest. Dermatol.* 99:887–891, Society for Investigative Dermatology, Inc. (1992).

LoBuglio, A.F., et al., "Mouse/human chimeric monoclonal antibody in man: Kinetics and immune response," *Proc. Natl. Acad. Sci. USA* 86:4220–4224, National Academy Press (1989).

Lovejoy, B., et al., "Crystal Structure of a Synthetic Triple–Stranded α–Helical Bundle," *Science* 259:1288–1293, American Association for the Advancement of Science (1993).

Pack, P., et al., "Improved Bivalent Miniantibodies, with Identical Avidity as Whole Antibodies, Produced by High Cell Density Fermentation of *Escherichia coli*," *Bio/technology* 11:1271–1277, Nature Publishing Company (1993).

Pack, P., et al., "Tetravalent Miniantibodies with High Avidity Assembling in *Escherichia coli*," *J. Mol. Biol.* 246:28–34, Academic Press, Ltd. (1995).

Perisic, O., et al., "Crystal structure of a diabody, a bivalent antibody fragment," *Structure* 2:1217–1226, Current Biology, Ltd. (1994).

Queen, C., et al., "A humanized antibody that binds to the interleukin 2 receptor," *Proc. Natl. Acad. Sci. USA* 66:10029–10033, National Academy Press (1989).

Riechmann, L., et al., "Reshaping human antibodies for therapy," *Nature* 332:323–327, Macmillan Publishers, Ltd. (1988).

Rudy, W., et al., "The Two Major CD44 Proteins Expressed on a Metastatic Rat Tumor Cell Line Are Derived from Different Splice Variants: Each One Individually Suffices to Confer Metastatic Behavior," *Cancer Res.* 53:1262–1268, American Association for Cancer Research (1993).

Screaton, G.R., et al., "Genomic structure of DNA encoding the lymphocyte homing receptor CD44 reveals at least 12 alternatively spliced exons," *Proc. Natl. Acad. Sci. USA* 89:12160–12164, National Academy Press (1992).

Seiter, S., et al., "Prevention of Tumor Metastasis Formation by Anti–Variant CD44," *J. Exp. Med.* 177:443–455, Rockefeller University Press (1993).

Sharkey, R.M., et al., "Rapid Blood Clearance of Immunoglobulin G2a and Immunoglobulin G2b in Nude mice," *Cancer Res.* 51:3102–310, American Association for Cancer Research (1991).

Stemmer, W.P.C., et al., "Single–step assembly of a gene and entire plasmid from large numbers of oligodeoxyribonucleotides," *Gene* 164:49–53, Elsevier Science B.V. (1995).

Stroomer, J.W.G., et al., "Safety and Biodistribution of $^{99m}$Technetium–labeled Anti–CD44v6 Monoclonal Antibody BIWA 1 in Head and Neck Cancer Patients," *Clin. Cancer Res.* 6:3046–3055, American Association for Cancer Research (Aug. 2000).

Tölg, C., et al., Splicing choice from ten variant exons establishes CD44 variability, *Nucleic Acids Res.* 21:1225–1229, Oxford University Press (1993).

Urlaub, G., and Chasin, L.A., "Isolation of Chinese hamster cell mutants deficient in dihydrofolate reductase activity," *Proc. Natl. Acad. Sci. USA* 77:4216–4220, National Academy Press (1980).

van Gog, F.B., et al., "High Dose Rhenium–186–Labeling of Monoclonal Antibodies for Clinical Application. Pitfalls and Solutions," *Cancer* 80(Suppl):2360–2370, John Wiley & Sons, Inc. (1997).

van Gog, F.B., et al., "Rapid elimination of mouse/human chimeric monoclonal antibodies in nude mice," *Cancer Immunol. Immunother.* 44:103–111, Springer–Verlag (1997).

Welt, S., et al., "Antibody Targeting in Metastatic Colon Cancer: A Phase I Study of Monoclonal Antibody F19 Against a Cell–Surface Protein of Reactive Tumor Stromal Fibroblasts," *J. Clin. Oncol.* 12:1193–1203, W.B. Saunders Company (1994).

Wielenga, V.J.M., et al., "Expression of CD44 Variant Proteins in Human Colorectal Cancer Is Related to Tumor Progression," *Cancer Res.* 53:4745–4756, American Association for Cancer Research (1993).

Ye, Q.-Z., et al., "Gene synthesis and expression in *E. coli* for pump, a human matrix metalloproteinase," *Biochem. Biophys. Res. Commun.* 186:143–149, Academic Press, Inc. (1992).

NCBI Entrez, GenBank Report, Accession No. S31669, from Cuisinier, A.M., et al. (1999).

NCBI Entrez, GenBank Report, Accession No. M29469, from Spatz, et al. (1995).

European Search Report for European Application No. EP 01 11 2237 mailed on Oct. 23, 2001.

International Search Report for International Application No. PCT/EP02/05467 mailed on Jul. 15, 2002.

* cited by examiner 1170.1 Part A  AUC Proportionality Assessment

ANTIBODIES SPECIFIC FOR CD44V6

CROSS REFERENCE TO RELATED APPLICATIONS

The present application claims the benefit of the filing date of U.S. Appl. No. 60/323,075, filed Sep. 19, 2001 and U.S. Appl. No. 60/325,147, filed Sep. 26, 2001. The contents of the aforesaid applications are relied upon and incorporated by reference in their entirety.

BACKGROUND OF THE INVENTION

1. Field of the Invention

The present invention belongs to the field of oncology. The invention relates to antibodies with specified sequence which are specific for an epitope which is coded by the variant exon v6 of the CD44 gene and to derivatives of said antibody. The invention also provides nucleic acid molecules encoding said antibody proteins. The invention furthermore pertains to methods for producing said antibody proteins. The invention also provides pharmaceutical compositions comprising said antibody proteins. The invention furthermore is concerned with the use in the manufacture of a medicament for the treatment of cancer.

2. Background Art

Recently it has been shown that the expression of variants of the surface glycoprotein CD44 is necessary and sufficient for causing so-called spontaneous metastatic behaviour of a non-metastasizing rat pancreatic adenocarcinoma cell line as well as a non-metastasizing rat fibrosarcoma cell line (Günthert et al., 1991). While the smallest CD44 isoform, the standard form CD44s (or CD44std), is ubiquitary expressed in different tissues including epithelial cells, certain CD44 splice variants (CD44v, CD44var) are expressed only on a subset of epithelial cells. The CD44 variants are generated by alternative splicing in a way that the sequences of ten exons (v1–v10) are completely excised in CD44s but can appear in the bigger variants in different combinations (Screaton et al., 1992; Tölg et al., 1993; Hofmann et al., 1991). The variants differ in that different amino acid sequences are inserted at a certain site of the extracellular part of the protein. Such variants can be detected in various human tumor cells as well as in human tumor tissue. So, the expression of CD44 variants in the course of colorectal carcinogenesis has recently been investigated (Heider et al., 1993a). The expression of CD44 variants is absent in normal human colon epithelium, and only a weak expression is detectable in the proliferating cells of the crypts. In later stages of the tumor progression, e.g. in adenocarcinomas, all malignancies express variants of CD44. Tissue expression of variant CD44 on a high level has also been shown in aggressive Non-Hodgkin lymphomas (Koopman et al., 1993).

Exon v6 appears to play a special role especially in the course of metastatic spread (Rudy et al., 1993). In an animal model, antibodies against v6 specific epitopes could prevent the settlement of metastatic cells and the growth of metastases (Seiter et al., 1993). In colon carcinomas, v6 expression correlates with tumor progression (Wielenga et al., 1993). In gastric carcinomas, v6 expression is an important diagnostic marker to distinguish tumors of the intestinal type from those of the diffuse type (Heider et al., 1993b). In the latter two publications, v6 expression has been determined using antibodies against v6 specific epitopes.

As CD44v6 has been shown to be a tumor-associated antigen with a favorable expression pattern in human tumors and normal tissues (Heider et al., 1995; Heider et al., 1996), it has been subject to antibody-based diagnostic and therapeutic approaches, (Heider et al., 1996; WO 95/33771; WO 97/21104).

One serious problem that arises when using non-human antibodies for applications in humans is that they quickly raise a human anti-non-human response that reduces the efficacy of the antibody in patients and impairs continued administration. To overcome that probem, concepts of "humanising" non-human antibodies have been developed in the art. In the first approach, humanization of non-human antibodies has been tried to achieve by constructing non-human/human chimeric antibodies, wherein the non-human variable regions are joined to human constant regions (Boulianne G. L., Hozumi N. and Shulman, M. J. (1984) Production of functional chimeric mouse/human antibody *Nature* 312: 643) The chimeric antibodies thus generated retain the binding specificity and affinity of the original non-human antibody. However, chimeric antibodies, although significantly better than mouse antibodies, can still elicit an anti-chimeric response in humans (LoBuglio A. F., Wheeler R. H., Trang J., Haynes A., Rogers K., Harvey E. B., Sun L., Ghrayeb J. and Khazaeli M. B. (1989) Mouse/human chimeric monoclonal antibody in man: Kinetics and immune response. *Proc. Natl. Acad. Sci.* 86: 4220). This approach was later refined by further reducing the amount of non-human sequences by grafting the complementarity determining regions (CDRs) from the non-human variable regions to human variable regions and then joining these "reshaped human" variable regions to human constant regions (Riechmann L., Clark M., Waldmann H. and Winter G. (1988) Reshaping human antibodies for therapy. *Nature* 332: 323). CDR-grafted or reshaped human antibodies contain little or no protein sequences that can be identified as being derived from mouse antibodies. Although an antibody humanised by CDR-grafting may still be able to elicit some immune reactions, such as an anti-allotype or an anti-idiotypic response, as seen even with natural human antibodies, the CDR-grafted antibody will be significantly less immunogenic than a mouse antibody thus enabling a more prolonged treatment of patients.

However, it soon turned out that CDR-grafting alone did not result in antibodies with sufficient binding affinity. CDR-grafted antibodies have relatively poor binding characteristics as compared to their parent non-human antibodies because more amino acids than those within the CDR's are involved in antigen binding. In consequence, CDR-grafted antibodies with poor binding affinity are not regarded to be useful in therapy. Therefore, attempts have been made to create antibodies which combine the low immunogenicity of CDR-grafted antibodies with the good binding characteristics of the non-human parent antibodies. The concept was developed that, in addition to CDR-grafting, one to several amino acids in the humanized framework region have to be retained as residues of rodent donor origin for retaining binding affinity (Queen et al, (1989)*Proc. Natl. Acad. Sci.* 86: 10029–10033).

Because of the high potential utility such antibodies could have in diagnosis and therapy, there is a need of antibodies with improved properties which are suitable for treatment of human cancer.

The problem underlying the present invention was to provide an antibody with significantly better properties as compared to the known CD44v6 specific antibodies.

SUMMARY OF THE INVENTION

The above-captioned technical problem is solved by the embodiments characterized in the claims and the description. The before-mentioned disadvantages in the art are overcome by the claims and the description of the present invention.

In order to solve the problems mentioned above, the present inventors have designed and generated a CD44v6 specific humanised antibody called BIWA8, which was both CDR-grafted and framework-mutated and had low immunogenicity combined with high affinity.

However, the inventors were able to create an antibody with even superior therapeutic utility, called BIWA4. Albeit this one has less binding affinity as compared to BIWA8, it surprisingly shows a much more favorable biodistribution and tumor uptake when administered in vivo.

The present invention belongs to the field of oncology. The invention relates to antibodies with specified sequence which are specific for an epitope which is coded by the variant exon v6 of the CD44 gene and to derivatives of said antibody. The invention also provides nucleic acid molecules encoding said antibody proteins. The invention furthermore pertains to methods for producing said antibody proteins. The invention also provides pharmaceutical compositions comprising said antibody proteins. The invention furthermore is concerned with the use in the manufacture of a medicament for the treatment of cancer.

IC50: concentrations of cMAb and hMAbs at which binding of mMAb BIWA 1 to attached A431 cells is reduced by 50%. IC50 values relative to BIWA 2 are indicated.

Figure 2:
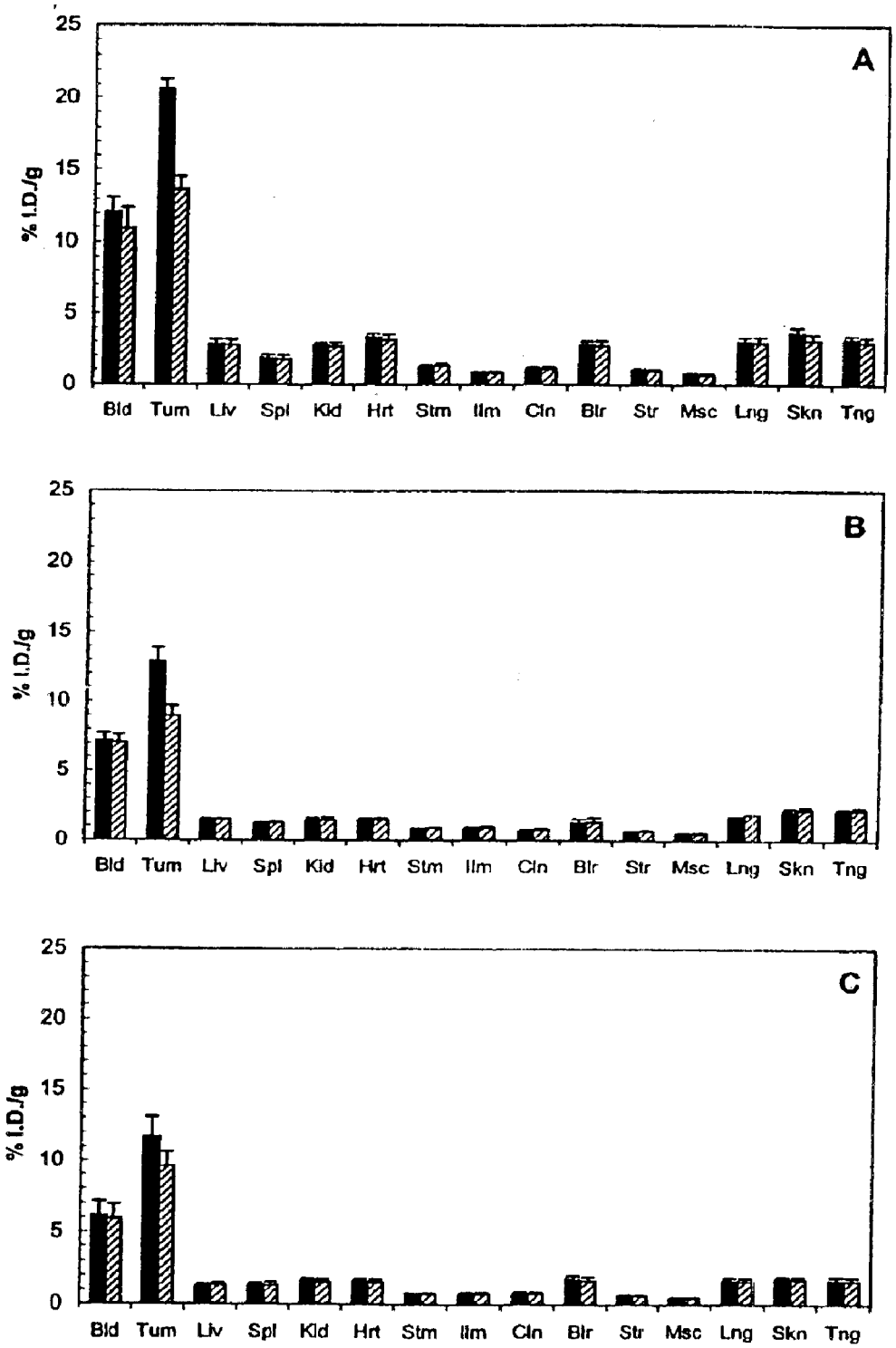

FIG. 2. Biodistributions of co-injected $^{125}$I- and $^{131}$I-labeled CD44v6-specific MAbs (10 µCi, 50 µg) in HNX-OE xenograft-bearing mice at 3 or 4 days p.i. Three groups of mice received either (A) $^{131}$I-U36 (black bars) and $^{125}$I-BIWA 1 (hatched bars) (n=5), (B) $^{131}$I-BIWA 4 (black bars) and 125I-BIWA 2 (hatched bars) (n=6) or (C) $^{131}$I-BIWA 4 (black bars) and $^{125}$I-BIWA 8 (hatched bars) (n=6). At 3 (A) or 4 days (B,C) after injection mice were bled, sacrificed, dissected and the radioactivity levels (% ID/g±s.e.m.) of tumor, blood and several organs were assessed. (Bld: blood, Tum: tumor, Liv: liver, Spl: spleen, Kid: kidney, Hrt: heart, Stm: stomach, Ilm: ileum, Cln: colon, Blr: bladder, Str: sternum, Msc: muscle, Lng: lung, Skn: skin, Tng: tongue).

Figure 3:
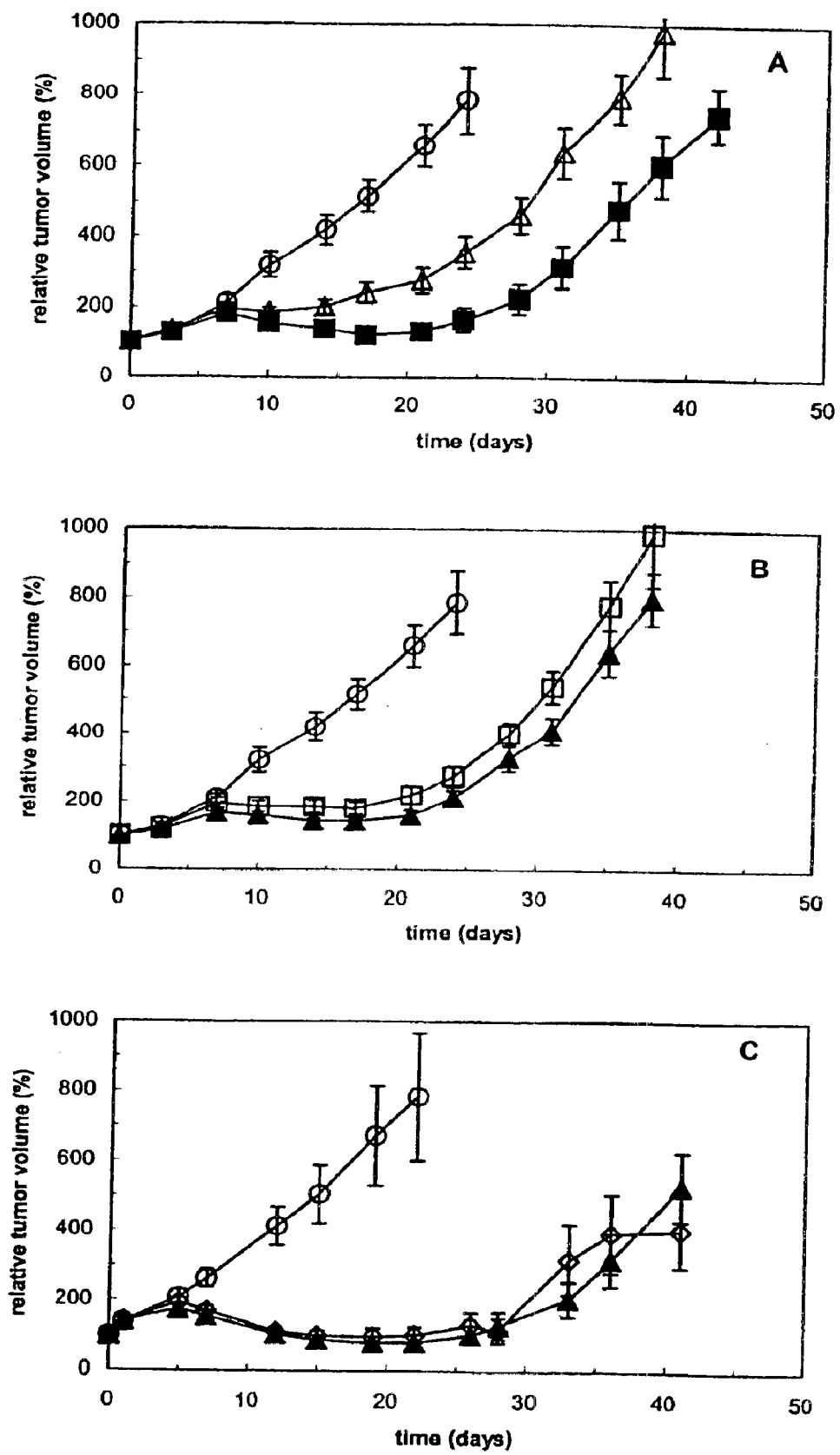

FIG. 3. Therapeutic efficacy of $^{186}$Re-labeled CD44v6-specific MAbs in HNX-OE xenograft-bearing nude mice. Mice received 300 µCi 186Re-U36 (-●-, FIG. A), 300 µCi $^{186}$Re-BIWA 1 (-▲-, FIG. A), 300 µCi $^{186}$Re-BIWA 4 (-✖-, FIG. B), 300 µCi $^{186}$Re-BIWA 2 (-♦-, FIG. B), 400 µCi $^{186}$Re-BIWA 4 (✖-, FIG. C), 400 µCi $^{186}$Re-BIWA 8 (-❈-, FIG. C), or saline (-✱-, FIGS. A, B, C) as control. Control groups in FIG. A and B are the same. The tumor size is expressed as the average tumor volume (±s.e.m.) during treatment relative to the average tumor volume at the start of therapy.

Figure 4:
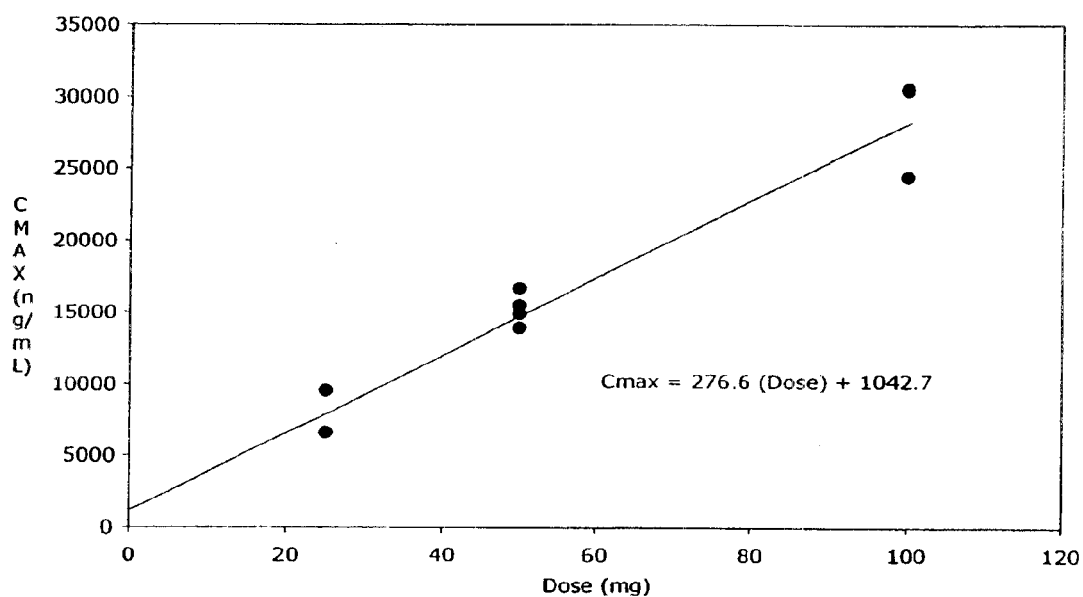

FIG. 4. Relationship between MAb dose administered and the AUC observed following BIWA 4 intravenous infusion to 10 patients in Part A of the study.

Figure 5:
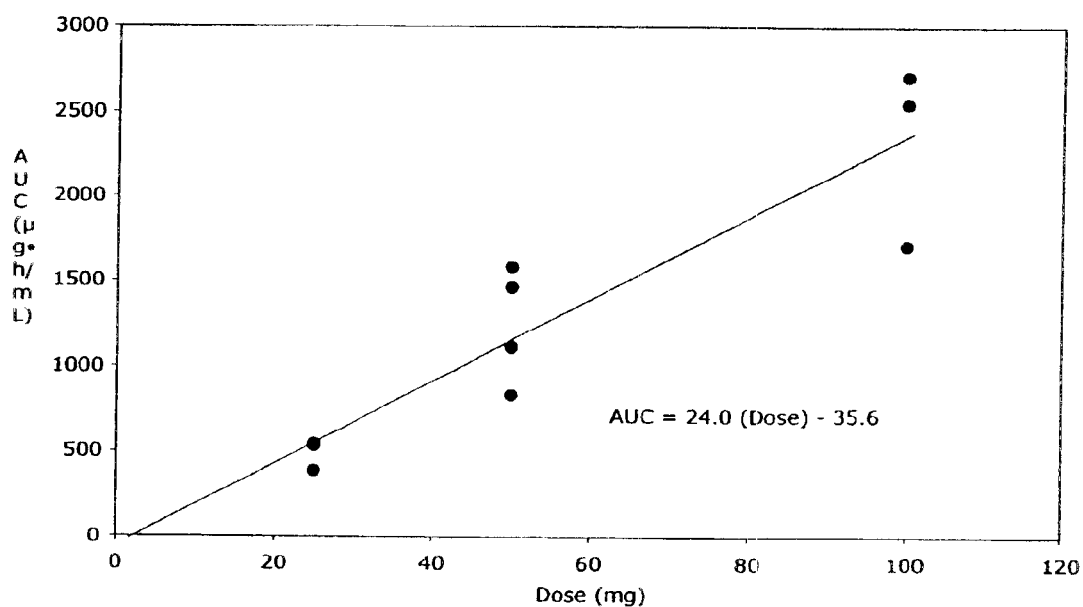

FIG. 5. Relationship between MAb dose administered and the maximum plasma BIWA 4 concentration observed following BIWA 4 intravenous infusion to 10 patients in Part A of the study.

DISCLOSURE OF THE PREFERRED EMBODIMENTS OF THE INVENTION

Before the embodiments of the present invention it must be noted that as used herein and in the appended claims, the singular forms "a", "an", and "the" include plural reference unless the context clearly dictates otherwise. Thus, for example, reference to "an antibody" includes a plurality of such antibodies, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

The terms "antibody molecule" or "antibody protein" or "antibody" as used herein shall be considered equivalent.

"Complementarity determining regions of a monoclonal antibody" are understood to be those amino acid sequences involved in specific antigen binding according to Kabat (Kabat E. A., Wu T. T., Perry H. M., Gottesman K. S. and Foeller C. (1991) *Sequences of Proteins of Immunological Interest* (5th Ed.). NIH Publication No. 91-3242. U.S. Department of Health and Human Services, Public Health Service, National Institutes of Health, Bethesda, Md.) in connection with Chothia and Lesk (Chothia and Lesk (1987) *J. Mol. Biol.* 196:901–917).

As used herein, the term "framework modifications" refers to the exchange, deletion or addition of single or multiple amino acids in the variable regions surrounding the individual complementarity determining regions. Framework modifications may have an impact on the immunogenicity, producibility or binding specificity of an antibody protein.

The present invention provides an antibody molecule comprising a variable region of the heavy chain as characterized by the amino acid sequence as defined in SEQ ID NO:1 or a fragment, allelic variant, functional variant, glycosylation variant, fusion molecule or a chemical derivative thereof. Both antibodies BIWA4 and BIWA 8 comprise the variable region of the heavy chain as characterized in amino acid sequence SEQ ID NO:1.

A "fragment" according to the invention is a shorter antibody molecule, i.e. any polypeptide subset, characterized in that it is encoded by a shorter nucleic acid molecule than disclosed below, however still retains its antibody binding activity.

"A functional variant" of the antibody molecule according to the invention is an antibody molecule which possesses a biological activity (either functional or structural) that is substantially similar to the antibody molecule according to the invention, i.e. a substantially similar substrate specificity or cleavage of the substrate. The term "functional variant" also includes "a fragment", "an allelic variant" "a functional variant", "variant based on the degenerative nucleic acid code" or "chemical derivatives". Such a "functional variant" e.g. may carry one or several point mutations, one or several nucleic acid exchanges, deletions or insertions or one or several amino acid exchanges, deletions or insertions. Said functional variant is still retaining its biological activity such as antibody binding activity, at least in part or even going along with an improvement said biological activity.

A "functional variant" of the antibody molecule according to the invention is a antibody molecule which possesses a biological activity (either functional or structural) that is substantially similar to the antibody molecule according to the invention, i.e. a substantially similar target molecule binding activity. The term "functional variant" also includes "a fragment", "an allelic variant" "a functional variant", "variant based on the degenerative nucleic acid code" or "chemical derivatives".

An "allelic variant" is a variant due to the allelic variation, e.g. differences in the two alleles in humans. Said variant is still retaining its biological activity such as antibody target binding activity, at least in part or even going along with an improvement said biological activity.

A "variant based on the degenerative of the genetic code" is a variant due to the fact that a certain amino acid may be encoded by several different nucleotide triplets. Said variant is still retaining its biological activity such as antibody binding activity, at least in part or even going along with an improvement said biological activity.

A "fusion molecule" may be the antibody molecule according to the invention fused to e.g. a reporter such as a radiolabel, a chemical molecule such as a toxin or a fluorescent label or any other molecule known in the art.

As used herein, a "chemical derivative" according to the invention is an antibody molecule according to the invention chemically modified or containing additional chemical moieties not normally being part of the molecule. Such moieties may improve the molecule's activity such as target destruction (e.g. killing of tumor cells) or may improve its solubility, absorption, biological half life etc.

A molecule is "substantially similar" to another molecule if both molecules have substantially similar structures or biological activity. Thus, provided that two molecules possess a similar activity, they are considered variants as that term is used herein even if the structure of one of the molecules is not found in the other, or if the sequence of amino acid residues is not identical.

For many uses of the antibodies according to the invention it is desirable to have the smallest possible antigen-binding, i.e. CD44v6-binding units. Therefore in another preferred embodiment an antibody protein according to the invention is a Fab fragment (Fragment antigen-binding= Fab). These CD44v6-specific antibody proteins according to the invention consist of the variable regions of both chains which are held together by the adjacent constant region. These may be formed by protease digestion, e.g. with papain, from conventional antibodies, but similar Fab fragments may also be produced in the mean time by genetic engineering. In another preferred embodiment an antibody protein according to the invention is an F(ab')2 fragment, which may be prepared by proteolytic cleaving with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). In another preferred embodiment an CD44v6-specific antibody molecule according to the invention is such an Fv fragment. Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind known from the prior art are described in Huston et al. (1988, PNAS 16: 5879–5883). Therefore, in another preferred embodiment an CD44v6-specific antibody protein according to the invention is a single-chain-Fv protein (scFv).

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. di-, tri- and pentabodies). Therefore in another preferred embodiment an antibody protein according to the invention is an CD44v6-specific diabody antibody fragment. By diabody the skilled person means a bivalent homodimeric scFv derivative (Hu et al., 1996, PNAS 16: 5879–5883). The shortening of the Linker in an scFv molecule to 5–10 amino acids leads to the formation of homodimers in which an inter-chain VH/NL-superimposition takes place. Diabodies may additionally be stabilised by the incorporation of disulphide bridges. Examples of diabody-antibody proteins from the prior art can be found in Perisic et al. (1994, Structure 2: 1217–1226).

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. The disulphide bridges in the Hinge region are mostly formed in higher cells and not in prokaryotes. In another preferred embodiment an antibody protein according to the invention is an CD44v6-specific minibody antibody fragment. Examples of minibody-antibody proteins from the prior art can be found in Hu et al. (1996, Cancer Res. 56: 3055–61).

By triabody the skilled person means a: trivalent homotrimeric scFv nderivative (Kortt et al. 1997 Protein Engineering 10: 423–433). ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures (Pack et al., 1993 Biotechnology II:, 1271–1277; Lovejoy et al. 1993 Science 259: 1288–1293; Pack et al., 1995 J. Mol. Biol. 246: 28–34).

Therefore in a preferred embodiment an antibody protein according to the invention is an CD44v6-specific multimerised molecule based on the abovementioned antibody fragments and may be, for example, a triabody, a tetravalent miniantibody or a pentabody.

In a more preferred embodiment, the invention relates to an antibody molecule wherein the variable region of the heavy chain consists of the amino acids as characterized by the amino acid sequence of SEQ ID NO:1.

In another preferred embodiment, the invention relates to an antibody molecule comprising a variable region of the light chain as characterized by the amino acid sequence as defined in SEQ ID NO:2 or a fragment, allelic variant, functional variant, glycosylation variant, fusion molecule or a chemical derivative thereof. Antibody BIWA4 as used herein comprises the variable region of the light chain as defined in amino acid sequence SEQ ID NO:2.

In another more preferred embodiment, the invention relates to an antibody molecule wherein the variable region of the light chain consists of the amino acids as characterized by the amino acid sequence of SEQ ID NO:2.

In another preferred embodiment, the invention relates to an antibody molecule comprising a variable region of the light chain as characterized by the amino acid sequence as defined in SEQ ID NO:3 or a fragment, allelic variant, functional variant, glycosylation variant, fusion molecule or a chemical derivative thereof. Antibody BIWA 8 comprises the variable region of the light chain as characterized in amino acid sequence SEQ ID NO:3.

In another more preferred embodiment, the invention relates to an antibody molecule wherein the variable region of the light chain consists of the amino acids as characterized by the amino acid sequence of SEQ ID NO:3.

In another more preferred embodiment, the invention relates to an antibody molecule according to the invention comprising a variable region of the heavy chain as characterized by the amino acid sequence as defined in SEQ ID NO:1 and comprising a variable region of light chain as characterized by the amino acid sequence as defined in SEQ ID NO:2 or a fragment, allelic variant, functional variant, glycosylation variant, fusion molecule or a chemical derivative thereof. Antibody BIWA4 comprises the variable region of the heavy chain as characterized in amino acid sequence SEQ ID NO:1 and variable region of the light chain as defined in amino acid sequence SEQ ID NO:2.

In a most preferred embodiment, the invention relates to an antibody molecule according to the invention wherein the variable region of the heavy chain consists of the amino acids as characterized by the amino acid sequence of SEQ ID NO:1 and wherein the variable region of the light chain consists of the amino acids as characterized by the amino acid sequence of SEQ ID NO:2.

In another more preferred embodiment, the invention relates to an antibody molecule according to the invention comprising a variable region of the heavy chain as characterized by the amino acid sequence as defined in SEQ ID NO:1 and comprising a variable region of the light chain as characterized by the amino acid sequence as defined in SEQ ID NO:3 or a fragment, allelic variant, functional variant, glycosylation variant, fusion molecule or a chemical derivative thereof. Antibody BIWA8 comprises the variable region of the heavy chain as characterized in amino acid sequence SEQ ID NO:1 and variable region of the light chain as defined in amino acid sequence SEQ ID NO:3.

In another most preferred embodiment, the invention relates to an antibody molecule according to the invention wherein the variable region of the heavy chain consists of the amino acids as characterized by the amino acid sequence of SEQ ID NO:1 and wherein the variable region of the light chain consists of the amino acids as characterized by the amino acid sequence of SEQ ID NO:3.

In another preferred embodiment, the invention relates to an antibody molecule comprising a variable region of the heavy chain encoded by the nucleic acid sequence as defined in SEQ ID NO:4 or a fragment, allelic variant, functional variant, variant based on the degenerative nucleic acid code, fusion molecule or a chemical derivative thereof. Both antibodies BIWA4 and BIWA 8 comprise the variable region of the heavy chain as characterized in nucleic acid sequence SEQ ID NO:4.

In another more preferred embodiment, the invention relates to an antibody molecule wherein the variable region of the heavy chain is encoded by the nucleic acid sequence as defined in SEQ ID NO:4.

In another preferred embodiment, the invention relates to an antibody molecule comprising a variable region of the light chain encoded by the nucleic acid sequence as defined in SEQ ID NO:5 or a fragment, allelic variant, functional variant, variant based on the degenerative nucleic acid code, fusion molecule or a chemical derivative thereof. Antibody BIWA4 as used herein comprises the variable region of the light chain as defined in nucleic acid sequence SEQ ID NO:5.

In another more preferred embodiment, the invention relates to an antibody molecule wherein the variable region of the light chain is encoded by the nucleic acid sequence as defined in SEQ ID NO:5.

In another preferred embodiment, the invention relates to an antibody molecule comprising a variable region of the light chain encoded by the nucleic acid sequence as defined in SEQ ID NO:6 or a fragment, allelic variant, functional variant, variant based on the degenerative nucleic acid code, fusion molecule or a chemical derivative thereof. Antibody BIWA 8 comprises the variable region of the light chain as characterized in nucleic acid sequence SEQ ID NO:6.

In another more preferred embodiment, the invention relates to an antibody molecule wherein the variable region of the light chain is encoded by the nucleic acid sequence as defined in SEQ ID NO:6.

In another more preferred embodiment, the invention relates to an antibody molecule according to the invention comprising a variable region of the heavy chain encoded by the nucleic acid sequence as defined in SEQ ID NO:4 and comprising a variable region of the light chain encoded by the nucleic acid sequence as defined in SEQ ID NO:5 or a fragment, allelic variant, functional variant, variant based on the degenerative nucleic acid code, fusion molecule or a chemical derivative thereof. Antibody BIWA4 comprises the variable region of the heavy chain as characterized in nucleic acid sequence SEQ ID NO:4 and variable region of the light chain as defined in nucleic acid sequence SEQ ID NO:5.

In another most preferred embodiment, the invention relates to an antibody molecule according to to the invention wherein the variable region of the heavy chain is encoded by the nucleic acid sequence as defined in SEQ ID NO:4 and wherein the variable region of the light chain is encoded by the nucleic acid sequence as defined in SEQ ID NO:5.

In another more preferred embodiment, the invention relates to an antibody molecule according to the invention comprising a variable region of the heavy chain encoded by the nucleic acid sequence as defined in SEQ ID NO:4 and comprising a variable region of the light chain encoded by the nucleic acid sequence as defined in SEQ ID NO:6 or a fragment, allelic variant, functional variant, variant based on the degenerative nucleic acid code, fusion molecule or a chemical derivative thereof. Antibody BIWA8 comprises the variable region of the heavy chain as characterized in nucleic acid sequence SEQ ID NO:4 and variable region of the light chain as defined in nucleic acid sequence SEQ ID NO:6.

In another most preferred embodiment, the invention relates to an antibody molecule according to the invention wherein the variable region of the heavy chain is encoded by the nucleic acid sequence as defined in SEQ ID NO:4 and wherein the variable region of the light chain is encoded by the nucleic acid sequence as defined in SEQ ID NO:6.

To generate humanised CD44v6-specific antibody proteins the disclosed nucleic acid sequences were expressed (see infra and examples) by molecular biology methods known in the art.

The variable regions of the antibody proteins of the present invention are typically linked to at least a portion of the immunoglobulin constant region (Fc), typically that of a human immunoglobulin. Human constant region DNA sequences can be isolated in accordance with well-known procedures from a variety of human cells, but preferably immortalized B cells (see Kabat et al., supra, and WO 87/02671). Hence the antibody proteins of the invention may contain all or only a portion of the constant region as long as they exhibit specific binding to the CD44v6 antigen. The choice of the type and extent of the constant region depends on whether effector functions like complement fixation or antibody dependent cellular toxicity are desired, and on the desired pharmacological properties of the antibody protein. The antibody protein of the invention will typically be a tetramer consisting of two light chain/heavy chain pairs, but may also be dimeric, i.e. consisting of a light chain/heavy chain pair, e.g. a Fab or Fv fragment.

Therefore, in a further embodiment the invention relates to antibody proteins according to the invention, characterised in that they have a variable light chain region and a variable heavy chain region, each joined to a human constant region. In particular, the variable region of the light chain was joined to a human kappa constant region and the variable region of the heavy chain was joined to a human gamma-1 constant region. Other human constant regions for chimerizing light and heavy chains are also available to the expert.

Humanization of the variable region of a murine antibody may be achieved employing methods known in the art. EP 0239400 discloses grafting of the CDRs of a murine variable region into the framework of a human variable region. WO 90/07861 discloses methods of reshaping a CDR-grafted variable region by introducing additional framework modifications. WO 92/11018 discloses methods of producing humanized Ig combining donor CDRs with an acceptor framework that has a high homology to the donor framework. WO 92/05274 discloses the preparation of framework mutated antibodies starting from a murine antibody. Further prior art references related to humanization of murine monoclonal antibodies are EP 0368684; EP 0438310; WO 92/07075, or WO 92/22653.

In another preferred embodiment, the invention relates to an antibody molecule according to the invention characterised in that each of said variable region of the light chain and said variable region of the heavy chain region is separately joined to a human constant region.

In another more preferred embodiment, the invention relates to an antibody molecule according to the invention, wherein said human constant region of the light chain is a human kappa constant region.

In another more preferred embodiment, the invention relates to an antibody protein according to the invention, wherein said human constant region of the heavy chain is a human IgG1 constant region.

Preferred are also antibodies comprising the heavy chain as characterized by the amino acid sequence of SEQ ID NO:7 and/or the light chain as characterized by the amino acid sequence of SEQ ID NO:8 or as characterized by the amino acid sequence of SEQ ID NO:9.

Thus, another important embodiment is an antibody molecule according to the invention comprising a heavy chain as characterized by the amino acid sequence as defined in SEQ ID NO:7 and comprising a light chain as characterized by the amino acid sequence as defined in SEQ ID NO:8 or a fragment, allelic variant, functional variant, glycosylation variant, fusion molecule or a chemical derivative thereof Antibody BIWA4 comprises the heavy chain as characterized in amino acid sequence SEQ ID NO:7 and variable region of the light chain as defined in amino acid sequence SEQ ID NO:8.

In a most preferred embodiment, the invention relates to an antibody molecule according to the invention wherein the heavy chain consists of the amino acids as characterized by the amino acid sequence of SEQ ID NO:7 and wherein the light chain consists of the amino acids as characterized by the amino acid sequence of SEQ ID NO:8. Antibody BIWA4 consists of the sequences as disclosed in amino acid sequence SEQ ID NO:7 (heavy chain) and amino acid sequence SEQ ID NO:8 (light chain). BIWA4 is a CDR-grafted antibody without framework modifications. Surprisingly, this antibody has, despite lower binding affinity, superior therapeutic efficacy, better biodistribution and tumor uptake over the framework-mutated antibody BIWA8 (see example). It is a humanised version of antibody VFF-18 (=BIWA1) mentioned above, having the complementary determining regions of the murine monoclonal antibody VFF-18 in a completely human framework, and human constant regions. It is therefore an antibody of very low immunogenicity in man, which is a favorable trait. However, as it has no murine framework residues to optimise antigen binding, it has a significanty lower antigen binding affinity as its parent antibody VFF-18, and therefore would not have been regarded as a good candidate for a therapeutic drug. Unexpectedly, it has been found that BIWA4, despite its poor binding affinity, has a very favorable biodistribution and tumor uptake in vivo, making it superior to other humanised versions of VFF-18 with higher binding affinitiy.

Another important embodiment is an antibody molecule according to the invention comprising a heavy chain as characterized by the amino acid sequence as defined in SEQ ID NO:7 and comprising a light chain as characterized by the amino acid sequence as defined in SEQ ID NO:9 or a fragment, allelic variant, functional variant, glycosylation variant, fusion molecule or a chemical derivative thereof. Antibody BIWA8 comprises the heavy chain as characterized in amino acid sequence SEQ ID NO:7 and variable region of the light chain as defined in amino acid sequence SEQ ID NO:9.

In a most preferred embodiment, the invention relates to an antibody molecule according to the invention wherein the heavy chain consists of the amino acids as characterized by the amino acid sequence of SEQ ID NO:7 and wherein the light chain consists of the amino acids as characterized by the amino acid sequence of SEQ ID NO:9. Antibody BIWA8 consists of the sequences as disclosed in amino acid sequence SEQ ID NO:7 (heavy chain) and amino acid sequence SEQ ID NO:9 (light chain). BIWA8 is a CDR-grafted antibody with framework modifications. This antibody has significant higher binding affinity than BIWA4 (see example).

Preferred are also antibodies comprising the heavy chain as encoded by the nucleic acid sequence of SEQ ID NO:10 and/or the light chain as characterized by the nucleic acid sequence of SEQ ID NO:11 or as characterized by the nucleic acid sequence of SEQ ID NO:12. Said sequences include non-translated sequences and the leader sequence as cloned in vector pAD-CMV1/pAD-CMV19.

Therefore, another important embodiment is an antibody molecule according to the invention comprising a heavy chain as encoded by the nucleic acid sequence as defined in SEQ ID NO:10 and comprising a light chain as characterized by the nucleic acid sequence as defined in SEQ ID NO:11 or a fragment, allelic variant, functional variant, variant based on the degenerative nucleic acid code, fusion molecule or a chemical derivative thereof. Antibody BIWA4 comprises the heavy chain as encoded by nucleic acid sequence SEQ ID NO:10 and variable region of the light chain as encoded by nucleic acid sequence SEQ ID NO:11.

In a most preferred embodiment, the invention relates to an antibody molecule according to the invention wherein the heavy chain is encoded by the nucleic acid sequence of SEQ ID NO:10 and wherein the light chain is encoded by the nucleic acid sequence of SEQ ID NO:11.

Another important embodiment is an antibody molecule according to the invention comprising a heavy chain as encoded by the nucleic acid sequence as defined in SEQ ID NO:10 and comprising a light chain as characterized by the nucleic acid sequence as defined in SEQ ID NO:12 or a fragment, allelic variant, functional variant, variant based on the degenerative nucleic acid code, fusion molecule or a chemical derivative thereof. Antibody BIWA8 comprises the heavy chain as encoded by nucleic acid sequence SEQ ID NO:10 and variable region of the light chain as encoded by nucleic acid sequence SEQ ID NO:12.

In a most preferred embodiment, the invention relates to an antibody molecule according to the invention wherein the heavy chain is encoded by the nucleic acid sequence of SEQ ID NO:10 and wherein the light chain is encoded by the nucleic acid sequence of SEQ ID NO:12.

Preferred are also antibodies comprising the heavy chain as encoded by the nucleic acid sequence of SEQ ID NO:13 and/or the light chain as characterized by the nucleic acid sequence of SEQ ID NO:14 or as characterized by the nucleic acid sequence of SEQ ID NO:15. Said sequences include the leader sequence as cloned in vector NSKG1val.

Therefore, another important embodiment is an antibody molecule according to the invention comprising a heavy chain as encoded by the nucleic acid sequence as defined in SEQ ID NO:13 and comprising a light chain as characterized by the nucleic acid sequence as defined in SEQ D NO:14 or a fragment, allelic variant, functional variant, variant based on the degenerative nucleic acid code, fusion molecule or a chemical derivative thereof. Antibody BIWA4 comprises the heavy chain as encoded by nucleic acid sequence SEQ5 ID NO:13 and variable region of the light chain as encoded by nucleic acid sequence SEQ ID NO:14.

In a most preferred embodiment, the invention relates to an antibody molecule according to the invention wherein the heavy chain is encoded by the nucleic acid sequence of SEQ ID NO:13 and wherein the light chain is encoded by the nucleic acid sequence of SEQ ID NO:14.

Another important embodiment is an antibody molecule according to the invention comprising a heavy chain as encoded by the nucleic acid sequence as defined in SEQ ID NO:13 and comprising a light chain as characterized by the nucleic acid sequence as defined in SEQ ID NO:15 or a fragment, allelic variant, functional variant, variant based on the degenerative nucleic acid code, fusion molecule or a chemical derivative thereof. Antibody BIWA8 comprises the heavy chain as encoded by nucleic acid sequence SEQ ID NO:13 and variable region of the light chain as encoded by nucleic acid sequence SEQ ID NO:15.

In a most preferred embodiment, the invention relates to an antibody molecule according to the invention wherein the heavy chain is encoded by the nucleic acid sequence of SEQ ID NO:13 and wherein the light chain is encoded by the nucleic acid sequence of SEQ ID NO:15.

Most preferred is the antibody protein comprising the heavy and light chain as encoded by the nucleic acid sequence of SEQ ID NO:16. Said sequence includes the leader sequence as cloned in vector N5KG1val.

Therefore, another highly important embodiment is an antibody molecule according to the invention comprising a heavy and light chain as encoded by the nucleic acid sequence as defined in SEQ ID NO:16 or a fragment, allelic variant, functional variant, variant based on the degenerative nucleic acid code, fusion molecule or a chemical derivative thereof. Antibody BIWA4 comprises the heavy and light chain as encoded by nucleic acid sequence SEQ ID NO:16.

In a most preferred embodiment, the invention relates to an antibody molecule according to the invention wherein the heavy and light chain is encoded by the nucleic acid sequence of SEQ ID NO:16. This sequence is encoding the entire antibody BIWA4.

The antibody proteins of the invention provide a highly specific tool for targeting therapeutic agents to the CD44v6 antigen. Therefore, in a further aspect, the invention relates to antibody proteins according to the invention, wherein said antibody protein is conjugated to a therapeutic agent. Of the many therapeutic agents known in the art, therapeutic agents selected from the group consisting of radioisotopes, toxins, toxoids, inflammatogenic agents, enzymes, antisense molecules, peptides, cytokines, and chemotherapeutic agents are preferred. Among the radioisotopes, gamma, beta and alpha-emitting radioisotopes may be used as a therapeutic agent. β-emitting radioisotopes are preferred as therapeutic radioisotopes. $^{186}$Rhenium, $^{188}$Rhenium, $^{131}$Iodine and $^{90}$Yttrium have been proven to be particularly useful β-emitting isotopes to achieve localized irradiation and destruction of malignant tumor cells. Therefore, radioisotopes selected from the group consisting of $^{186}$Rhenium, $^{188}$Rhenium, $^{131}$Iodine and $^{90}$Yttrium are particularly preferred as therapeutic agents conjugated to the antibody proteins of the invention. For example, for the radioiodination of an antibody of the invention, a method as disclosed in WO 93/05804 may be employed.

Thus, a more preferred aspect of the present invention is an antibody protein according to the invention, wherein said therapeutic agent is a therapeutic agent selected from the group consisting of radioisotopes, toxins, toxoids, pro-drugs and chemotherapeutic agents.

A more preferred aspect of the present invention is an antibody protein according to the invention, wherein said therapeutic agent is linked to the antibody protein via a linker selected from the group of MAG-3 (U.S. Pat. No. 5,082,930 A, EP 0247866 B1 (page 2 lines 55–56–page 3 lines 1–23)); MAG-2 GABA (U.S. Pat. No. 5,681,927 A, EP 0284071 B1 (page 6 lines 9–29)); and N2S2 ((=phenthioate) U.S. Pat. Nos. 4,897,255 A, 5,242,679 A, EP 0188256 B1 (page 2, lines 38–page 3, lines 18)), all herein incorporated by reference.

The formulae of said linkers are as follows:

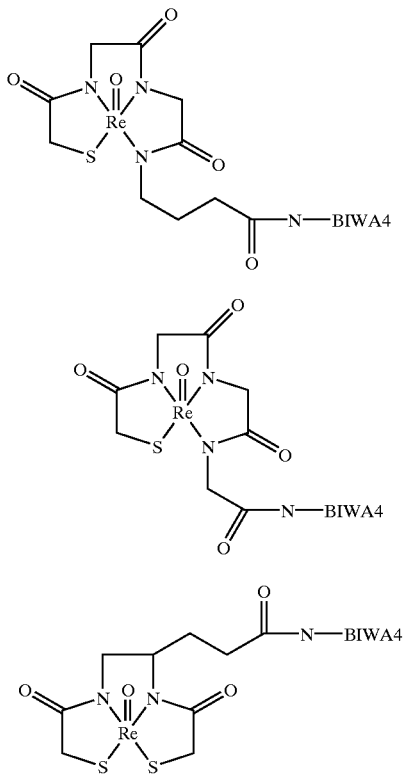

MAG2-GABA

MAG3

Phenthioate

A more preferred aspect of the present invention is an antibody protein according to the invention, wherein said therapeutic agent is linked to the antibody protein via MAG-2 GABA.

A more preferred aspect of the present invention is an antibody protein according to the invention, wherein said radioisotope is a β-emitting radioisotope.

A more preferred aspect of the present invention is an antibody protein according to the invention, wherein said radioisotope is selected from the group consisting of $^{186}$Rhenium, $^{188}$Rhenium, $^{131}$Iodine and 90Yttrium.

A more preferred aspect of the present invention is an antibody protein according to the invention, wherein said radioisotope is $^{186}$Rhenium.

A firther aspect of the present invention pertains to antibody proteins according to the invention, characterised in that they are labelled. Such an CD44v6-specific labelled antibody allows for the localisation and/or detection of the CD44v6 antigen in vitro and/or in vivo. A label is defined as a marker that may be directly or indirectly detectable. An indirect marker is defined as a marker that cannot be detected by itself but needs a further directly detectable marker specific for the indirect marker. Preferred labels for practicing the invention are detectable markers. From the large variety of detectable markers, a detectable marker selected from the group consisting of enzymes, dyes, radioisotopes, digoxygenin, and biotin is most preferred.

Thus, a more preferred aspect of the present invention is an antibody protein according to the invention, characterised in that it is labelled. More preferred is the antibody protein according to the invention, wherein said label is a detectable marker. Also more preferred is the antibody protein according to the invention, wherein the detectable marker is a detectable marker selected from the group consisting of enzymes, dyes, radioisotopes, digoxygenin, and biotin.

A further aspect of the present invention relates to antibody proteins according to the invention, characterised in that they are conjugated to an imageable agent. A large variety of imageable agents, especially radioisotopes, are available from the state of the art. For practising the invention gamma-emitting isotopes are more preferred. Most preferred is $^{125}$Iodine.

Therefore, a more preferred aspect of the present invention is an antibody protein to the invention conjugated to an imageable agent. A more preferred aspect of the present invention is an antibody protein according to the invention, wherein the imageable agent is a radioisotope. A more preferred aspect of the present invention is an antibody protein according to the invention, wherein said radioisotope is a γ-emitting radioisotope. A more preferred aspect of the present invention is an antibody protein according to the invention, wherein said radioisotope is $^{125}$I.

Therefore, a more preferred aspect of the present invention is an antibody protein conjugated to a radioisotope as described above, wherein the antibody protein has specific activity of from about 0.5 to about 15 mCi/mg, or from about 0.5 to about 14 mCi/mg, preferably about 1 to about 10 mCi/mg, preferably about 1 to about 5 mCi/mg, and most preferably 2 to 6 mCi/mg or 1 to 3 mCi/mg.

Another preferred embodiment of the present invention is a pharmaceutical composition containing an antibody according to the invention and a pharmaceutically acceptable carrier or excipient.

A pharmaceutically acceptable carrier can contain physiologically acceptable compounds that act, for example, to stabilize or to increase the absorption of an AMPA glutamate receptor agonist, antagonist or modulator. Such physiologically acceptable compounds include, for example, carbohydrates, such as glucose, sucrose or dextrans, antioxidants, such as ascorbic acid or glutathione, chelating agents, low molecular weight proteins or other stabilizers or excipients (see also e.g. Remington's Pharmaceutical Sciences (1990), 18th ed. Mack Publ., Easton). One skilled in the art would know that the choice of a pharmaceutically acceptable carrier, including a physiologically acceptable compound, depends, for example, on the route of administration of the composition.

In an animal or human body, it can prove advantageous to apply the pharmaceutical compositions as described above via an intravenous or other route, e.g. systemically, locally or topically to the tissue or organ of interest, depending on the type and origin of the disease or problem treated, e.g. a tumor. For example, a systemic mode of action is desired when different organs or organ systems are in need of treatment as in e.g. systemic autoimmune diseases, or allergies, or transplantations of foreign organs or tissues, or tumors that are diffuse or difficult to localise. A local mode of action would be considered when only local manifestations of neoplastic or immunologic action are expected, such as, for example local tumors.

The pharmaceutical compositions comprising antibody proteins of the present invention may be applied by different routes of application known to the expert, notably intravenous injection or direct injection into target tissues. For systemic application, the intravenous, intravascular, intramuscular, intraarterial, intraperitoneal, oral, or intrathecal routes are preferred. A more local application can be effected subcutaneously, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, pharmaceutical antibody compositions may be administered once or several times, also intermittently, for instance on a daily basis for several days, weeks or months and in different dosages.

For preparing suitable pharmaceutical compositions comprising antibody preparations for the applications described above, the expert may use known injectable, physiologically acceptable sterile solutions. For preparing a ready-to-use solution for parenteral injection or infusion, aqueous isotonic solutions, such as e.g. saline or corresponding plasma protein solutions are readily available. The pharmaceutical compositions may be present as lyophylisates or dry preparations, which can be reconstituted with a known injectable solution directly before use under sterile conditions, e.g. as a kit of parts. The final preparation of the antibody compositions of the present invention are prepared for injection, infusion or perfusion by mixing purified antibodies according to the invention with a sterile physiologically acceptable solution, that may be supplemented with known carrier substances or/and additives (e.g. serum albumin, dextrose, sodium bisulfite, EDTA).

The amount of the antibody applied depends on the nature of the disease. In cancer patients, the applied dose of a 'naked' antibody which is comprised in the pharmaceutical composition according to the invention may be between 0.1 and 100 mg/m$^2$, preferably between 5 and 50 mg/m$^2$ per application, preferably 10 mg/m$^2$ to about 40 mg/m$^2$, preferably 10 mg/m$^2$ to about 30 mg/m$^2$, also preferably 20 mg/m$^2$ to about 30 mg/$^2$, and most preferably about 25 mg/m$^2$ body surface area. Also most preferred is an antibody protein dose of about 50 mg/m$^2$ body surface area.

The dose of radioactivity applied to the patient per administration has to be high enough to be effective, but must be below the dose limiting toxicity (DLT). For pharmaceutical compositions comprising radiolabeled antibodies, e.g. with $^{186}$Rhenium, the maximally tolerated dose (MTD) has to be determined which must not be exceeded in therapeutic settings. Application of radiolabeled antibody to cancer patients may then be carried out by repeated (monthly or weekly) intravenous infusion of a dose which is below the MTD (See e.g. Welt et al. (1994) *J. Clin. Oncol.* 12: 1193–1203). Multiple administrations are preferred, generally at weekly intervals; however, radiolabelled materials should be administered at longer intervals, i.e., 4–24 weeks apart, preferable 12–20 weeks apart. The artisan may choose, however, to divide the administration into two or more applications, which may be applied shortly after each other, or at some other predetermined interval ranging, e.g. from 1 day to 1 week.

Furthermore, the applied radioactivity dose will be in accordance with the guidelines outlined below. In general, the radioactivity dose per administration will be between 30 and 75 mCi/m$^2$ body surface area (BSA). Thus, the amount of radiolabelled antibody in the pharmaceutical composition according to the invention, preferably labelled with $^{186}$Rhenium, $^{188}$Rhenium, $^{99m}$Technetium, $^{133}$Iodine, or $^{90}$Yttrium, most preferably labelled with $^{186}$Rhenium, to be applied to a patient is 10, 20, 30, 40, 50 or 60 mCi/m$^2$, preferably 50 mCi/m$^2$. In a preferred embodiment, the invention relates to a pharmaceutical composition, wherein the dose of said radiolabelled antibody according to the invention is MTD, preferably 50 mCi/m$^2$. This is extensively exemplified in clinical studies as set out in examples 3 to 6.

Preferred also is a pharmaceutical composition according to the invention comprising an antibody protein conjugated to a radioisotope according to the invention as defined supra, wherein the antibody protein has specific activity of from about 0.5 to about 15 mCi/mg, or from about 0.5 to about 14 mCi/mg, preferably about 1 to about 10 mCi/mg, preferably about 1 to about 5 mCi/mg, and most preferably 2 to 6 mCi/mg or 1 to 3 mCi/mg.

Preferred also is a pharmaceutical composition according to the invention comprising an antibody protein conjugated to a radioisotope according to the invention as defined supra, wherein said antibody or antibody derivative is in an aqueous solution at pH of from about 7 to about 8, and at a concentration of from about 0.5 to about 2.0 mg/ml.

A preferred embodiment is a pharmaceutical composition according to the invention, further comprising one or more radioprotectants selected from the group of ascorbic acid, gentisic acid, reductic acid, erythrorbic acid, p-aninobenzoic acid, 4hydroxybenzoic acid, nicotinic acid, nicotinamide, 2-5-dihydroxy-1,4-benzenedisulfonic acid, povidone, inositol, and/or citrate.

Preferred is a pharmaceutical composition according to the invention, wherein the radioprotectant is ascorbic acid.

Another preferred embodiment is a pharmaceutical composition according to the invention, wherein said antibody protein comprises an antibody molecule selected from the group of antibody molecules BIWA4 or BIWA8 as described supra linked to $^{186}$Rhenium via MAG-2 GABA further comprising the radioprotectant ascorbic acid.

Another preferred embodiment of the present invention is the use of an antibody protein according to the invention in the manufacture of a medicament for treatment of cancer. In a preferred embodiment the present invention relates to the use of antibody proteins according to the invention conjugated to a therapeutic agent as described above for the treatment of cancer. Cancer includes any disease associated with malignant growth such as solid tumors, sarcomas and leukemias. A necessary precondition for such diseases is the expression of CD44v6. Cancer according to the invention includes, but is not limited to:

1) The treatment of epithelial carcinomas including breast, lung, colorectal, head and neck, pancreatic, ovarian, bladder, gastric, skin, endometrial, ovarian, testicular, esophageal, prostatic and renal origin;
2) Bone and soft-tissue sarcomas: Osteosarcoma, chondrosarcoma, fibrosarcoma, malignant fibrous histiocytoma (MFH), leiomyosarcoma;
3) Hematopoietic malignancies: Hodgkin's and non-Hodgkin's lymphomas, leukemias;
4) Neuroectodermal tumors: Peripheral nerve tumors, astrocytomas, melanomas;
5) Mesotheliomas Examples for cancerous disease states associated with solid tumors include, but are not limited to: colorectal cancer, non-small cell lung cancer, breast cancer, head and neck cancer, ovarian cancer, lung cancer, bladder cancer, pancreatic cancer and metastatic cancers of the brain.

Thus, a preferred embodiment is the use of an antibody protein according to the invention wherein said cancer is selected from the group consisting of colorectal cancer, non-small cell lung cancer, breast cancer, head and neck cancer, ovarian cancer, lung cancer, bladder cancer, pancreatic cancer and metastatic cancers of the brain.

Preferably also is the use of an antibody protein according to the invention as defined supra in the manufacture of a medicament for treatment of cancer, wherein the amount of antibody protein per application is between 0.1 and 100 mg/m², preferably between 5 and 50 mg/m², preferably 10 mg/m² to about 40 mg/m², preferably 10 mg/m² to about 30 mg/m², also preferably 20 mg/m² to about 30 mg/m², and most preferably about 25 mg/m² body surface area. Also most preferred is an antibody protein dose of about 50 mg/m² body surface area.

Preferred also is the use of an antibody protein conjugated to a radioisotope according to the invention as defined supra in the manufacture of a medicament for treatment of cancer, wherein the radioactivity dose per administration is between 30 and 75 mCi/m² body surface area (BSA). preferred is the use of an antibody protein conjugated to a radioisotope according to the invention as defined supra in the manufacture of a medicament for treatment of cancer, wherein the antibody protein according to the invention is radiolabelled with $^{186}$Rhenium, $^{188}$Rhenium, $^{99m}$Technetium, $^{131}$Iodine, or 90Yttrium, and most preferably is labelled with $^{186}$Renium. In yet another preferred embodiment the invention relates to the use of an antibody protein conjugated to a radioisotope according to the invention as defined supra in the manufacture of a medicament for treatment of cancer, wherein to antibody dose is 10, 20, 30, 40, 50 or 60 mCi/m², most preferably 50 mCi/m². This is extensively exemplified in clinical studies as set out in examples 3 to 6.

Preferred also is the use of an antibody protein conjugated to a radioisotope according to the invention as defined supra in the manufacture of a medicament for treatment of cancer, wherein the antibody protein has specific activity of from about 0.5 to about 15 mCi/mg, or from about 0.5 to about 14 mCi/mg, preferably about 1 to about 10 mCi/mg, preferably about 1 to about 5 mCi/mg, and most preferably 2 to 6 mCi/mg or 1 to 3 mCi/mg.

Preferred also is the use of an antibody protein conjugated to a radioisotope according to the invention as defined supra in the manufacture of a medicament for treatment of cancer, wherein said antibody or antibody derivative is in an aqueous solution at pH of from about 7 to about 8, and at a concentration of from about 0.5 to about 2.0 mg/ml.

The invention further relates to a method of cancer treatment, wherein an antibody protein according to the invention is administered once to several times to an individual in need thereof, said antibody protein selectively binds to CD44v6, destroys tumor cells via the therapeutic agent linked to the antibody protein and the therapeutic success is monitored. Said antibody protein may be present as naked/unmodified antibody protein, modified antibody protein, such as e.g. fusion protein, or antibody protein conjugated to a therapeutic agent, which comprises contacting the tumor with an effective amount of said antibodies. The method of treating tumors as described above may be effective in vitro or in vivo. Cancer is any cancer as described above.

The amount of the antibody applied depends on the nature of the disease. In cancer patients, the applied dose of a 'naked' antibody may be between 0.1 and 100 mg/m², preferably between 5 and 50 mg/m² per application, preferably 10 mg/m² to about 40 mg/m², preferably 10 mg/m² to about 30 mg/m², also preferably 20 mg/m² to about 30 mg/m², and most preferably about 25 mg/m² body surface area. Also most preferred is an antibody protein dose of about 50 mg/m² body surface area.

The dose of radioactivity applied to the patient per administration has be high enough to be effecfive, but must be below the dose limiting toxicity (DLT). For radiolabeled antibodies, e.g. with $^{186}$Rhenium, the maximally tolerated dose (MTD) has to be determined which must not be exceeded in therapeutic settings. Application of radiolabeled antibody to cancer patients may then be carried out by repeated (monthly or weekly) intravenous infusion of a dose which is below the MTD (See e.g. Welt et al. (1994) *J. Clin. Oncol.* 12: 1193–1203). Multiple administrations are preferred, generally at weekly intervals; however, radiolabelled materials should be administered at longer intervals, i.e., 4–24 weeks apart, preferable 12–20 weeks apart. The artisan may choose, however, to divide the administration into two or more applications, which may be applied shortly after each other, or at some other predetermined interval ranging, e.g. from 1 day to 1 week.

Furthermore, the applied radioactivity dose will be in accordance with the guidelines outlined below. In general, the radioactivity dose per administration will be between 30 and 75 mCi/m² body surface area (BSA). Thus, the amount of radiolabelled antibody, preferably labelled with $^{186}$Rhenium, $^{188}$Rhenium, $^{99m}$Technetium, $^{131}$Iodine, or 90Yttrium, most preferably labelled with $^{186}$Rhenium, to be applied to a patient is 10, 20, 30, 40, 50 or 60 mCi/m², preferably 50 mCi/m². In a preferred embodiment, the invention relates to a method of treatment, wherein the radiolabelled antibody as described above is administered to a patient suffering from cancer, wherein the dose of said radiolabelled antibody is MTD, preferably 50 mCi/m², whereby said cancer is prevented or treated. This is extensively exemplified in clinical studies as set out in examples 3 to 6.

Preferred also is a method of cancer treatment according to the invention (see above), wherein the antibody protein conjugated to a radioisotope according to the invention as defined supra has specific activity of from about 0.5 to about 15 mCi/mg, or from about 0.5 to about 14 mCi/mg, preferably about 1 to about 10 mCi/mg, preferably about 1 to about 5 mCi/mg, and most preferably 2 to 6 mCi/mg or 1 to 3 mCi/mg.

Preferred also is a method of cancer treatment according to the invention (see above), wherein the antibody protein conjugated to a radioisotope according to the invention as defined supra is in an aqueous solution at pH of from about 7 to about 8, and at a concentration of from about 0.5 to about 2.0 mg/ml.

Preferably, the invention relates to a method according to the invention, wherein the tumor is a tumor selected from the cancer group consisting of colorectal cancers, non-small cell lung cancers, breast cancers, head and neck cancer, ovarian cancers, lung cancers, bladder cancers, pancreatic cancers and metastatic cancers of the brain.

A further aspect of the present invention is a nucleic acid, characterised in that it codes for an antibody protein according to the invention. Said nucleic acid may be RNA or preferably DNA. Said DNA molecule may be chemically synthesized. First, suitable oligonucleotides can be synthesized with methods known in the art (e.g. Gait, M. J., 1984, *Oligonucleotide Synthesis. A Practical Approach.* IRL Press, Oxford, UK), which can be used to produce a synthetic gene. Methods to generate synthetic genes are known in the art (e.g. Stemmer et al. 1995, *Single-step assembly of a gene and entire plasmid from large numbers of oligodeoxyribonucleotides*, Gene 164(1): 49–53; Ye et al. 1992, *Gene synthesis and expression in E. coli for pump, a human matrix metalloproteinase*, Biochem Biophys Res Commun 186(1):143–9; Hayden et Mandecki 1988, Gene synthesis by serial cloning of oligonucleotides, DNA 7(8): 571–7). These methods can be used to synthesize any DNA molecule disclosed in the present application, e.g. the DNA encoding BIWA4.

Preferably, too, a nucleic acid according to the invention is characterised in that it contains 5' or 3' or 5' and 3' untranslated regions. The nucleic acid according to the invention may contain other untranslated regions upstream and/or downstream. The untranslated region may contain a regulatory element, such as e.g. a transcription initiation unit (promoter) or enhancer. Said promoter may, for example, be a constitutive, inducible or development-controlled promoter. Preferably, without ruling out other known promoters, the constitutive promoters of the human Cytomegalovirus (CMV) and Rous sarcoma virus (RSV), as well as the Simian virus 40 (SV40) and Herpes simplex promoter. Inducible promoters according to the invention comprise antibiotic-resistance promoters, heat-shock promoters, hormone-inducible "Mammary tumour virus promoter" and the metallothioneine promoter. Preferably, too, a nucleic acid according to the invention is characterised in that it codes for a fragment of the antibody protein according to the invention. This refers to part of the polypeptide according to the invention.

Preferably, a nucleic acid according to the invention is a nucleic acid as disclosed in SEQ ID SEQ ID NO:4, 5, 6, 10, 11, 12, 13, 14, 15, and/or 16. Most preferred, said nucleic acid is a nucleic acid of SEQ ID NO:16.

Another important aspect of the present invention is a recombinant DNA vector, characterised in that it contains a nucleic acid according to the invention. Preferably, said vector contains a nucleic acid as characterized in SEQ ID NO:4, 5, 6, 10, 11, 12, 13, 14, 15, and/or 16. Most preferred, said vector contains the nucleic acid as characterized in SEQ ID NO:16.

Examples are viral vectors such as e.g. Vaccinia, Semliki-Forest-Virus and Adenovirus. Vectors for use in COS-cells have the SV40 origin of replication and make it possible to achieve high copy numbers of the plasmids. Vectors for use in insect cells are, for example, E. coli transfer vectors and contain e.g. the DNA coding for polyhedrin as promoter.

Another preferred aspect of the present invention is a recombinant DNA vector according to the invention, characterized in that it is an expression vector.

Another preferred aspect of the present invention is a recombinant DNA vector according to the invention, characterized in that it is vector pAD-CMV or a functional derivative thereof. Such derivatives are e.g. pAD-CMV1, pAD-CMV19 or pAD-CMV25.

Another preferred aspect of the present invention is a recombinant DNA vector according to the invention, characterized in that it is the of SEQ ID NO:17 or a functional derivative thereof.

Another preferred aspect of the present invention is a recombinant DNA vector according to the invention, characterized in that it is the of SEQ ID NO:18 or a functional derivative thereof.

Preferably also, said vectors comprise one or several of the nucleic acid molecules as characterized in SEQ ID NO:4, 5, 6, 10, 11, 12, 13, 14, 15, and/or 16.

Preferred is also a vector as disclosed in U.S. Pat. Nos. 5,648,267 A or 5,733,779 A comprising a nucleotide sequence according to the invention. Preferably also, said vector comprises one or several of the nucleic acid molecules as characterized in SEQ ID NO:4, 5, 6, 10, 11, 12, 13, 14, 15, and/or 16. Another preferred aspect of the present invention is a recombinant DNA vector according to the invention, characterized in that it is vector N5KG1Val or a derivative thereof.

Another important aspect is a host, characterised in that it contains a vector according to the invention.

Another important aspect is a host according to the invention, characterised in that it is a eukaryotic host cell.

The eukaryotic host cells according to the invention include fungi, such as e.g. Pichia pastoris, Saccharomyces cerevisiae, Schizosaccharomyces, Trichoderma, insect cells (e.g. from Spodoptera frugiperda Sf-9, with a Baculovirus expression system), plant cells, e.g. from Nicotiana tabacum, mammalian cells, e.g. COS cells, BHK, CHO or myeloma cells.

In descendants of the cells of the immune system in which antibody proteins are also formed in our body, the antibody proteins according to the invention are particularly well folded and glycosylated. Mammalian host cells, preferably CHO or COS cells are preferred, e.g. a CHO DG44 (Urlaub and Chasin, Proc. Natl. Acad. Sci. U.S.A. 77(7): 4216–20 (1980)), or CHO-K1 (ATCC CCL-61) cells. Thus, another preferred aspect is a host according to the invention according to the invention, characterised in that it is a BHK, CHO or COS cell, most preferred CHO DG44 or CHO-K1 (ATCC CCL-61) cells.

Another preferred aspect is a host according to the invention, characterised in that it is a bacteriophage.

Another preferred aspect is a host according to the invention, characterised in that it is a prokaryotic host cell. Examples of prokaryotic host cells are Escherichia coli, Bacillus subtilis, Streptomyces or Proteus mirabilis.

The invention further relates to a process for preparing an antibody protein according to the invention, characterized in that it comprises the following steps: a host according to the invention is cultivated under conditions in which said antibody protein is expressed by said host cell and said antibody protein is isolated. The antibody according to the invention may be produced as follows. Nucleic acid molecules coding for the light chain and the heavy chain may be synthesised chemically and enzymatically by standard methods. First, suitable oligonucleotides can be synthesized with methods known in the art (details supra). Methods to generate synthetic genes from oligonucleotides are known in the art (details supra). These nucleic acid molecules encoding the antibody heavy and light chains may be cloned into an expression vector (either both chains in one vector molecule, or each chain into a separate vector molecule), which then is introduced into a host cell. The host cell preferably is a mamalian host cell (details supra), e.g. a COS, CHO, or BHK cell, more preferably a chinese hamster ovary (CHO) cell, The host cell then is cultured in a suitable culture medium under conditions where the antibody is produced, and the antibody is then isolated from the culture according to standard procedures. Procedures for production of antibodies from recombinant DNA in host cells and respective expression vectors are well-known in the art (see e.g. WO 94/11523, WO 97/9351, EP 0481790.)

The invention preferably relates to a process according to the invention, characterised in that said host is a mammalian cell, preferably a CHO or COS cell.

The invention preferably relates to a process according to the invention, characterised in that said host cell is co-transfected with two plasmids which carry the expression units for the light or the heavy chain.

The following examples serve to further illustrate the present invention; but the same should not be construed as limiting the scope of the invention disclosed herein.

EXAMPLES

Example 1

Radioimmunotherapy

Materials And Methods

Monoclonal antibodies. mMAb BIWA 1=VFF 18 (which is secreted by a hybridoma cell line which has been deposited on 7 Jun. 1994 with the accession number DSM ACC2174 with the DSM-Deutsche Sammlung für Mikroorganismen und Zellkulturen GmbH, Mascheroder Weg 1b, D-38124 Braunschweig, Deutschland; see also WO 95/33771) was generated by immunizing BALB/c mice with glutathione S-transferase fusion protein containing the human CD44 domains v3–v10 (Heider et al., 1996). The epitope recognized by BIWA 1 has been mapped to amino acids 360–370 in domain v6 of CD44 (numbering according to Kugelman et al. (1992)). The batch used for the present studies was obtained after purification on protein-G-Sepharose and dialysis against PBS.

MAb U36 (IgG1) was derived after immunization of mice with the HNSCC cell line UM-SCC-22B and recognised a different epitope within CD44v6 as BIWA 1. U36 was purified from a concentrated tissue culture supernatant by affinity chromatography on protein-A-Sepharose and further purified on Q-Sepharose.

Generation of chimeric and humanized MAbs. mRNA was isolated from the BIWA 1 hybridoma cell line by use of the QuickPrep mRNA Purification Kit (Pharmacia, Uppsala, Sweden). cDNA from the variable heavy ($V_H$) and variable light ($V_L$) chain was generated by RT-PCR.

The fragments were cloned into the TA cloning vector pCR II (Invitrogen, Groningen, The Netherlands) and sequenced. Two expression vectors derived from the plasmid pAD CMVI (Himmler et al., 1990) were constructed carrying the constant region of human gamma-1 and the constant region of the human kappa light chain, respectively. Subsequently, the $V_H$ and $V_L$ fragments of BIWA 1 were cloned into the corresponding expression vectors in front of the constant regions. The chimeric antibody was named cMAb BIWA 2. Humanized versions of the BIWA 1 heavy and light chain variable regions (generated by CDR grafting) were cloned in front of the immunoglobulin constant regions of the above mentioned expression vectors. For the construction of humanized antibodies, the human variable regions used were derived for the heavy chain from the human immunoglobulin fragment accession number S31669 of databank GenPept and for the light chain from the human immunoglobulin HUMIGKAX (rearranged anti-myelin kappa chain), Genbank accession number M29469. The resulting MAbs were named hMAb BIWA 4 and BIWA 8, respectively. BIWA 8 contained two amino acids of the murine parent antibody within the light chain framework 2 while BIWA 4 did not contain murine residues in the framework.

Recombinant MAbs were stably expressed in dihydrofolate reductase deficient Chinese hamster ovary cells by electroporation with heavy and light chain expression plasmids. Cells were seeded into 96 well microtiter plates at densities of 500 and 100 cells/well in selection medium (α-MEM with 10% dialyzed fetal calf serum). When colonies became visible (after~14 days), culture supernatants were tested for their IgG content by ELISA, and the best producers were expanded. Gene amplification was performed by culturing in the presence of increasing concentrations of methotrexate (20–500 nM).

Laboratory scale production of chimeric and humanized MAbs was performed in a standard culture medium containing 1% fetal calf serum. IgG fractions were purified from tissue culture supernatants by affinity chromatography on protein A sepharose. Purity was tested by SDS-PAGE and high performance size exclusion chromatography.

Evaluation of antibody affinity. Measurement of kinetic and affinity constants using recombinant antigen was performed on a BIAcore 2000 system (BIAcore AB, Uppsala, Sweden). A glutathione-S-transferase fusion protein containing domains v3–v10 of human CD44 (GST/CD44v3–v10; 20 μg/ml) was immobilized on a CM5 sensor chip by the amine coupling method according to the manufacturer's instructions, using 10 mM sodium acetate pH 5.0 as coupling buffer. 35 μl of MAb at various concentrations (8–67 nM) in HBS (10 mM HEPES, pH 7.4, 150 mM NaCl, 3.4 mM EDTA, 0.05% BLAcore surfactant P20) were injected over the antigen-coated surface at a flow rate of 5 μL/min. Dissociation of the MAb was assessed for 5 minutes in buffer flow (HBS). Between two analyses, the surface of the chip was regenerated with a single pulse of 15 μl 30 mM HCl. Analysis of the data and calculation of the kinetic constants were performed with BIAcore's BIAevaluation software, version 2.1. Association rates ($k_a$), dissociation rates ($k_d$), and dissociation constants ($K_d$) were assessed for all antibodies.

Relative binding affinities were also evaluated by competitive cell ELISA. Human A431 cells, originating from an epidermoid carcinoma of the vulva and known to express high levels of CD44v6, were seeded in 96 well tissue culture plates in 200 μl per well RPMI 1640 with 10% fetal calf serum at a density of $2.5-5 \times 10^5$ cells/ml. The plates were incubated overnight at 37° C. in a humidified incubator with 5% $CO_2$ in air. After removal of the medium the cells were washed once with PBS, fixed with 96% ethanol for 1 min, and washed again with PBS. cMAb BIWA 2, hMAb BIWA 4 and hMAb BIWA 8 (prediluted to 10 μg/ml) were applied in 1:2 serial dilutions (8 steps) in 100 μl/well in PBS/0.5% BSA/0.05% Tween 20 (assay buffer) and incubated for 30 min at room temperature. 100 μl prediluted mMAb BIWA 1 (20 ng/ml) was added and the plates were incubated for 2 h at room temperature on an orbital shaker. Control samples contained prediluted samples only, without BIWA 1 (0% control) or BIWA 1 only without any competing antibodies (100% control). After washing three times with PBS/0.05% Tween 20 (washing buffer), 100 μl of the secondary antibody (peroxidase-conjugated goat anti-mouse Fc, diluted 1:15, 000 in assay buffer, DAKO Copenhagen, Denmark) was added for detection of mMAb BIWA 1, and plates were incubated for 1 h at room temperature on an orbital shaker. After washing three times with washing buffer, the plates were developed with 100 μl/well tetramethylbenzidine substrate solution (Kierkegaard and Perry Laboratories, Gaithersburg, USA). The reaction was stopped after 15 min with 50 μl/well 1 M phosphoric acid. Absorbance was measured in an ELISA plate reader at 450 nm (reference 610–690 nm).

Radioiodination of Antibodies. Iodination of MAbs was performed essentially as described by Haisma el al. (1986), using either $^{125}$I (100 mCi/mL) or $^{131}$I (200 mCi/mL), both purchased from Amersham, Aylesbury, England. One mg MAb IgG dissolved in 500 μl PBS, pH=7.4, and 1 mCi $^{125}$I or $^{131}$I were mixed in a vial coated with 75 μg Iodogen (Pierce, Oud Bijerland, The Netherlands). After 5 minutes of incubation at room temperature, free iodine was removed by gelfiltration on a PD10-column (Pharmacia-LKB, Woerden, The Netherlands). After removal of unbound 125I or $^{131}$I the radiochemical purity always exceeded 97% as determined by TLC and HPLC procedures which have been described before (Van Gog et al., 1997a). No aggregates or fragments were formed as assessed by HPLC analysis.

Preparation of Rhenium-186-labeled MAbs. $^{186}$Re-labeled MAbs were prepared according to a multistep procedure using the chelate S-benzoylmercaptoacyltriglycine (S-benzoyl-MAG3) as previously described (Van Gog et al., 1997a). In this procedure a solid-state synthesis for the preparation of $^{186}$Re-MAG3 is followed by esterification with 2,3,5,6-tetrafluorophenol (TFP) and conjugation of the reactive $^{186}$Re-MAG3-TFP ester to the MAb. After conjugation the $^{186}$Re-labeled MAb was purified on a PD10-column. After removal of unbound $^{186}$Re the radiochemical purity always exceeded 98%.

Binding-assay for radiolabeled antibodies. In vitro binding characteristics of the labeled MAbs used in the biodistribution and therapy studies were determined in an immunoreactivity assay essentially as described previously (Van Gog et al., 1997a). To test the binding of iodinated or $^{186}$Re-labeled MAbs, UM-SCC-11B cells fixed in 0.1% glutaraldehyde were used. UM-SCC-11B cells were kindly provided by Dr. T. E. Carey, University of Michigan, Ann Arbor, Minn. Five serial dilutions (ranging from 5×10$^6$ cells per tube to 3.1×10$^5$ cells per tube) were prepared with 1% BSA in PBS. Excess of unlabeled MAb IgG was added to a second tube with the lowest concentration of cells to determine non-specific binding. IgG labeled with 10,000 cpm of $^{125}$I, $^{131}$I or $^{186}$Re was added to each tube and the samples were incubated overnight at 4° C. Cells were spun down, radioactivity in the pellet and supernatant was measured in a gamma counter (LKB-Wallace 1282 CompuGamma, Kabi Pharmacia, Woerden, The Netherlands), and the percentage of bound and free radioactivity was calculated. Data were graphically analyzed in a modified Lineweaver Burk plot and the inmmunoreactivity was determined by linear extrapolation to conditions representing infinite antigen excess.

Biodistribution studies in HNSCC-bearing nude mice. For the biodistribution experiments nude mice bearing subcutaneously implanted human HNSCC xenografts (HNX-OE) were used as described previously (Van Gog et al., 1997a). Female mice (Hsd: Athymic nu/nu, 25–32 g, Harlan CPB, Zeist, The Netherlands) were 8–10 weeks old at the time of the experiments. Three biodistribution experiments were conducted with mice bearing 1 or 2 tumors ranging from 30 to 470 mm$^3$. In the first experiment, 10 $\mu$Ci (50 $\mu$g) $^{131}$I-labeled mMAb U36 were injected simultaneously with 10 $\mu$Ci (50 $\mu$g) $^{125}$I-labeled mMAb BIWA 1 in mice bearing tumors of 133±28 mm$^3$ (n=20 mice, 37 tumors). In the second experiment, 10 $\mu$Ci (50 $\mu$g) $^{131}$I-labeled hMAb BIWA 4 and 10 $\mu$Ci (50 $\mu$g) $^{125}$I-labeled cMAb BIWA 2 were co-injected in mice bearing tumors of 167±31 mm$^3$ (n=21 mice, 32 tumors). In the third experiment, 10 $\mu$Ci (50 $\mu$g) $^{131}$I-labeled hMAb BIWA 4 and 10 $\mu$Ci (50 $\mu$g) $^{125}$I-labeled hMAb BIWA 8 were co-injected in mice with tumors of 130±21 mm$^3$ (n=23 mice, 40 tumors). Conjugates were intravenously (i.v.) injected in a volume of 100 $\mu$l after dilution in 0.9% NaCl. To obtain a comparable blood/body clearance of the co-injected MAbs, only MAbs with an identical murine or human isotype were combined. The antibody dose (total dose 100 $\mu$g per mouse) was chosen high enough to prevent rapid isotype-related elimination of the MAb from the blood (Sharkey et al., 1991, Van Gog et al., 1997b), and low enough to prevent antigen saturation in the tumor.

At indicated time points after injection, mice were anaesthetized, bled, killed and dissected. Besides the tumors, the following organs were removed: liver, spleen, kidney, heart, stomach, ileum, colon, bladder, sternum, muscle, lung, skin and tongue. After weighing, radioactivity in tumors, blood and organs was counted in a dual-isotope gamma counter (LKB-Wallace 1282 CompuGamma), with automatic correction for the $^{131}$I-comptons in the $^{125}$I window setting. Radioactivity uptake in these tissues was calculated as the percentage of the injected dose per gram of tissue (% ID/g).

Until the day of MAb administration mice were routinely housed under specific-pathogen-free conditions, in sterile cages in a humidity- and temperature controlled clean room, classification 2000 according to the Federal Standard 209d. On the day of injection, mice were transported to a Radio Nuclide Center, and sterile radioimmunoconjugates were administered under aseptic conditions in a laminar flow hood.

Radioimmunotherapy studies in nude mice. Animal RIT studies were performed to compare the therapeutic efficacy of the different MAbs labeled with $^{186}$Re. The immunoreactive fractions of the conjugates always exceeded 75 %. Three therapy experiments were conducted with mice bearing 1 or 2 HNX-OE tumors ranging from 45 to 195 mm$^3$. The $^{186}$Re doses were chosen at the maximum tolerated dose (MTD) level (i.e. 400 $\mu$Ci) or lower (300 $\mu$Ci). The MTD level is defined as the dose resulting in 5–15% body weight loss. In the first experiment mice were given a single i.v. injection with either 300 $\mu$Ci (100 $\mu$g) $^{186}$Re-labeled mMAb U36 or 300 $\mu$Ci (100 $\mu$g) $^{186}$Re-labeled mMAb BIWA 1. In the second experiment either 300 $\mu$Ci (100 $\mu$g) $^{186}$Re-labeled hMAb BIWA 4 or 300 $\mu$Ci (100 $\mu$g) $^{186}$Re-labeled cMAb BIWA 2 were administered, and in the third experiment either 400 $\mu$Ci (100 $\mu$g) $^{186}$Re-labeled hMAb BIWA 4 or 400 $\mu$Ci (100 $\mu$g) $^{186}$Re-labeled hMAb BIWA 8. Average tumor volumes were similar for all experimental groups. Experiment 1: 95 mm$^3$±34 mm$^3$ (n=7 mice, 12 tumors) for the $^{186}$Re-mMAb U36 treated group, 91 mm$^3$±15 mm$^3$ (n=7 mice, 12 tumors) for the $^{186}$Re-mMAb BIWA 1 treated group, and 99 mm$^3$±54 mm$^3$ (n=6 mice, 11 tumors) for the control group. Experiment 2: 101 mm$^3$+35 mm$^3$ (n=7 mice, 12 tumors) for the $^{186}$Re-hMAb BIWA 4 treated group, 92 mm$^3$±43 mm$^3$ (n=7 mice, 12 tumors) for the $^{186}$Re-cMAb BIWA 2 treated group, while the control group was the same as in experiment 1. Experiment 3: 105 mm$^3$±43 mm$^3$ (n=8 mice, 13 tumors) for the $^{186}$Re-hMAb BIWA 4 treated group, 100 mm$^3$±42 mm$^3$ (n=8 mice, 13 tumors) for the $^{186}$Re-hMAb BIWA 8 treated group, and 110 mm$^3$±46 mm$^3$ (n=7 mice, 11 tumors) for the control group. During treatment tumors were measured twice weekly and tumor volumes relative to the volume at the start of treatment were calculated. Toxicity was monitored by measurement of the body weight twice weekly. Mice were sacrificed when one of the tumors exceeded 1000 mm$^3$.

Statistics. Differences in tissue uptake between co-injected MAbs were statistically analyzed for each time point with the Student's t-test for paired data. Differences in average tumor volume between the various RIT treatment groups were statistically analyzed for each time point with the Student's t-test for independent samples.

Results

In vitro binding characteristics of the CD44v6specific MAbs. The binding affinities of the five MAbs were analyzed using recombinant antigen as well as human tumor cell lines. Kinetic and affinity constants were evaluated by surface plasmon resonance using GST/CD44v3–v10 as immobilized antigen. Table 1 shows the association rates ($k_a$), dissociation rates ($k_d$) and dissociation constants ($K_d$). mMAb BIWA 1 and cMAb BIWA 2, containing identical variable regions, have similar $k_a$, $k_d$, and $K_d$ and show the highest affinity. In contrast, mMAb U36 and hMAb BIWA 4 have lower $k_a$ and higher $k_d$, resulting in markedly lower dissociation constants (factors 35.0 and 10.5, respectively). hMAb BIWA 8, containing murine residues in the light chain framework region 2, shows a marked decrease of $k_d$ resulting in increased affinity.

TABLE 1

Kinetics and affinity constants of MAbs directed against CD44v6.

| Antibody | $k_a$ ($M^{-1}s^{-1}$) | $k_d$ ($s^{-1}$) | $K_d$ (M) | $K_d$ relative to murine BIWA 1 |
|---|---|---|---|---|
| Murine BIWA 1 | $1.3 \times 10^5$ | $4.2 \times 10^{-5}$ | $3.2 \times 10^{-10}$ | 1.0 |
| Murine U36 | $1.5 \times 10^4$ | $1.7 \times 10^{-4}$ | $1.1 \times 10^{-8}$ | 35.0 |
| Chimeric BIWA 2 | $1.7 \times 10^5$ | $4.1 \times 10^{-5}$ | $2.4 \times 10^{-10}$ | 0.7 |
| Humanized BIWA 4 | $6.5 \times 10^4$ | $2.2 \times 10^{-4}$ | $3.4 \times 10^{-9}$ | 10.5 |
| Humanized BIWA 8 | $7.5 \times 10^4$ | $6.3 \times 10^{-5}$ | $8.4 \times 10^{-10}$ | 2.6 |

Figure 1:
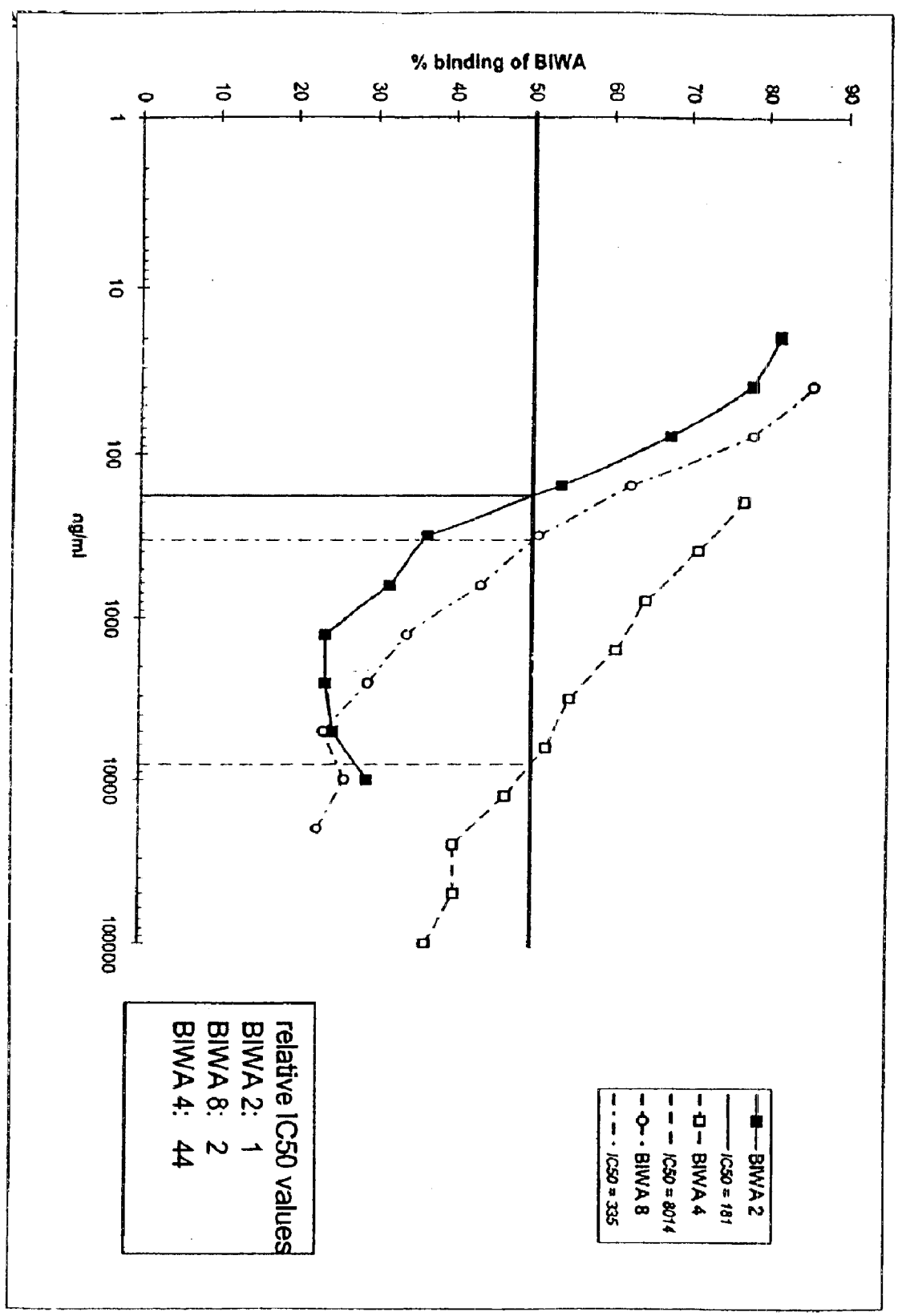
FIG. 1: Evaluation of relative binding affinities tested in a competitive cell ELISA.

The relative binding affinities of the cMAb and the hMAbs were also evaluated in a competitive cell ELISA using human A431 tumor cells (FIG. 1). In accordance with the affinity measurements on recombinant antigen, cMAb BIWA 2 was the most effective competitor, followed by hMAb BIWA 8 and hMAb BIWA 4. Similar results (not shown) were obtained with two other human HNSCC cell lines (FaDu and LICR-LON-HN5).

TABLE 2

Immunoreactive fraction of iodinated MAbs determined by binding to UM-SCC-11B cells.

| Experiment no. | Antibody | Label | Binding to $5 \times 10^6$ cells (%) | Binding Extrapolated[a] (%) |
|---|---|---|---|---|
| 1 | Murine U36 | $131_I$ | 59.7 | 87.4 |
|  | Murine BIWA 1 | $125_I$ | 91.1 | 91.1 |
| 2 | Humanized BIWA 4 | $131_I$ | 77.4 | 82.3 |
|  | Chimeric BIWA 2 | $125_I$ | 80.5 | 79.9 |
| 3 | Humanized BIWA 4 | $131_I$ | 77.3 | 74.5 |
|  | Humanized BIWA 8 | $125_I$ | 91.8 | 92.1 |

[a]Immunoreactivity was determined by linear extrapolation to conditions representing infinite antigen excess: see Materials and Methods The biodistributions in experiment 1 were determined at day 1, 2, 3 and 7 after injection; biodistributions in experiments 2 and 3 were determined at day 1, 2, 4 and 7 days after injection. The calculated average % ID/g of tumor and blood of all three experiments are given in Table 3.

TABLE 3

Tumor and blood levels of iodinated CD44v6-specific MAbs with different affinity after co-injection to HNX-OE bearing mice

| Exp. No. Blood | Time after injection | Conjugate A (% ID/g) | | Conjugate B (% ID/g) | | Conj. A.B ratio | |
|---|---|---|---|---|---|---|---|
| | | Tumor | Blood | Tumor | Blood | Tumor | Blood |
| 1. Conj. A:$^{131}$I-mMAb U36 | 1 d | 15.7 | 17.9 | 13.0 | 17.8 | 1.2 | 1.0 |
| Conj. B:$^{125}$I-mMAb BIWA 1 | 2 d | 18.4 | 15.0 | 13.4 | 14.9 | 1.4 | 1.0 |
| | 3 d | 20.6 | 11.8 | 13.7 | 11.0 | 1.5 | 1.1 |
| | 7 d | 16.5 | 7.1 | 7.8 | 4.8 | 2.1 | 1.5 |
| 2. Conj. A:$^{131}$I-hMAb BIWA 4 | 1 d | 10.8 | 10.2 | 9.1 | 10.6 | 1.2 | 1.0 |
| Conj. B:$^{125}$I-cMAb BIWA 2 | 2 d | 12.4 | 10.2 | 9.8 | 10.1 | 1.3 | 1.0 |
| | 4 d | 12.9 | 7.2 | 8.9 | 7.2 | 1.5 | 1.0 |
| | 7 d | 7.6 | 3.3 | 4.8 | 2.7 | 1.6 | 1.2 |
| 3. Conj. A:$^{131}$I-hMAb BIWA 4 | 1 d | 10.5 | 11.1 | 9.5 | 11.4 | 1.1 | 1.0 |
| Conj. B:$^{125}$I-hMAb BIWA 8 | 2 d | 10.9 | 10.0 | 9.6 | 9.8 | 1.1 | 1.0 |
| | 4 d | 11.7 | 6.2 | 9.6 | 5.9 | 1.2 | 1.0 |
| | 7 d | 10.1 | 4.2 | 7.8 | 3.9 | 1.3 | 1.1 |

Biodistribution in HNSCC-bearing nude mice. Biodistribution studies were performed in HNX-OE xenograft bearing nude mice. Two MAbs with identical murine or human isotype were labeled with either $^{125}$I or $^{131}$I and injected simultaneously (50 μg, 10 μCi each). Each pair of MAbs was selected to provide a stepwise decrease in the difference in affinities: mMAb U36 has a 35.0 fold lower affinity than mMAb BIWA 1 (experiment 1), hMAb BIWA 4 has a 14.0-fold lower affinity than cMAb BIWA 2 (experiment 2) and hMAb BIWA 4 has a 4.0-fold lower affinity than hMAb BIWA 8 (experiment 3). The immunoreactive fractions of all iodinated MAbs were at least 74% after extrapolation (Table 2).

For each pair of co-injected MAbs the uptake ratios for tumor and blood are provided. The average % ID/g and s.e.m. of tumor, blood and various organs at 3 (experiment 1) or 4 days p.i. (experiments 2 and 3) are shown in FIG. 2.

In a direct comparison of the two murine MAbs, tumor uptake of low affinity U36 was significantly higher than uptake of high affinity BIWA 1 at all time points (p<0.001) (Table 3). In contrast, no significant differences were found between the uptake values of these MAbs in blood and normal tissues at 1, 2 and 3 days p.i. At day 7 p.i., BIWA 1 levels in blood and most of the organs were significantly lower (p<0.05) than U36 levels, indicating more rapid clearance of BIWA 1 from the blood/body. A 50% higher tumor uptake of U36 in comparison with BIWA 1 at day 3 p.i. is illustrated by FIG. 2A.

Similar relationships were found in the evaluation of the two other MAb pairs. hMAb BIWA 4, while having the lower affinity, showed a significantly higher tumor uptake (p<0.001) than cMAb BIWA 2 and hMAb BIWA 8 at all time points (Table 3). In contrast, MAb levels in blood and normal tissues were similar for these pairs of MAbs at 1, 2, and 4 days p.i. At 7 days p.i., BIWA 2 and BIWA 8 levels in blood and most of the organs were significantly lower (p<0.05) than BIWA 4 levels, indicating more rapid clearance of these MAbs from the blood/body. A 45% higher tumor uptake of BIWA 4 in comparison with BIWA 2 is illustrated by FIG. 2B, while a 20% higher tumor uptake of BIWA 4 in comparison with BIWA 8 is illustrated by FIG. 2C, for the 4 days post injection time points.

Consistent results were obtained from an additional experiment (data not shown) in which the radiolabels were exchanged: $^{125}$I-BIWA 4 versus $^{131}$I-BIWA 8 instead of $^{131}$I-BIWA 4 versus $^{125}$I-BIWA 8. Data from this latter experiment rule out the possibility that the type of radiolabel had influenced the pharmacokinetic behavior of the labeled MAb.

Radioimmunotherapy in HNSCC-bearing nude mice. From the three biodistribution experiments it appeared that the low affinity MAbs showed a higher and more selective tumor uptake than the high affinity MAbs, and thus might be better suited for RIT. To test this possibility the following treatment groups were compared in RIT studies with HNX-OE xenograft bearing mice:

Experiment 1: 300 µCi $^{186}$Re-U36 or 300 µCi $^{186}$Re-BIWA 1 or saline as control. Experiment 2: 300 µCi $^{186}$Re-BIWA 4 or 300 µCi $^{186}$Re-BIWA 2 or saline as control. Experiment 3: 400 µCi $^{186}$Re-BIWA 4 or 400 µCi $^{186}$Re-BIWA 8 or saline as control.

In FIG. 3, the mean relative tumor volume (as a percentage of the tumor volume at day 0) for the control and treatment groups is plotted against time. Tumors of mice in the control group in all three experiments showed exponential growth with a tumor volume doubling time of about 7 days. In the groups treated with the $^{186}$Re-labeled MAbs, tumors stopped growing, in some cases accompanied by tumor regression, shortly after injection of the conjugates. However, all tumors ultimately regrew.

In experiment 1, administration of 300 µCi $^{186}$Re-BIWA 1 resulted in a decrease of the tumor growth rate, but not in a reduction of the mean tumor size. Administration of 300 µCi $^{186}$Re-U36, however, caused a reduction of the mean tumor volume from 185 mm³ to 120 mm³ between day 7 and day 17 post injection, after which tumors started growing again. The mean relative tumor volume in the $^{186}$Re-U36-treated group was significantly smaller (p<0.001) than that of the $^{186}$Re-BIWA 1 -treated group from day 14 on.

In experiment 2, administration of either 300 µCi $^{186}$Re-BIWA 4 or 300 µCi $^{186}$Re-BIWA 2 resulted in tumor growth arrest at day 7 with start of regrowth at day 17 p.i. BIWA 4 was more effective in RIT than BIWA 2 from day 14 on, but a significant difference between the mean relative tumor volumes was only found at day 14 p.i. (p<0.05).

In experiment 3, mice were treated with either 400 µCi $^{186}$Re-BIWA 4 or BIWA 8, which resulted in a decrease of the relative tumor volume to a minimum of 80±62 % and 98±81%, respectively, at day 19. Thereafter, tumors started regrowth.

These data indicate that the low affinity MAb BIWA 4 is more effective in RIT than the high affinity Mabs cBIWA 2 and BIWA 8.

References

Günthert, U., Hofmann, M., Rudy, W., Reber, S., Zöller, M., Haußmann, I., Matzku, S., Wenzel, A., Ponta, H., and Herrlich, P. A new variant of glycoprotein CD44 confers metastatic potential to rat carcinoma cells. Cell 65: 13–24 (1991).

Haisma, H. J., Hilgers, J., and Zurawski, V. R. Jr. Iodination of monoclonal antibodies for diagnosis and therapy using a convenient one vial method. J. Nucl. Med., 27: 1890–1895, 1986.

Heider, K.-H., Hofmann, M., Horst, E., van den Berg, F., Ponta, H., Herrlich, P., and Pals, S. T. A human homologue of the rat metastasis-associated variant of CD44 is expressed in colorectal carcinomas and adenomatous polyps. J. Cell Biol. 120: 227–233 (1993a).

Heider, K-H., Dämmrich, J., Skroch-Angel, P., Müller-Hermelink, H-K., Vollmers, H-P., Herrlich, P., and Ponta, H. Differential expression of CD44 splice variants in intestinal- and diffuse-type human gastric carcinomas and normal gastric mucosa. Cancer Res. 53: 4197–4203 (1993b).

Heider K H, Mulder J W R, Ostermann E, Susani S, Patzelt E, Pals S T, Adolf G R A. Splice variants of the cell surface glycoprotein CD44 associated with metastatic tumor cells are expressed in normal tissues of humans and cynomolgus monkeys. Eur. J. Cancer 31A: 2385–2391, 1995.

Heider K H, Sproll M, Susani S, Patzelt E, Beaumier P, Ostermann O, Ahorn H, Adolf G R A. Characterization of a high affinity monoclonal antibody specific for CD44v6 as candidate for immunotherapy of squamous cell carcinomas. Cancer Immunology Immunotherapy 43: 245–253, 1996.

Himmler, A., Maurer-Fogy, I., Kronke, M., Scheurich, P., Pfizenmaier, K., Lantz, M., Olsson, I., Hauptmann, R., Stratowa, C., and Adolf, G. R. Molecular cloning and expression of human and rat tumor necrosis factor receptor chain (p60) and its soluble derivative, tumor necrosis binding protein. DNA & Cell Biol., 9: 705–715, 1990.

Hofmann, M., Rudy, W., Zöller, M., Tölg, C., Ponta, H., Herrlich P., and Günthert, U. CD44 splice variants confer metastatic behavior in rats: homologous sequences are expressed in human tumor cell lines. Cancer Res. 51: 5292–5297 (1991).

Kugelman, L. C., Gangluly, S., Haggerty, J. G., Weissman, S. M., and Milstone, L. M. The core protein of epican, a heparan sulfate proteoglycan on keratinocytes, is an alternative form of CD44. J. Invest. Dermatol., 99: 886–891, 1992.

Koopman, G., Heider, K.-H., Horts, E., Adolf, G. R., van den Berg, F., Ponta, H., Herrlich, P., Pals, S. T. Activated human lymphocytes and aggressive Non-Hodgkin's lymphomas express a homologue of the rat metastasis-associated variant of CD44. J. Exp. Med. 177: 897–904 (1993).

Rudy, W., Hofmann, M., Schwartz-Albiez, R., Zöller, M., Heider, K.-H., Ponta, H., Herrlich, P. The two major CD44 proteins expressed on a metastatic rat tumor cell line are derived from different splice variants: Each one individually suffices to confer metastatic behaviour. Cancer Res. 53: 1262–1268 (1993).

Screaton, G. R., Bell, M. V., Jackson, D. G., Cornelis, F. B., Gerth, U., and Bell, J. I. Genomic structure of DNA encoding the lymphocyte homing receptor CD44 reveals at least 12 alternatively spliced exons. Proc. Natl. Acad. Sci. USA. 89: 12160–12164 (1992).

Sharkey, R. M., Natale, A., Goldenberg, D. M., and Mattes, M. J. Rapid blood clearance of immunoglobulin G2a and immunoglobulin G2b in nude mice. Cancer Res., 51: 3102–3107, 1991.

Tölg, C., Hofmann, M., Herrlich, P., and Ponta, H. Splicing choice from ten variant exons establishes CD44 variability. *Nucleic Acids. Res.* 21: 1225–1229 (1993).

Van Gog, F. B., Visser, G. W. M., Stroomer, J. W. G., Roos, J. C., Snow, G. B., and Van Dongen, G. A. M. S. High dose [186]Re-labeling of monoclonal antibodies for clinical application: pitfalls and solutions. Cancer, 80: 2360–2370, 1997a.

Van Gog, F. B., Brakenhoff, R. H., Snow, G. B., and Van Dongen, G. A. M. S. Rapid elimination of mouse/human chimeric monoclonal antibodies in nude mice. Cancer Immunol. Immunother., 44: 103–111, 1997b.

Wielenga, V. J. M., Heider, K.-H., Offerhaus, G. J. A., Adolf, G. R., van den Berg, F. M., Ponta, H., Herrlich, P., Pals, S. T. Expression of CD44 variant proteins in human colorectal cancer is related to tumor progression. *Cancer Res.* 53: 4754–4756 (1993).

Example 2

Details of Sequences

This example shows the details of sequences, e.g. the position of cloning sites, leaders and untranslated regions.

```
Abbreviations:
aa = amino acids
nt = nucleotide sequence

SEQ ID NO:1 VH BIWA 4/8 aa

EVQLVESGGGLVKPGGSLRLSCAASGFTFSSYDMSWVRQAPGKGLEW

VSTISSGGSYTYYLDSIKGRFTISRDNAKNSLYLQMNSLRAEDTAVYYC

ARQGLDYWGRGTLVTVSS

SEQ ID NO:2 VL BIWA 4 aa

EIVLTQSPATLSLSPGERATLSCSASSSINYIYWYQQKPGQAPRLLIYLTS

NLASGVPARFSGSGSGTDFTLTISSLEPEDFAVYYCLQWSSNPLTFGGG

TKVEIK

SEQ ID NO:3 VL BIWA 8 aa

EIVLTQSPATLSLSPGERATLSCSASSSINYIYWLQQKPGQAPRILIYLTS

NLASGVPARFSGSGSGTDFTLTISSLEPEDFAVYYCLQWSSNPLTFGGG

TKVEIK

SEQ ID NO:4 VH BIWA 4/8 nt

GAAGTGCAGCTGGTGGAGTCTGGGGGAGGCTTAGTGAAGCCTGGAGGGTCC

CTAAGACTCTCCTGTGCAGCCTCTGGATTCACTTTCAGTAGCTATGACATG

TCTTGGGTTCGCCAGGCTCCGGGGAAGGGGCTGGAGTGGGTCTCAACCATT

AGTAGTGGTGGTAGTTACACCTACTATCTAGACAGTATAAAGGGCCGATTC

ACCATCTCCAGAGACAATGCCAAGAACTCCCTGTACCTGCAAATGAACAGT

CTGAGGGCTGAGGACACGGCCGTGTATTACTGTGCAAGACAGGGGTTGGAC

TACTGGGGTCGAGGAACCTTAGTCACCGTCTCCTCA

SEQ ID NO:5 VL BIWA 4 nt

GAAATTGTTCTCACCCAGTCTCCAGCAACCCTGTCTCTGTCTCCAGGGGAG

AGGGCCACCCTGTCCTGCAGTGCCAGCTCAAGTATAAATTACATATACTGG
```
```
TACCAGCAGAAGCCAGGACAGGCTCCTAGACTCTTGATTTATCTCACATCC

AACCTGGCTTCTGGAGTCCCTGCGCGCTTCAGTGGCAGTGGGTCTGGAACC

GACTTCACTCTCACAATCAGCAGCCTGGAGCCTGAAGATTTTGCCGTTTAT

TACTGCCTGCAGTGGAGTAGTAACCCGCTCACATTCGGTGGTGGGACCAAG

GTGGAGATTAAA

SEQ ID NO:6 VL BIWA 8 nt

GAAATTGTTCTCACCCAGTCTCCAGCAACCCTGTCTCTGTCTCCAGGGGAG

AGGGCCACCCTGTCCTGCAGTGCCAGCTCAAGTATAAATTACATATACTGG

CTCCAGCAGAAGCCAGGACAGGCTCCTAGAATCTTGATTTATCTCACATCC

AACCTGGCTTCTGGAGTCCCTGCGCGCTTCAGTGGCAGTGGGTCTGGAACC

GACTTCACTCTCACAATCAGCAGCCTGGAGCCTGAAGATTTTGCCGTTTAT

TACTGCCTGCAGTGGAGTAGTAACCCGCTCACATTCGGTGGTGGGACCAAG

GTGGAGATTAAA

SEQ ID NO:7 heavy chain (variable + constant)
BIWA 4/8 aa

EVQLVESGGGLVKPGGSLRLSCAASGFTFSSYDMSWVRQAPGKGLEW

VSTISSGGSYTYYLDSIKGRFTISRDNAKNSLYLQMNSLRAEDTAVYYC

ARQGLDYWGRGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKA

KGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHN

HYTQKSLSLSPGK

SEQ ID NO:8 light chain (variable + constant)
BIWA 4 aa

EIVLTQSPATLSLSPGERATLSCSASSSINYIYWYQQKPGQAPRLLIYLTS

NLASGVPARFSGSGSGTDFTLTISSLEPEDFAVYYCLQWSSNPLTFGGG

TKVEIKRTVAAPSVFIFPPSDEQLKSGTASVVCLLNNFYPREAKVQWK

VDNALQSGNSQESVTEQDSKDSTYSLSSTLTLSKADYEKHKVYACEVT

HQGLSSPVTKSFNRGEC

SEQ ID NO:9 light chain (variable + constant)
BIWA 8 aa

EIVLTQSPATLSLSPGERATLSCSASSSINYIYWLQQKPGQAPRILIYLTS

NLASGVPARFSGSGSGTDFTLTISSLEPEDFAVYYCLQWSSNPLTFGGG

TKVEIKRTVAAPSVFIFPPSDEQLKSGTASVVCLLNNFYPREAKVQWK

VDNALQSGNSQESVTEQDSKDSTYSLSSTLTLSKADYEKHKVYACEVT

HQGLSSPVTKSFNRGEC

SEQ ID NO:10 heavy chain (variable + constant)
BIWA 4/8 nt; insert in pAD-CMV1/pAD-CMV19, contains
introns (lower case) between CH1-hinge, hinge-CH2,
CH2-CH3, leader sequence underlined, non-translated
sequences in italic, cloning sites bold
```

-continued aagctttgacagacgcacaaccctggactcccaagtctttctcttcagtga
caaacacagacataggatatcacatttgcttctgacacaactgtgttcact
agcagcctcaaacagacaccATGAACTTTGGGCT
CAGCTTGATTTTCCTTGTCCTAATTTTAAAAGGTGTCCAGTGTGAA
GTGCAGCTGGTGGAGTCTGGGGGAGGCTTAGTGAAGCCTGGAGGGTCCCTA
AGACTCTCCTGTGCAGCCTCTGGATTCACTTTCAGTAGCTATGACATGTCT
TGGGTTCGCCAGGCTCCGGGGAAGGGGCTGGAGTGGGTCTCAACCATTAGT
AGTGGTGGTAGTTACACCTACTATCTAGACAGTATAAAGGGCCGATTCACC
ATCTCCAGAGACAATGCCAAGAACTCCCTGTACCTGCAAATGAACAGTCTG
AGGGCTGAGGACACGGCCGTGTATTACTGTGCAAGACAGGGGTTGGACTAC
TGGGGTCGAGGAACCTTAGTCACCGTCTCCTCAGCTAGCACCAAGGGCCCA
TCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAAC
ACCAAGGTGGACAAGAAAGTTggtgagaggccagcacagggagggagggtg
tctgctggaagcaggctcagcgctcctgcctggacgcatcccggctatgca
gccccagtccagggcagcaaggcaggccccgtctgcctcttcacccggagc
ctctgccccgccccactcatgctcaggagagggtcttctggcttttttccca
ggctctgggcaggcacaggctaggtgcccctaacccaggccctgcacacaa
aggggcaggtgctgggctcagacctgccaagagccatatccgggaggaccc
tgccctgacctaagcccaccccaaaggccaaactctccactccctcagct
cggacaccttctctcctcccagattccagtaactcccaatcttctctctgc
aGAGCCCAAATCTTGTGACAAAACTCACACATGCCCACCGTGCCCAgtaa
gccagcccaggcctcgccctccagctcaaggcgggacaggtgccctagagt
agcctgcatccaggggacaggccccagccgggtgctgacacgtccacctcca
tctcttcctcaGCACCTGAACTCCTGGGGGGACCGTCAGTCTTCCTCTTCC
CCCCAAAACCCAAGGACACCCTCATGATCTCCCGGACCCCTGAGGTCACAT
GCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGC
AGTACAACAGCACGTACCGGGTGGTCAGCGTCCTCACCGTCCTGCACCAGG
ACTGGCTGAATGGCAAGGAGTACAAGTGCAAGGTCTCCAACAAAGCCCTCC
CAGCCCCCATCGAGAAAACCATCTCCAAAGCCAAAggtgggacccgtgggg
tgcgagggccacatggacagaggccggctcggcccacccctctgccctgaga
gtgaccgctgtaccaacctctgtcctacaGGGCAGCCCCGAGAACCACAGG
TGTACACCCTGCCCCCATCCCGGGATGAGCTGACCAAGAACCAGGTCAGCC
TGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGG -continued ACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGC
ACAACCACTACACGCAGAAGAGCCTCTCCCTGTCTCCGGGTAAATGAgtgc
gacggccgcgaa ttc

SEQ ID NO:11 light chain (variable + constant)
BIWA 4 nt; sequence in pAD-CMV1/pAD-CMV19, leader
sequence underlined, non-translated sequences in
italic, cloning sites bold aagcttgatcttcaggatatcacatttgcttct-
gacacaactgtgttcacta
gcaacctcaaacagacaccATGGATTTTCAGGTGCAGATTTTCAGCTTCCT
GCTAATGAGTGCCTCAGTCATAATGTCCAGGGGAGAAATTGTTCTCACCCA
GTCTCCAGCAACCCTGTCTCTGTCTCCAGGGGAGAGGGCCACCCTGTCCTG
CAGTGCCAGCTCAAGTATAAATTACATATACTGGTACCAGCAGAAGCCAGG
ACAGGCTCCTAGACTCTTGATTTATCTCACATCCAACCTGGCTTCTGGAGT
CCCTGCGCGCTTCAGTGGCAGTGGGTCTGGAACCGACTTCACTCTCACAAT
CAGCAGCCTGGAGCCTGAAGATTTTGCCGTTTATTACTGCCTGCAGTGGAG
TAGTAACCCGCTCACATTCGGTGGTGGGACCAAGGTGGAGATTAAACGGAC
TGTGGCTGCACCATCTGTCTTCATCTTCCCGCCATCTGATGAGCAGTTGAA
ATCTGGAACTGCTAGCGTTGTGTGCCTGCTGAATAACTTCTATCCCAGAGA
GGCCAAAGTACAGTGGAAGGTGGATAACGCCCTCCAATCGGGTAACTCCCA
GGAGAGTGTCACAGAGCAGGACAGCAAGGACAGCACCTACAGCCTCAGCAG
CACCCTGACGCTGAGCAAAGCAGACTACGAGAAACACAAAGTCTACGCCTG
CGAAGTCACCCATCAGGGCCTGAGCTCGCCCGTCACAAAGAGCTTCAACAG
GGGAGAGTGTTAGg aattc

SEQ ID NO:12 light chain (variable + constant)
BIWA 8 nt; sequence in pAD-CMV1/pAD-CMV19, leader
sequence underlined, non-translated sequences
italic, cloning sites bold aagcttgatcttcaggatatcacatttgcttctgacacaactgtgttcact
agcaacctcaaacagacaccATGGATTTTCAGGTGCAGATTTTCAGCTTCC
TGCTAATGAGTGCCTCAGTCATAATGTCCAGGGGAGAAATTGTTCTCACCC
AGTCTCCAGCAACCCTGTCTCTGTCTCCAGGGGAGAGGGCCACCCTGTCCT
GCAGTGCCAGCTCAAGTATAAATTACATATACTGGTCCAGCAGAAGCCAG
GACAGGCTCCTAGAATCTTGATTTATCTCACATCCAACCTGGCTTCTGGAG
TCCCTGCGCGCTTCAGTGGCAGTGGGTCTGGAACCGACTTCACTCTCACAA
TCAGCAGCCTGGAGCCTGAAGATTTTGCCGTTTATTACTGCCTGCAGTGGA
GTAGTAACCCGCTCACATTCGGTGGTGGGACCAAGGTGGAGATTAAACGGA
CTGTGGCTGCACCATCTGTCTTCATCTTCCCGCCATCTGATGAGCAGTTGA
AATCTGGAACTGCTAGCGTTGTGTGCCTGCTGAATAACTTCTATCCCAGAG
AGGCCAAAGTACAGTGGAAGGTGGATAACGCCCTCCAATCGGGTAACTCCC
AGGAGAGTGTCACAGAGCAGGACAGCAAGGACAGCACCTACAGCCTCAGCA
GCACCCTGACGCTGAGCAAAGCAGACTACGAGAAACACAAAGTCTACGCCT -continued
GCGAAGTCACCCATCAGGGCCTGAGCTCGCCCGTCACAAAGAGCTTCAACA GGGGAGAGTGTTAG*gaattc*

SEQ ID NO:13 heavy chain (variable + constant)
BIWA 4/8 nt; sequence in N5KG1val, no introns
contained, leader sequence underlined <u>ATGGAGTTTGGGCTGAGCTGGCTTTTTCTTGTGGCTATTTTAAAAGGTGTC</u>

<u>CAGTGT</u>GAAGTGCAGCTGGTGGAGTCTGGGGGAGGCTTAGTGAAGCCTGGA

GGGTCCCTAAGACTCTCCTGTGCAGCCTCTGGATTCACTTTCAGTAGCTAT

GACATGTCTTGGGTTCGCCAGGCTCCGGGGAAGGGGCTGGAGTGGGTCTCA

ACCATTAGTAGTGGTGGTAGTTACACCTACTATCTAGACAGTATAAAGGGC

CGATTCACCATCTCCAGAGACAATGCCAAGAACTCCCTGTACCTGCAAATG

AACAGTCTGAGGGCTGAGGACACGGCCGTGTATTACTGTGCAAGACAGGGG

TTGGACTACTGGGGTCGAGGAACCTTAGTCACCGTCTCCTCAGCTAGCACC

AAGGGCCCATCGGTCTTCCCCCTGGCACCCTCCTCCAAGAGCACCTCTGGG

GGCACAGCGGCCCTGGGCTGCCTGGTCAAGGACTACTTCCCCGAACCGGTG

ACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTG

CCCTCCAGCAGCTTGGGCACCCAGACCTACATCTGCAACGTGAATCACAAG

CCCAGCAACACCAAGGTGGACAAGAAAGTTGAGCCCAAATCTTGTGACAAA

ACTCACACATGCCCACCGTGCCCAGCACCTGAACTCCTGGGGGGACCGTCA

GTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAG

CCGCGGGAGGAGCAGTACAACAGCACGTACCGTGTGGTCAGCGTCCTCACC

GTCCTGCACCAGGACTGGCTGAATGGCAAGGAGTACAAGTGCAAGGTCTCC

AACAAAGCCCTCCCAGCCCCCATCGAGAAAACCATCTCCAAAGCCAAAGGG

CAGCCCCGAGAACCACAGGTGTACACCCTGCCCCCATCCCGGGATGAGCTG

ACCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAAG

CTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTG

TCTCCGGGTAAATGA

SEQ ID NO:14 light chain (variable + constant)
BIWA 4 nt; sequence in N5KG1val, leader sequence
underlined <u>ATGGAAGCCCCAGCTCAGCTTCTCTTCCTCCTGCTGCTCTGGCTCCCAGAT</u>

<u>ACCACCGGA</u>GAAATTGTTCTCACCCAGTCTCCAGCAACCCTGTCTCTGTCT

CCAGGGGAGAGGGCCACCCTGTCCTGCAGTGCCAGCTCAAGTATAAATTAC

ATATACTGGTACCAGCAGAAGCCAGGACAGGCTCCTAGACTCTTGATTTAT

CTCACATCCAACCTGGCTTCTGGAGTCCCTGCGCGCTTCAGTGGCAGTGGG

TCTGGAACCGACTTCACTCTCACAATCAGCAGCCTGGAGCCTGAAGATTTT

-continued
GCCGTTTATTACTGCCTGCAGTGGAGTAGTAACCCGCTCACATTCGGTGGT

GGGACCAAGGTGGAGATTAAACGTACGGTGGCTGCACCATCTGTCTTCATC

TTCCCGCCATCTGATGAGCAGTTGAAATCTGGAACTGCCTCTGTTGTGTGC

CTGCTGAATAACTTCTATCCCAGAGAGGCCAAAGTACAGTGGAAGGTGGAT

AACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGAC

TACGAGAAACACAAAGTCTACGCCTGCGAAGTCACCCATCAGGGCCTGAGC

TCGCCCGTCACAAAGAGCTTCAACAGGGGAGAGTGTTGA

SEQ ID NO:15 light chain (variable + constant)
BIWA 8 nt; sequence in N5KG1val, leader sequence
underlined <u>ATGGAAGCCCCAGCTCAGCTTCTCTTCCTCCTGCTGCTCTGGCTCCCAGAT</u>

<u>ACCACCGGA</u>GAAATTGTTCTCACCCAGTCTCCAGCAACCCTGTCTCTGTCT

CCAGGGGAGAGGGCCACCCTGTCCTGCAGTGCCAGCTCAAGTATAAATTAC

ATATACTGGCTCCAGCAGAAGCCAGGACAGGCTCCTAGAATCTTGATTTAT

CTCACATCCAACCTGGCTTCTGGAGTCCCTGCGCGCTTCAGTGGCAGTGGG

TCTGGAACCGACTTCACTCTCACAATCAGCAGCCTGGAGCCTGAAGATTTT

GCCGTTTATTACTGCCTGCAGTGGAGTAGTAACCCGCTCACATTCGGTGGT

GGGACCAAGGTGGAGATTAAACGTACGGTGGCTGCACCATCTGTCTTCATC

TTCCCGCCATCTGATGAGCAGTTGAAATCTGGAACTGCCTCTGTTGTGTGC

CTGCTGAATAACTTCTATCCCAGAGAGGCCAAAGTACAGTGGAAGGTGGAT

AACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGAC

TACGAGAAACACAAAGTCTACGCCTGCGAAGTCACCCATCAGGGCCTGAGC

TCGCCCGTCACAAAGAGCTTCAACAGGGGAGAGTGTTGA

SEQ ID NO:16 BIWA 4 in N5KG1val

CTGACGCGCCCTGTAGCGGCGCATTAAGCGCGGCGGGTGTGGTGGTTACGC

GCAGCGTGACCGCTACACTTGCCAGCGCCCTAGCGCCCGCTCCTTTCGCTT

TCTTCCCTTCCTTTCTCGCCACGTTCGCCGGCTTTCCCCGTCAAGCTCTAA

ATCGGGGGCTCCCTTTAGGGTTCCGATTTAGTGCTTTACGGCACCTCGACC

CCAAAAAACTTGATTAGGGTGATGGTTCACGTAGGGTCGCGACGTACCGGG

CCCCCCCTCGATTAATTAATCGAGCTACTAGCTTTGCTTCTCAATTTCTTA

TTTGCATAATGAGAAAAAAAGGAAAATTAATTTTAACACCAATTCAGTAGT

TGATTGAGCAAATGCGTTGCCAAAAAGGATGCTTTAGAGACAGTGTTCTCT

GCACAGATAAGGACAAACATTATTCAGAGGGAGTACCCAGAGCTGAGACTC

CTAAGCCAGTGAGTGGCACAGCATTCTAGGGAGAAATATGCTTGTCATCAC

CGAAGCCTGATTCCGTAGAGCCACACCTTGGTAAGGGCCAATCTGCTCACA

CAGGATAGAGAGGGCAGGAGCCAGGGCAGAGCATATAAGGTGAGGTAGGAT

CAGTTGCTCCTCACATTTGCTTCTGACATAGTTGTGCCAGCATGGAGGAAT

CGATCCTCCATGCTTGAACAAGATGGATTGCACGCAGGTTCTCCGGCCGCT

TGGGTGGAGAGGCTATTCGGCTATGACTGGGCACAACAGACAATCGGCTGC

-continued

```
TCTGATGCCGCCGTGTTCCGGCTGTCAGCGCAGGGGCGCCCGGTTCTTTTT
GTCAAGACCGACCTGTCCGGTGCCCTGAATGAACTGCAGGTAAGTGCGGCC
GCTCTAGGCCTCCAAAAAAGCCTCCTCACTACTTCTGGAATAGCTCAGAGG
CCGAGGCGGCCTCGGCCTCTGCATAAATAAAAAAAATTAGTCAGCCATGCA
TGGGGCGGAGAATGGGCGGAACTGGGCGGAGTTAGGGGCGGGATGGGCGGA
GTTAGGGGCGGGACTATGGTTGCTGACTAATTGAGATGCATGCTTTGCATA
CTTCTGCCTGCTGGGGAGCCTGGGGACTTTCCACACCTGGTTGCTGACTAA
TTGAGATGCATGCTTTGCATACTTCTGCCTGCTGGGGAGCCTGGGGACTTT
CCACACCCTAACTGACACACATTCCACAGAATTAATTCCCCTAGTTATTAA
TAGTAATCAATTACGGGGTCATTAGTTCATAGCCCATATATGGAGTTCCGC
GTTACATAACTTACGGTAAATGGCCCGCCTGGCTGACCGCCCAACGACCCC
CGCCCATTGACGTCAATAATGACGTATGTTCCCATAGTAACGCCAATAGGG
ACTTTCCATTGACGTCAATGGGTGGACTATTTACGGTAAACTGCCCACTTG
GCAGTACATCAAGTGTATCATATGCCAAGTACGCCCCCTATTGACGTCAAT
GACGGTAAATGGCCCGCCTGGCATTATGCCCAGTACATGACCTTATGGGAC
TTTCCTACTTGGCAGTACATCTACGTATTAGTCATCGCTATTACCATGGTG
ATGCGGTTTTGGCAGTACATCAATGGGCGTGGATAGCGGTTTGACTCACGG
GGATTTCCAAGTCTCCACCCCATTGACGTCAATGGGAGTTTGTTTTGGCAC
CAAAATCAACGGGACTTTCCAAAATGTCGTAACAACTCCGCCCCATTGACG
CAAATGGGCGGTAGGCGTGTACGGTGGGAGGTCTATATAAGCAGAGCTGGG
TACGTGAACCGTCAGATCGCCTGGAGACGCCATCACAGATCTCTCACCATG
GAAGCCCCAGCTCAGCTTCTCTTCCTCCTGCTGCTCTGGCTCCCAGATACC
ACCGGAGAAATTGTTCTCACCCAGTCTCCAGCAACCCTGTCTCTGTCTCCA
GGGGAGAGGGCCACCCTGTCCTGCAGTGCCAGCTCAAGTATAAATTACATA
TACTGGTACCAGCAGAAGCCAGGACAGGCTCCTAGACTCTTGATTTATCTC
ACATCCAACCTGGCTTCTGGAGTCCCTGCGCGCTTCAGTGGCAGTGGGTCT
GGAACCGACTTCACTCTCACAATCAGCAGCCTGGAGCCTGAAGATTTTGCC
GTTTATTACTGCCTGCAGTGGAGTAGTAACCCGCTCACATTCGGTGGTGGG
ACCAAGGTGGAGATTAAACGTACGGTGGCTGCACCATCTGTCTTCATCTTC
CCGCCATCTGATGAGCAGTTGAAATCTGGAACTGCCTCTGTTGTGTGCCTG
CTGAATAACTTCTATCCCAGAGAGGCCAAAGTACAGTGGAAGGTGGATAAC
GCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTAC
GAGAAACACAAAGTCTACGCCTGCGAAGTCAC
CCATCAGGGCCTGAGCTCGCCCGTCACAAAGAGCTTCAACAGGGGAGAGTG
TTGAATTCAGATCCGTTAACGGTTACCAACTACCTAGACTGGATTCGTGAC
AACATGCGGCCGTGATATCTACGTATGATCAGCCTCGACTGTGCCTTCTAG
TTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAG
CAAGGGGGAGGATTGGGAAGACAATAGCAGGCATGCTGGGGATGCGGTGGG
CTCTATGGAACCAGCTGGGACTAGTAGCTTTGCTTCTCAATTTCTTATTTG
CATAATGAGAAAAAAGGAAAATTAATTTTAACACCAATTCAGTAGTTGAT
TGAGCAAATGCGTTGCCAAAAAGGATGCTTTAGAGACAGTGTTCTCTGCAC
AGATAAGGACAAACATTATTCAGAGGGAGTACCCAGAGCTGAGACTCCTAA
GCCAGTGAGTGGCACAGCATTCTAGGGAGAAATATGCTTGTCATCACCGAA
GCCTGATTCCGTAGAGCCACACCTTGGTAAGGGCCAATCTGCTCACACAGG
ATAGAGAGGGCAGGAGCCAGGGCAGAGCATATAAGGTGAGGTAGGATCAGT
TGCTCCTCACATTTGCTTCTGACATAGTTGTGTTGGGAGCTTGGATAGCTT
GGACAGCTCAGGGCTGCGATTTCGCGCCAAACTTGACGGCAATCCTAGCGT
GAAGGCTGGTAGGATTTTATCCCCGCTGCCATCATGGTTCGACCATTGAAC
TGCATCGTCGCCGTGTCCCAAAATATGGGGATTGGCAAGAACGGAGACCTA
CCCTGGCCTCCGCTCAGGAACGAGTTCAAGTACTTCCAAAGAATGACCACA
ACCTCTTCAGTGGAAGGTAAACAGAATCTGGTGATTATGGGTAGGAAAACC
TGGTTCTCCATTCCTGAGAAGAATCGACCTTTAAAGGACAGAATTAATATA
GTTCTCAGTAGAGAACTCAAAGAACCACCACGAGGAGCTCATTTTCTTGCC
AAAAGTTTGGATGATGCCTTAAGACTTATTGAACAACCGGAATTGGCAAGT
AAAGTAGACATGGTTTGGATAGTCGGAGGCAGTTCTGTTTACCAGGAAGCC
ATGAATCAACCAGGCCACCTTAGACTCTTTGTGACAAGGATCATGCAGGAA
TTTGAAAGTGACACGTTTTTCCCAGAAATTGATTTGGGGAAATATAAACTT
CTCCCAGAATACCCAGGCGTCCTCTCTGAGGTCCAGGAGGAAAAAGGCATC
AAGTATAAGTTTGAAGTCTACGAGAAGAAAGACTAACAGGAAGATGCTTTC
AAGTTCTCTGCTCCCCTCCTAAAGCTATGCATTTTTATAAGACCATGGGAC
TTTTGCTGGCTTTAGATCAGCCTCGACTGTGCCTTCTAGTTGCCAGCCATC
TGTTGTTTGCCCCTCCCCCGTGCCTTCCTTGACCCTGGAAGGTGCCACTCC
CACTGTCCTTTCCTAATAAAATGAGGAAATTGCATCGCATTGTCTGAGTAG
GTGTCATTCTATTCTGGGGGGTGGGGTGGGCAGGACAGCAAGGGGGAGGA
TTGGGAAGACAATAGCAGGCATGCTGGGGATGCGGTGGGCTCTATGGAACC
AGCTGGGGCTCGAAGCGGCCGCTCCGGATATGCCAAGTACGCCCCCTATTG
ACGTCAATGACGGTAAATGGCCCGCCTGGCATTATGCCCAGTACATGACCT
TATGGGACTTTCCTACTTGGCAGTACATCTACGTATTAGTCATCGCTATTA
CCATGGTGATGCGGTTTTGGCAGTACATCAATGGGCGTGGATAGCGGTTTG
ACTCACGGGGATTTCCAAGTCTCCACCCCATTGACGTCAATGGGAGTTTGT
TTTGGCACCAAAATCAACGGGACTTTCCAAAATGTCGTAACAACTCCGCCC
CATTGACGCAAATGGGCGGTAGGCGTGTACGGTGGGAGGTCTATATAAGCA
CAGCTGGGTACGTCCTCACATTCAGTGATCAGCACTGAACACAGACCCGTC
GACATGAGTTTGGGCTGAGCTGGCTTTTTCTTGTGGCTATTTTAAAAGGT
GTCCAGTGTGAAGTGCAGCTGGTGGAGTCTGGGGGAGGCTTAGTGAAGCCT
GGAGGGTCCCTAAGACTCTCCTGTGCAGCCTCTGGATTCACTTTCAGTAGC
TATGACATGTCTTGGGTTCGCCAGGCTCCGGGGAAGGGGCTGGAGTGGGTC
```

-continued

```
TCAACCATTAGTAGTGGTGGTAGTTACACCTACTATCTAGACAGTATAAAG
GGCCGATTCACCATCTCCAGAGACAATGCCAAGAACTCCCTGTACCTGCAA
ATGAACAGTCTGAGGGCTGAGGACACGGCCGT
GTATTACTGTGCAAGACAGGGGTTGGACTACTGGGGTCGAGGAACCTTAGT
CACCGTCTCCTCAGCTAGCACCAAGGGCCCATCGGTCTTCCCCCTGGCACC
CTCCTCCAAGAGCACCTCTGGGGGCACAGCGGCCCTGGGCTGCCTGGTCAA
GGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTC
CCTCAGCAGCGTGGTGACCGTGCCCTCCAGCAGCTTGGGCACCCAGACCTA
CATCTGCAACGTGAATCACAAGCCCAGCAACACCAAGGTGGACAAGAAAGT
TGAGCCCAAATCTTGTGACAAAACTCACACATGCCCACCGTGCCCAGCACC
TGAACTCCTGGGGGACCGTCAGTCTTCCTCTTCCCCCCAAAACCCAAGGA
CACCCTCATGATCTCCCGGACCCCTGAGGTCACATGCGTGGTGGTGGACGT
GAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAA
AACCATCTCCAAAGCCAAAGGGCAGCCCCGAGAACCACAGGTGTACACCCT
GCCCCCATCCCGGGATGAGCTGACCAAGAACCAGGTCAGCCTGACCTGCCT
GGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGG
CTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTA
CACGCAGAAGAGCCTCTCCCTGTCTCCGGGTAAATGAGGATCCGTTAACGG
TTACCAACTACCTAGACTGGATTCGTGACAACATGCGGCCGTGATATCTAC
GTATGATCAGCCTCGACTGTGCCTTCTAGTTGCCAGCCATCTGTTGTTTGC
CCCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGAC
AATAGCAGGCATGCTGGGGATGCGGTGGGCTCTATGGAACCAGCTGGGGCT
CGACAGCGCTGCGATCGCCTCGAGGCCGCTACTAACTCTCTCCTCCCTCCT
TTTTCCTGCAGGACGAGGCAGCGCGGCTATCGTGGCTGGCCACGACGGGCG
TTCCTTGCGCAGCTGTGCTCGACGTTGTCACTGAAGCGGGAAGGGACTGGC
TGCTATTGGGCGAAGTGCCGGGGCAGGATCTCCTGTCATCTCACCTTGCTC
CTGCCGAGAAAGTATCCATCATGGCTGATGCAATGCGGCGGCTGCATACGC
TTGATCCGGCTACCTGCCCATTCGACCACCAAGCGAAACATCGCATCGAGC
GAGCACGTACTCGGATGGAAGCCGGTCTTGTCGATCAGGATGATCTGGACG
AAGAGCATCAGGGGCTCGCGCCAGCCGAACTGTTCGCCAGGCTCAAGGCGC
GCATGCCCGACGGCGAGGATCTCGTCGTGACCCATGGCGATGCCTGCTTGC
CGAATATCATGGTGGAAAATGGCCGCTTTTCTGGATTCATCGACTGTGGCC
```

```
GGCTGGGTGTGGCGGACCGCTATCAGGACATAGCGTTGGCTACCCGTGATA
TTGCTGAAGAGCTTGGCGGCGAATGGGCTGACCGCTTCCTCGTGCTTTACG
GTATCGCCGCTCCCGATTCGCAGCGCATCGCCTTCTATCGCCTTCTTGACG
AGTTCTTCTGAGCGGGACTCTGGGGTTCGAAATGACCGACCAAGCGACGCC
CAACCTGCCATCACGAGATTTCGATTCCACCGCCGCCTTCTATGAAAGGTT
GGGCTTCGGAATCGTTTTCCGGGACGCCGGCTGGATGATCCTCCAGCGCGG
GGATCTCATGCTGGAGTTCTTCGCCCACCCCAACTTGTTTATTGCAGCTTA
TAATGGTTACAAATAAAGCAATAGCATCACAAATTTCACAAATAAAGCATT
TTTTTCACTGCATTCTAGTTGTGGTTTGTCCAAACTCATCAATCTATCTTA
TCATGTCTGGATCGCGGCCGGCCGCACCGCGGTGGAGCTTTAATTAAGGCG
CGCCAGCTCCAGCTTTTGTTCCCTTTAGTGAGGGTTAATTTCGAGCTTGGC
GTAATCATGGTCATAGCTGTTTCCTGTGTGAA
ATTGTTATCCGCTCACAATTCCACACAACATACGAGCCGGAAGCATAAAG
TGTAAAGCCTGGGGTGCCTAATGAGTGAGCTAACTCACATTAATTGCGTTG
CGCTCACTGCCCGCTTTCCAGTCGGGAAACCTGTCGTGCCAGCTGCATTAA
TGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGAC
TTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAAC
TCACGTTAAGGGATTTTGGTCATGAGATTATCAAAAAGGATCTTCACCTAG
ATCCTTTTAAATTAAAAATGAAGTTTTAAATCAATCTAAAGTATATATGAG
TAAACTTGGTCTGACAGTTACCAATGCTTAATCAGTGAGGCACCTATCTCA
GCGATCTGTCTATTTCGTTCATCCATAGTTGCCTGACTCCCCGTCGTGTAG
ATAACTACGATACGGGAGGGCTTACCATCTGGCCCCAGTGCTGCAATGATA
CCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAAT
```

AGTTTGCGCAACGTTGTTGCCATTGCTACAGGCATCGTGGTGTCACGCTCG

TCGTTTGGTATGGCTTCATTCAGCTCCGGTTCCCAACGATCAAGGCGATTT

ACATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGCA

GCACTGCATAATTCTCTTACTGTCATGCCATCCGTAAGATGCTTTTCTGTG

ACTGGTGAGTACTCAACCAAGTCATTCTGAGAATAGTGTATGCGGCGACCG

AGTTGCTCTTGCCCGGCGTCAATACGGGATAATACCGCGCCACATAGCAGA

ACTTTAAAAGTGCTCATCATTGGAAAACGTTCTTCGGGGCGAAAACTCTCA

AGGATCTTACCGCTGTTGAGATCCAGTTCGATGTAACCCACTCGTGCACCC

AACTGATCTTCAGCATCTTTTACTTTCACCAGCGTTTCTGGGTGAGCAAAA

ACAGGAAGGCAAAATGCCGCAAAAAAGGGAATAAGGGCGACACGGAAATGT

TGAATACTCATACTCTTCCTTTTTCAATATTATTGAAGCATTTATCAGGGT

TATTGTCTCATGAGCGGATACATATTTGAATGTATTTAGAAAAATAAACAA

ATAGGGGTTCCGCGCACATTTCCCCGAAAAGTGCCACA

SEQ ID NO:17 pAD-CMV1, cloning sites in bold

TCGACATTGATTATTGACTAGTTATTAATAGTAATCAATTACGGGGT

CATTAGTTCATAGCCCATATATGGAGTTCCGCGTTACATAACTTAC

GGTAAATGGCCCGCCTGGCTGACCGCCCAACGACCCCCGCCCATTG

ACGTCAATAATGACGTATGTTCCCATAGTAACGCCAATAGGGACTT

TCCATTGACGTCAATGGGTGGAGTATTTACGGTAAACTGCCCACTT

GGCAGTACATCAAGTGTATCATATGCCAAGTACGCCCCCTATTGAC

GTCAATGACGGTAAATGGCCCGCCTGGCATTATGCCCAGTACATGA

CCTTATGGGACTTTCCTACTTGGCAGTACATCTACGTATTAGTCATC

GCTATTACCATGGTGATGCGGTTTTGGCAGTACATCAATGGGCGTG

GATAGCGGTTTGACTCACGGGGATTTCCAAGTCTCCACCCCATTGA

CGTCAATGGGAGTTTGTTTTGGCACCAAAATCAACGGGACTTTCCA

AAATGTCGTAACAACTCCGCCCCATTGACGCAAATGGGCGGTAGGC

GTGTACGGTGGGAGGTCTATATAAGCAGAGCTCTCTGGCTAACTAG

AGAACCCACTGCTTAACTGGCTTATCGAAATTAATACGACTCACTA

TAGGGAGACCCAAGCTTCTGCAGGTCGACATCGATGGATCCGGTA

CCTCGAGCGCGAATTCTCTAGAGGATCTTTGTGAAGGAACCTTACT

TCTGTGGTGTGACATAATTGGACAAACTACCTACAGAGATTTAAAG

CTCTAAGGTAAATATAAAATTTTTAAGTGTATAATGTGTTAAACTA

CTGATTCTAATTGTTTGTGTATTTTAGATTCCAACCTATGGAACTGA

TGAATGGGAGCAGTGGTGGAATGCCTTTAATGAGGAAAACCTGTTT

TGCTCAGAAGAAATGCCATCTAGTGATGATGAGGCTACTGCTGACT

CTCAACATTCTACTCCTCCAAAAAAGAAGAGAAAGGTAGAAGACC

CCAAGGACTTTCCTTCAGAATTGCTAAGTTTTTTGAGTCATGCTGTG

TTTAGTAATAGAACTCTTGCTTGCTTTGCTATTTACACCACAAAGGA

AAAAGCTGCACTGCTATACAAGAAAATTATGGAAAAATATTTGATG

TATAGTGCCTTGACTAGAGATCATAATCAGCCATACCACATTTGTA

GAGGTTTTACTTGCTTTAAAAAACCTCCCACACCTCCCCCTGAACCT

GAAACATAAAATGAATGCAATTGTTGTTGTTAACTTGTTTATTGCA

GCTTATAATGGTTACAAATAAAGCAATAGCATCACAAATTTCACAA

ATAAAGCATTTTTTTCACTGCATTCTAGTTGTGGTTTGTCCAAACTC

ATCAATGTATCTTATCATGTCTGGATCAATTCTGAGAAACTAGCCTT

AAAGACAGACAGCTTTGTTCTAGTCAGCCAGGCAAGCATATGTAAA

TAAAGTTCTCAGGGAACTGAGGTTAAAAGATGTATCCTGGACCTG

CCAGACCTGGCCATTCACGTAAACAGAAGATTCCGCCTCAAGTTCC

GGTTAACAACAGGAGGCAACGAGATCTCAAATCTATTACTTCTAAT

CGGGTAATTAAAACCTTTCAACTAAAACACGGACCCACGGATGTCA

CCCACTTTTCCTTCCCGGCTCCGCCCTTCTCAGTACTCCCCACCAT

TAGGCTCGCTACTCCACCTCCACTTCCGGGCGCGACACCCACGTGC

CCTCTCCCACCCGACGCTAACCCCGCCCCTGCCCGTCTGACCCCGC

CCACCACCTGGCCCCGCCCCGTTGAGGACAGAAGAAACCCCGGGC

AGCCGCAGCCAAGGCGGACGGGTAGACGCTGGGGGCGCTGAGGAG

TCGTCCTCTACCTTCTCTGCTGGCTCGGTGGGGACGCGGTGGATCT

CAGGCTTCCGGAAGACTGGAAGAACCGGCTCAGAACCGCTTGTCTC

CGCGGGGCTTGGGCGGCGGAAGAATGGCCGCTAGACGCGGACTTG

GTGCGAGGCATCGCAGGATGCAGAAGAGCAAGCCCGCCGGGAGCG

CGCGGCTGTACTACCCCGCGCCTGGAGCGGCCACGCCGGACTGGG

CGGGGCCGGCCTGGTGGAGGCGGAGTCTGACCTCGTGGAGGCGGG

GCCTCTGATGTTCAAATAGGATGCTAGGCTTGTTGAGGCGTGGCCT

CCGATTCACAAGTGGGAAGCAGCGCCGGGCGACTGCAATTTCGCG

CCAAACTTGGGGGAAGCACAGCGTACAGGCTGCCTAGGTGATCGC

TGCTGCTGTCATGGTTCGACCGCTGAACTGCATCGTCGCCGTGTCCC

AGAATATGGGCATCGGCAAGAACGGAGACCTTCCCTGGCCAATGC

TCAGGTACTGGCTGGATTGGGTTAGGGAAACCGAGGCGGTTCGCTG

AATCGGGTCGAGCACTTGGCGGAGACGCGCGGGCCAACTACTTAG

GGACAGTCATGAGGGGTAGGCCCGCCGGCTGCTGCCCTTGCCCATG

CCCGCGGTGATCCCCATGCTGTGCCAGCCTTTGCCCAGAGGCGCTC

TAGCTGGGAGCAAAGTCCGGTCACTGGGCAGCACCACCCCCGGA

CTTGCATGGGTAGCCGCTGAGATGGAGCCTGAGCACACGTGACAG

GGTCCCTGTTAACGCAGTGTTTCTCTAACTTTCAGGAACGAGTTCA

AGTACTTCCAAAGAATGACCACCACCTCCTCAGTGGAAGGTAAACA

GAACCTGGTGATTATGGGCCGGAAAACCTGGTTCTCCATTCCTGAG

AAGAATCGACCTTTAAAGGACAGAATTAATATAGTTCTCAGTAGAG

AGCTCAAGGAACCACCACAAGGAGCTCATTTTCTTGCCAAAAGTCT

GGACCATGCCTTAAAACTTATTGAACAACCAGAGTTAGCAGATAAA

GTGGACATGGTTTGGATAGTTGGAGGCAGTTCCGTTTACAAGGAAG

-continued

CCATGAATCAGCCAGGCCATCTCAGACTCTTTGTGACAAGGATCAT
GCAGGAATTTGAAAGTGACACGTTCTTCCCAGAAATTGATTTGGAG
AAATATAAACTTCTCCCAGAGTACCCAGGGGTCCTTTCTGAAGTCC
AGGAGGAAAAAGGCATCAAGTATAAATTTGAAGTCTATGAGAAGA
AAGGCTAACAGAAAGATACTTGCTGATTGACTTCAAGTTCTACTGC
TTTCCTCCTAAAATTATGCATTTTTACAAGACCATGGGACTTGTGTT
GGCTTTAGATCCTGTGCATCCTGGGCAACTGTTGTACTCTAAGCCA
CTCCCCAAAGTCATGCCCCAGCCCCTGTATAATTCTAAACAATTAG
AATTATTTTCATTTTCATTAGTCTAACCAGGTTATATTAAATATACT
TTAAGAAACACCATTTGCCATAAAGTTCTCAATGCCCCTCCCATGC
AGCCTCAAGTGGCTCCCCAGCAGATGCATAGGGTAGTGTGTGTACA
AGAGACCCCAAAGACATAGAGCCCCTGAGAGCATGAGCTGATTATG
GGGGCTCATAGAGATAGGAGCTAGATGAATAAGTACAAAGGGCAG
AAATGGGTTTTAACCAGCAGAGCTAGAACTCAGACTTTAAAGAAA
ATTAGATCAAAGTAGAGACTGAATTATTCTGCACATCAGACTCTGA
GCAGAGTTCTGTTCACTCAGACAGAAAATGGGTAAATTGAGAGCTG
GCTCCATTGTGCTCCTTAGAGATGGGAGCAGGTGGAGGATTATATA
AGGTCTGGAACATTTAACTTCTCCGTTTCTCATCTTCAGTGAGATTC
CAAGGGATACTACAATTCTGTGGAATGTGTGTCAGTTAGGGTGTGG
AAAGTCCCCAGGCTCCCCAGCAGGCAGAAGTATGCAAAGCATGCA
TCTCAATTAGTCAGCAACCAGGTGTGGAAAGTCCCCAGGCTCCCCA
GCAGGCAGAAGTATGCAAAGCATGCATCTCAATTAGTCAGCAACC
ATAGTCCCGCCCCTAACTCCGCCCATCCCGCCCCTAACTCCGCCCA
GTTCCGCCCATTCTCCGCCCCATGGCTGACTAATTTTTTTATTTAT
GCAGAGGCCGAGGCGCCTCTGAGCTATTCCAGAAGTAGTGAGGAG
GCTTTTTTGGAGGCCTAGGCTTTTGCAAAAAAGCTAATTCAGCCTG
AATGGCGAATGGGACGCGCCCTGTAGCGGCGCATTAAGCGCGGCG
GGTGTGGTGGTTACGCGCAGCGTGACCGCTACACTTGCCAGCGCCC
TAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTC
CGATTTAGTGCTTTACGGCACCTCGACCCCAAAAACTTGATTAGGG
TGATGGTTCACGTAGTGGGCCATCGCCCTGATAGACGGTTTTTCGC
CCTTTGACGTTGGAGTCCACGTTCTTTAATAGTGGACTCTTGTTCCA
AACTGGAACAACACTCAACCCTATCTCGGTCTATTCTTTTGATTTAT
AAGGGATTTTGCCGATTTCGGCCTATTGGTTAAAAAATGAGCTGAT
TTAACAAAAATTTAACGCGAATTTTAACAAAATATTAACGTTTACA
ATTTCAGGTGGCACTTTTCGGGGAAATGTGCGCGGAACCCCTATTT
GTTTATTTTTCTAAATACATTCAAATATGTATCCGCTCATGAGACAA
TAACCCTGATAAATGCTTCAATAATATTGAAAAAGGAAGAGTATGA
GTATTCAACATTTCCGTGTCGCCCTTATTCCCTTTTTTGCGGCATTTT

-continued

GCCTTCCTGTTTTTGCTCACCCAGAAACGCTGGTGAAAGTAAAAGA
TGCTGAAGATCAGTTGGGTGCACGAGTGGGTTACATCGAACTGGAT
CTCAACAGCGGTAAGATCCTTGAGAGTTTTCGCCCCGAAGAACGTT
TTCCAATGATGAGCACTTTTAAAGTTCTGCTATGTGGCGCGGTATTA
TCCCGTATTGACGCCGGGCAAGAGCAACTCGGTCGCCGCATACACT
ATTCTCAGAATGACTTGGTTGAGTACTCACCAGTCACAGAAAAGCA
TCTTACGGATGGCATGACAGTAAGAGAATTATGCAGTGCTGCCATA
ACCATGAGTGATAACACTGCGGCCAACTTACTTCTGACAACGATCG
GAGGACCGAAGGAGCTAACCGCTTTTTTGCACAACATGGGGGATC
ATGTAACTCGCCTTGATCGTTGGGAACCGGAGCTGAATGAAGCCAT
ACCAAACGACGAGCGTGACACCACGATGCCTGTAGCAATGGCAAC
AACGTTGCGCAAACTATTAACTGGCGAACTACTTACTCTAGCTTCC
CGGCAACAATTAATAGACTGGATGGAGGCGGATAAAGTTGCAGGA
CCACTTCTGCGCTCGGCCCTTCCGGCTGGCTGGTTTATTGCTGATAA
ATCTGGAGCCGGTGAGCGTGGGTCTCGCGGTATCATTGCAGCACTG
GGGCCAGATGGTAAGCCCTCCCGTATCGTAGTTATCTACACGACGG
GGAGTCAGGCAACTATGATGAACGAAATAGACAGATCGCTGAGA
TAGGTGCCTCACTGATTAAGCATTGGTAACTGTCAGACCAAGTTTA
CTCATATATACTTTAGATTGATTTAAAACTTCATTTTTAATTTAAAA
GGATCTAGGTGAAGATCCTTTTTGATAATCTCATGACCAAAATCCC
TTAACGTGAGTTTTCGTTCCACTGAGCGTCAGACCCCGTAGAAAAG
ATCAAAGGATCTTCTTGAGATCCTTTTTTTCTGCGCGTAATCTGCTG
CTTGCAAACAAAAAAACCACCGCTACCAGCGGTGGTTTGTTTGCCG
GATCAAGAGCTACCAACTCTTTTTCCGAAGGTAACTGGCTTCAGCA
GAGCGCAGATACCAAATACTGTCCTTCTAGTGTAGCCGTAGTTAGG
CCACCACTTCAAGAACTCTGTAGCACCGCCTACATACCTCGCTCTG
CTAATCCTGTTACCAGTGGCTGCTGCCAGTGGCGATAAGTCGTGTC
TTACCGGGTTGGACTCAAGACGATAGTTACCGGATAAGGCGCAGC
GGTCGGGCTGAACGGGGGGTTCGTGCACACAGCCCAGCTTGGAGC
GAACGACCTACACCGAACTGAGATACCTACAGCGTGAGCATTGAG
AAAGCGCCACGCTTCCCGAAGGGAGAAAGGCGGACAGGTATCCGG
TAAGCGGCAGGGTCGGAACAGGAGAGCGCACGAGGGAGCTTCCAG
GGGGAAACGCCTGGTATCTTTATAGTCCTGTCGGGTTTCGCCACCT
CTGACTTGAGCGTCGATTTTTGTGATGCTCGTCAGGGGGCGGAGC
CTATGGAAAAACGCCAGCAACGCC

SEQ ID NO:18 pAD-CMV19, cloning sites in bold

TCGACATTGATTATTGACTAGTTATTAATAGTAATCAATTACGGGGT
CATTAGTTCATAGCCCATATATGGAGTTCCGCGTTACATAACTTAC
GGTAAATGGCCCGCCTGGCTGACCGCCCAACGACCCCCGCCCATTG
ACGTCAATAATGACGTATGTTCCCATAGTAACGCCAATAGGGACTT

-continued

TCCATTGACGTCAATGGGTGGAGTATTTACGGTAAACTGCCCACTT
GGCAGTACATCAAGTGTATCATATGCCAAGTACGCCCCTATTGAC
GTCAATGACGGTAAATGGCCCGCCTGGCATTATGCCCAGTACATGA
CCTTATGGGACTTTCCTACTTGGCAGTACATCTACGTATTAGTCATC
GCTATTACCATGGTGATGCGGTTTTGGCAGTACATCAATGGGCGTG
GATAGCGGTTTGACTCACGGGGATTTCCAAGTCTCCACCCCATTGA
CGTCAATGGGAGTTTGTTTTGGCACCAAAATCAACGGGACTTTCCA
AAATGTCGTAACAACTCCGCCCCATTGACGCAAATGGGCGGTAGGC
GTGTACGGTGGGAGGTCTATATAAGCAGAGCTCGTTTAGTGAACCG
TCAGATCGCCTGGAGACGCCATCCACGCTGTTTTGACCTCCATAGA
AGACACCGGACCGATCCAGCCTCCGCGGCCGGGAACGGTGCATT
GGAACGCGGATTCCCCGTGCCAAGAGTCAGGTAAGTACCGCCTATA
GAGAAGACTCTTGGGTTTCTGATAGGCACTGACTCTCTCTGCCTATT
GGTCTATTTTCCCACCCTTAGGCTGCTGGTGCTTAACTGGCTTATCG
AAATTAATACGACTCACTATAGGGAGACCCAAGCTTCTGCAGGTC
GACATCGATGGATCCGGTACCTCGAGCGCGAATTCTCTAGAGATAT
CTTGTTTATTGCAGCTTATAATGGTTACAAATAAAGCAATAGCATC
ACAAATTTCACAAATAAAGCATTTTTTCACTGCATTCTAGTTGTGG
TTTGTCCAAACTCATCAATGTATCTTATCATGTCTGGATCAATTCTG
AAAAACTAGCCTTAAAGACAGACAGCTTTGTTCTAGTCAGCCAGGC
AAGCATATGTAAATAAAGTTCCTCAGGGAACTGAGGTTAAAAGAT
GTATCCTGGACCTGCCAGACCTGGCCATTCACGTAAACAGAAGATT
CCGCCTCAAGTTCCGGTTAACAACAGGAGGCAACGAGATCTCAAAT
CTATTACTTCTAATCGGGTAATTAAAACCTTTCAACTAAAACACGG
ACCCACGGATGTCACCCACTTTTCCTTCCCCGGCTCCGCCCTTCTCA
GTACTCCCCACCATTAGGCTCGCTACTCCACCTCCACTTCCGGGCG
CGACACCCACGTGCCCTCTCCCACCCGACGCTAACCCCGCCCCTGC
CCGTCTGACCCCGCCCACCACCTGGCCCCGCCCCGTTGAGGACAGA
AGAAACCCCGGGCAGCCGCAGCCAAGGCGGACGGGTAGACGCTGG
GGGCGCTGAGGAGTCGTCCTCTACCTTCTCTGCTGGCTCGGTGGGG
GACGCGGTGGATCTCAGGCTTCCGGAAGACTGGAAGAACCGGCTC
AGAACCGCTTGTCTCCGCGGGCTTGGGCGGCGGAAGAATGGCCG
CTAGACGCGGACTTGGTGCGAGGCATCGCAGGATGCAGAAGAGCA
AGCCCGCCGGGAGCGCGCGGCTGTACTACCCCGCGCCTGGAGCGG
CCACGCCGGACTGGGCGGGGCCGGCCTGGTGGAGGCGGAGTCTGA
CCTCGTGGAGGCGGGGCCTCTGATGTTCAAATAGGATGCTAGGCTT
GTTGAGGCGTGGCCTCCGATTCACAAGTGGGAAGCAGCGCCGGGC
GACTGCAATTTCGCGCCAAACTTGGGGGAAGCACAGCGTACAGGC
TGCCTAGGTGATCGCTGCTGCTGTCATGGTTCGACCGCTGAACTGC
ATCGTCGCCGTGTCCCAGAATATGGGCATCGGCAAGAACGGAGAC

-continued

CTTCCCTGGCCAATGCTCAGGTACTGGCTGGATTGGGTTAGGGAAA
CCGAGGCGGTTCGCTGAATCGGGTCGAGCACTTGGCGGAGACGCG
CGGGCCAACTACTTAGGGACAGTCATGAGGGGTAGGCCCGCCGGC
TGCTGCCCTTGCCCATGCCCGCGGTGATCCCCATGCTGTGCCAGCC
TTTGCCCAGAGGCGCTCTAGCTGGGAGCAAAGTCCGGTCACTGGGC
AGCACCACCCCCGGACTTGCATGGGTAGCCGCTGAGATGGAGCCT
GAGCACACGTGACAGGGTCCCTGTTAACGCAGTGTTTCTCTAACTT
TCAGGAACGAGTTCAAGTACTTCCAAAGAATGACCACCACCTCCTC
AGTGGAAGGTAAACAGAACCTGGTGATTATGGGCCGGAAAACCTG
GTTCTCCATTCCTGAGAAGAATCGACCTTTAAAGGACAGAATTAAT
ATAGTTCTCAGTAGAGAGCTCAAGGAACCACCACAAGGAGCTCATT
TTCTTGCCAAAAGTCTGGACCATGCCTTAAAACTTATTGAACAACC
AGAGTTAGCAGATAAAGTGGACATGGTTTGGATAGTTGGAGGCAG
TTCCGTTTACAAGGAAGCCATGAATCAGCCAGGCCATCTCAGACTC
TTTGTGACAAGGATCATGCAGGAATTTGAAAGTGACACGTTCTTCC
CAGAAATTGATTTGGAGAAATATAAACTTCTCCCAGAGTACCCAGG
GGTCCTTTCTGAAGTCCAGGAGGAAAAAGGCATCAAGTATAAATTT
GAAGTCTATGAGAAGAAAGGCTAACAGAAAGATACTTGCTGATTG
ACTTCAAGTTCTACTGCTTTCCTCCTAAAATTATGCATTTTTACAAG
ACCATGGGACTTGTGTTGGCTTTAGATCCTGTGCATCCTGGGCAAC
TGTTGTACTCTAAGCCACTCCCCAAAGTCATGCCCCAGCCCCTGTA
TAATTCTAAACAATTAGAATTATTTTCATTTTCATTAGTCTAACCAG
GTTATATTAAATATACTTTAAGAAACACCATTTGCCATAAAGTTCTC
AATGCCCCTCCCATGCAGCCTCAAGTGGCTCCCCAGCAGATGCATA
GGGTAGTGTGTGTACAAGAGACCCCAAAGACATAGAGCCCCTGAG
AGCATGAGCTGATATGGGGGCTCATAGAGATAGGAGCTAGATGAA
TAAGTACAAAGGGCAGAAATGGGTTTTAACCAGCAGAGCTAGAAC
TCAGACTTTAAAGAAAATTAGATCAAAGTAGAGACTGAATTATTCT
GCACATCAGACTCTGAGCAGAGTTCTGTTCACTCAGACAGAAAATG
GGTAAATTGAGAGCTGGCTCCATTGTGCTCCTTAGAGATGGGAGCA
GGTGGAGGATTATATAAGGTCTGGAACATTTAACTTCTCCGTTTCTC
ATCTTCAGTGAGATTCCAAGGGATACTACAATTCTGTGGAATGTGT
GTCAGTTAGGGTGTGGAAAGTCCCCAGGCTCCCCAGCAGGCAGAA
GTATGCAAAGCATGCATCTCAATTAGTCAGCAACCAGGTGTGGAAA
GTCCCCAGGCTCCCCAGCAGGCAGAAGTATGCAAAGCATGCATCTC
AATTAGTCAGCAACCATAGTCCCGCCCCTAACTCCGCCCATCCCGC
CCCTAACTCCGCCCAGTTCCGCCCATTCTCCGCCCCATGGCTGACTA
ATTTTTTTTATTTATGCAGAGGCCGAGGCGCCTCTGAGCTATTCCAG
AAGTAGTGAGGAGGCTTTTTTGGAGGCCTAGGCTTTTGCAAAAAAG
CTAATTCAGCCTGAATGGCGAATGGGAAATTGTAAACGTTAATATT

-continued

TTGTTAAAATTCGCGTTAAATTTTTGTTAAATCAGCTCATTTTTTAA

CCAATAGGCCGAAATCGGCAAAATCCCTTATAAATCAAAAGAATA

GACCGAGATAGGGTTGAGTGTTGTTCCAGTTTGGAACAAGAGTCCA

CTATTAAAGAACGTGGACTCCAACGTCAAAGGGCGAAAAACCGTC

TATCAGGGCGATGGCCCACTACGTGAACCATCACCCTAATCAAGTT

TTTGGGGTCGAGGTGCCGTAAAGCACTAAATCGGAACCCTAAAGG

GAGCCCCCGATTTAGAGCTTGACGGGGAAAGCCGGCGAACGTGGC

GAGAAAGGAAGGGAAGAAAGCGAAAGGAGCGGGCGCTAGGGCGC

TGGCAAGTGTAGCGGTCACGCTGCGCGTAACCACCACACCCGCCGC

GCTTAATGCGCCGCTACAGGGCGCGTCAGGTGGCACTTTTCGGGA

AATGTGCGCGGAACCCCTATTTGTTTATTTTTCTAAATACATTCAAA

TATGTATCCGCTCATGAGACAATAACCCTGATAAATGCTTCAATAA

TATTGAAAAAGGAAGAGTATGAGTATTCAACATTTCCGTGTCGCCC

TTATTCCCTTTTTTGCGGCATTTTGCCTTCCTGTTTTGCTCACCCAG

AAACGCTGGTGAAAGTAAAAGATGCTGAAGATCAGTTGGGTGCAC

GAGTGGGTTACATCGAACTGGATCTCAACAGCGGTAAGATCCTTGA

GAGTTTTCGCCCCGAAGAACGTTTTCCAATGATGAGCACTTTTAAA

GTTCTGCTATGTGGCGCGGTATTATCCCGTATTGACGCCGGGCAAG

AGCAACTCGGTCGCCGCATACACTATTCTCAGAATGACTTGGTTGA

GTACTCACCAGTCACAGAAAAGCATCTTACGGATGGCATGACAGTA

AGAGAATTATGCAGTGCTGCCATAACCATGAGTGATAACACTGCGG

CCAACTTACTTCTGACAACGATCGGAGGACCGAAGGAGCTAACCG

CTTTTTTGCACAACATGGGGGATCATGTAACTCGCCTTGATCGTTGG

GAACCGGAGCTGAATGAAGCCATACCAAACGACGAGCGTGACACC

ACGATGCCTGTAGCAATGGCAACAACGTTGCGCAAACTATTAACTG

GCGAACTACTTACTCTAGCTTCCCGGCAACAATTAATAGACTGGAT

GGAGGCGGATAAAGTTGCAGGACCACTTCTGCGCTCGGCCCTTCCG

GCTGGCTGGTTTATTGCTGATAAATCTGGAGCCGGTGAGCGTGGGT

CTCGCGGTATCATTGCAGCACTGGGGCCAGATGGTAAGCCCTCCCG

TATCGTAGTTATCTACACGACGGGGAGTCAGGCAACTATGGATGAA

CGAAATAGACAGATCGCTGAGATAGGTGCCTCACTGATTAAGCATT

GGTAACTGTCAGACCAAGTTTACTCATATATACTTTAGATTGATTTA

AAACTTCATTTTTAATTTAAAAGGATCTAGGTGAAGATCCTTTTTGA

TAATCTCATGACCAAAATCCCTTAACGTGAGTTTTCGTTCCACTGAG

CGTCAGACCCCGTAGAAAAGATCAAAGGATCTTCTTGAGATCCTTT

TTTTCTGCGCGTAATCTGCTGCTTGCAAACAAAAAAACCACCGCTA

CCAGCGGTGGTTTGTTTGCCGGATCAAGAGCTACCAACTCTTTTTCC

GAAGGTAACTGGCTTCAGCAGAGCGCAGATACCAAATACTGTCCTT

CTAGTGTAGCCGTAGTTAGGCCACCACTTCAAGAACTCTGTAGCAC

CGCCTACATACCTCGCTCTGCTAATCCTGTTACCAGTGGCTGCTGCC

-continued

AGTGGCGATAAGTCGTGTCTTACCGGGTTGGACTCAAGACGATAGT

TACCGGATAAGGCGCAGCGGTCGGGCTGAACGGGGGGTTCGTGCA

CACAGCCCAGCTTGGAGCGAACGACCTACACCGAACTGAGATACC

TACAGCGTGAGCATTGAGAAAGCGCCACGCTTCCCGAAGGGAGAA

AGGCGGACAGGTATCCGGTAAGCGGCAGGGTCGGAACAGGAGAGC

GCACGAGGGAGCTTCCAGGGGGAAACGCCTGGTATCTTTATAGTCC

TGTCGGGTTTCGCCACCTCTGACTTGAGCGTCGATTTTTGTGATGCT

CGTCAGGGGGCGGAGCCTATGGAAAAACGCCAGCAACGCAGCTG

C

Example 3

Clinical Study 1170.1

List of Abbreviations and Definition of Terms

| | |
|---|---|
| ADCC | Antibody Dependent Cell-mediated Cytotoxicity |
| AE | Adverse Event |
| ALT | Alanine Amino Transferase |
| a.p. | Anterior posterior |
| AP | Alkaline phosphatase |
| AST | Aspartate Amino Transferase |
| AUC | Area Under the concentration-time Curve |
| Bq | Becquerel, SI unit for radioactivity Becquerel (1 Bq = one decay/s) |
| BSA | Bovine Serum Albumin |
| CD44v6 | CD44 variant isoform v6 |
| CDS | Corporate Drug Safety |
| cGy | Centi Gray measure for radioactivity |
| CHO | Chinese Hamster Ovary cells |
| Ci | Curie; unit for radioactivity; 1 Ci = 37 × 10$^9$ decays/s = 37 GBq |
| CL | Total body clearance |
| cMAb | Chimeric Monoclonal Antibody |
| cm | Centimetre |
| $C_{max}$ | Maximum drug concentration observed |
| cpm | Count per minute |
| CRF | Case Report/Record Form |
| CT (scan) | Computed Tomography |
| CTC | Common Toxicity Criteria |
| CV | Coefficient of Variation |
| DLT | Dose Limiting Toxicity |
| ECG | Electrocardiogram |
| ELISA | Enzyme-Linked Immuno-Sorbent Assay |
| ENT | Ear Nose Throat |
| f | Female |
| FDA | Food and Drug Administration |
| g | Gram |
| GBq | SI unit for radioactivity Giga Becquerel (1 GBq = 10$^9$ decays/s) |
| GCP | Good Clinical Practice |
| GGT | Gamma Glutaryl Transpeptidase |
| GMP | Good Manufacturing Practice |
| Gy | Gray |
| HAHA | Human-Anti-Human-Antibody |
| Hb | Haemoglobin |
| HER2 | Human Epidermal growth factor Receptor 2 |
| hMAb | Humanised Monoclonal Antibody |
| HNSCC | Head and Neck Squamous Cell Carcinoma |
| HPLC | High Performance Liquid Chromatography |
| hr/h | Hour |
| hrs | Hours |
| Ht | Haematocrit |
| $^{131}$I | Iodine-131 (half-life 8.05 days) |
| ICH | International committee on harmonisation |
| ID | Injected Dose |
| IEC | Independent Ethics Committee |

-continued

| | |
|---|---|
| IgG | Immunoglobulin G |
| INN | International Non proprietary Name |
| IRB | Institutional Review Board |
| ITT | Intent-To-Treat |
| i.v. | Intravenous(ly) |
| KeV | Kilo electron volt |
| 1/L | Litre |
| m | Male |
| $m^2$ | Square metres |
| MAb | Monoclonal Antibody |
| MAG2GABA- | Mercaptoacetylglycylglycyl-gamma-aminobutyrate-tetrafluorophenol |
| TFP | ester (MAG2GABA-TFP), chelate used for coupling $^{186}$Re to monoclonal antibodies (future method) |
| MAG3 | Mercaptoacetyltriglycine. Chelate used for coupling of $^{99m}$Tc and $^{186}$Re to monoclonal antibodies |
| MBq | SI unit for radioactivity; Mega Becquerel (1 MBq = $10^6$ decays/s) |
| mCi | Milli Curie; unit for radioactivity; 1 mCi = 37 million decays/s = 37 MBq |
| MCV | Mean Corpuscular Volume |
| mGy | Milli Gray |
| µg | Microgram |
| mg | Milligram |
| min | Minute |
| ml/mL | Millilitre |
| mMAb | Murine Monoclonal Antibody |
| mmHg | Millimetre mercury |
| µmol | Micromol |
| mmol | Millimol |
| MRI | Magnetic Resonance Imaging |
| MRT | Mean Residence Time |
| mSv | Milli Sievert |
| MTD | Maximum Tolerated Dose |
| NA/n.a. | Not Applicable |
| NCI | U.S. National Cancer Institute |
| ND | Not Done |
| ng | Nanogram |
| No/N | Number |
| nos | Not other specified |
| NSCLC | Non Small Cell Lung Cancer |
| n.y.r. | Not yet recovered |
| p.a. | Posterior anterior |
| PBS | Phosphate Buffered Saline |
| p.i. | Post infusion |
| p.o. | Per os |
| PP | Per Protocol |
| Pt./Pat | Patient |
| Pts. | Patients |
| $^{186}$Re | Rhenium-186, radionuclide; half-life of 3.7 days (tissue penetration of β-particles of about 1.2 mm) |
| Recov. | Recovered |
| RES | Reticulo Endothelial System |
| RIS | Radioimmunoscintigraphy |
| RIT | Radioimmunotherapy |
| ROI | Region of Interest |
| SAE | Serious Adverse Event |
| SCC | Squamous Cell Carcinoma |
| sCD44v6 | Soluble CD44v6 |
| SD | Stable Disease |
| sGOT | Serum Glutamic Oxalacetic Transaminase |
| sGPT | Serum Glutamic Pyruvic Transaminase |
| SOC | System Organ Class |
| SOP | Standard Operating Procedure |
| SPECT | Single Photon Emission Computed Tomography |
| t½ | Elimination half life |
| $^{99m}$Tc | Technetium 99 m (half-life 6 hours) |
| TLC | Thin Layer Chromatography |
| $T_{max}$ | Time point at which the maximum drug concentration is observed |
| TNM | Tumour Node Metastasis system for staging tumours |
| TSH | Thyroid Stimulating Hormone |
| UICC | Union Internationale Contre le Cancer (international union against cancer) |
| unk | Unknown |
| $V_{ss}$ | Apparent volume of distribution under steady-state conditions |
| $V_z$ | Apparent volume of distribution during the terminal phase |

-continued

| | |
|---|---|
| WBC | White Blood Count |
| WHO | World Health Organisation |

Study Objectives

General Aim/Clinical Objective

The general aim of the present study was to assess the safety and tolerability of intravenously administered $^{99m}$Tc and $^{186}$Re-label led hMAb BIWA 4, to confirm preferential accumulation in the tumour of $^{99m}$Tc-labelled hMAb BIWA 4, to determnine the maximum tolerated radiation dose of $^{186}$Re-labelled hMAb BIWA 4 and to propose a safe dose for phase II development. In order to reach this goal the study was divided into two parts:

Part A: Objectives

To determine the safety and tolerability of a single infusion of intravenously administered $^{99m}$Tc-labelled hMAb BIWA 4 in patients with advanced squamous cell carcinoma of the head and neck.

To determine the biodistribution of a single infusion of $^{99m}$Tc-labelled hMAb BIWA 4 at different BIWA 4 dose levels in patients with advanced squamous cell carcinoma of the head and neck.

To study the pharmacokinetics of a single infusion of $^{99m}$Tc-labelled hMAb BIWA 4.

Part B: Objectives

To determine the qualitative and quantitative toxic effects of $^{186}$Re-labelled hMAb BIWA 4 and to study the predictability, onset, duration, intensity, reversibility and dose-relationship of the toxic side effects.

To determine the maximum tolerated radiation dose of intravenously administered $^{186}$Re-labelled hMAb BIWA 4 in head and neck cancer patients.

To study the pharmacokinetics of intravenously administered $^{186}$Re-labelled hMAb BIWA 4 in patients with squamous cell carcinoma of the head and neck.

A secondary objective was to determine the preliminary therapeutic effects of $^{186}$Re-labelled hMAb BIWA 4.

The following objectives outlined in the protocol could not be addressed during the performance of the trial. The development of the programme with the linker chelate mercaptoacetyltriglycine (MAG3), used for coupling of $^{99m}$Tc and $^{186}$Re to monoclonal antibodies was discontinued and thus the trial was finished. The further development with BIWA 4 will continue by using the linker mercaptoacetylglycylglycyl-gamma-aminobutyrate-tetrafluorophenol ester (MAG2GABA-TFP).

The MID for single dose treatment was to be identified first before more patients were entered to define the MTD for a second treatment with $^{186}$Re-labelled hMAb BIWA 4.

To propose a safe dose for first and consecutive infusions with $^{186}$Re-labelled hMAb BIWA 4 for further studies.

To obtain initial results on a dose schedule for repeated dosing.

Primary Variables

Safety: clinical laboratory tests, human-anti-human-antibody (HAHA) assessments, vital signs measurements and adverse events.

Efficacy: biopsy biodistribution data (Part A only) and radioimmunoscintigraphic images (Part A and B including dosimetry for Part B of the trial).

Pharmnacokinetic results.

Secondary Variables

A secondary variable for the study was tumour response (Part B only).

Investigational Plan

Overall Study Design and Plan—Description

The trial was performed in two parts. Part A evaluated the optimal dose of cold BIWA 4 and quantified tumour uptake while Part B investigated the maximum tolerated dose of $^{186}$Re-BIWA 4.

Part A:

This part of the clinical trial was an uncontrolled, rising dose sequential group study. It was designed to provide initial data on the safety and tolerability of a single infusion of $^{99m}$Tc-labelled hMAb BIWA 4, to investigate the pattern and level of biodistribution and to establish the pharmacokinetic profile of hMAb BIWA 4 in patients with head and neck cancer. Three protein doses of hMAb BIWA 4 were used in this Part A of the study with three patients planned to be treated at each dose level.

Patients were routinely investigated by the Department of Otolaryngology to determine the extent of the tumour. This included physical (examination, computed tomography (CT) or MRI scans of the head and neck and panendoscopy (optional). During these procedures samples of tissues, suspect of tumour, were taken and investigated for the presence of squamous cell carcinoma. Based on the results of these investigations, the patients were destined to undergo surgery including neck dissection.

Radiolabelled antibody was injected and the patient was observed for occurrence of adverse events. Radioimnmunoscintigraphic scans were performed 21 hours post infusion (p.i.) prior to surgery. Patients underwent surgery 48 hours (hrs) after the infusion of the radioactively labelled hMAb BIWA 4. The pathologist investigated the neck dissection specimen to determine the exact tumour load. Moreover, the amount of $^{99m}$Tc in biopsies from tumour site(s) and normal tissues in the surgical specimen was measured. Tumour sites and tumour infiltrated nodes were examined for the presence of CD44v6 antigen by immunohistochemical techniques. The first three patients were administered 2 mg hMAb BIWA 4 labelled with 20 mCi $^{99m}$Tc combined with 23 mg unlabelled hMAb BIWA 4. The second group of three evaluable patients was administered 2 mg hMAb BIWA 4 labelled with 20 mCi $^{99m}$Tc combined with 48 mg unlabelled hMAb BIWA 4 and the third group was administered 2 mg of the labelled antibody combined with 98 mg of unlabelled antibody.

Pharmacokinetic assessments were done at the specified timepoints.

Part B

This part of the clinical trial was an open uncontrolled, dose escalation study. It was designed to assess the safety and tolerability of $^{186}$Re-labelled hMAb BIWA 4, to determine the maximum tolerated dose (MTD) of intravenously administered $^{186}$Re-labelled hMAb BIWA 4 and to determine the preliminary therapeutic effects of $^{186}$Re-labelled hMAb BIWA 4 in head and neck cancer patients for whom no curative options were available. In addition the pharmacokinetic profile of $^{186}$Re-labelled hMAb BIWA 4 was assessed.

All patients entering into this part of the trial received the dose of hMAb BIWA 4, which was selected basing on the results of Part A of the study. The hMAb BIWA 4 was labelled with escalating doses of $^{186}$Re. At the lower dose levels (toxicity observed did not exceed grade 1) two patients were entered per dose group and at the higher levels ($\geq$ grade 2 toxicity) a minimum of three patients were entered per dose group. All patients were evaluated to determine the safety of the administered hMAb BIWA 4.

Patients were routinely investigated by the Department of Otolaryngology to determine the extent of the tumour. This included physical examination and CT or MRI scanning of tumour locations.

$^{186}$Re-labelled antibody was injected with escalating radiation doses: patients in the first dose group received a radiation dose of 20 mCi/m$^2$, after which the dose for patients in the subsequent dose groups was escalated by 10 mCi/m$^2$ increments until the MTD was reached. Patients were observed for occurrence of adverse events. Radioimmunoscintigraphic scans were performed.

Study Procedures at Each Visit

Visit Schedule

Screening Visit

Before entry into the study each patient was screened for eligibility. Demographics and medically relevant history were recorded, concomitant therapy was recorded and a general physical examination was done and the body weight was measured. The Karnofsky performance score was determined. Written informed consent had to be obtained. A pregnancy test was required for women with childbearing potential. A 12-lead electrocardiogram (ECG) was made and blood as well as urine safety laboratory assessments were done. A blood sample for HAHA-testing was also taken. A Chest X-ray was made and a full disease assessment (CT/MRI, ear-nose-throat [ENT] examination) was performed.

At the end of this visit the results of the required investigations were evaluated, the inclusion and exclusion criteria verified and arrangements for surgery (Part A only) were made.

Visit 2: Study Days 1–7

Parts A and B:

On the first study day, which was not more than 3 weeks after the screening visit, the patient was admitted to the hospital. All required baseline laboratory assessments not obtained at the screening visit had to be done and evaluated prior to the infusion and the eligibility criteria had to be met. The body weight was measured. All concomitant therapy had to be recorded. Every adverse event starting after the signing of the written informed consent had to be recorded in the patient file and the case report form (CRF).

On the day of treatment, before antibody administration a blood sample was collected for pharmacokinetics (including the assessment of soluble CD44v6) and the vital signs were recorded. Urine was collected firom 0–4 hrs, 4–8 hrs, 8–12 hrs and 12–24 hrs during the first 24 hrs and then in 24 hrs intervals up to 48 and 96 hrs post infusion for Part A and B, respectively.

The antibody was administered at the department of Nuclear Medicine or in a designated room in the hospital. The antibody had to be administered through a peripheral upper extremity vein as proximally as possible. In all cases, the infusion was given over 5 minutes, after a 10-mL saline flush, through a freely flowing line. In order to obtain reproducible pharmacokinetic results a syringe pump had to be used. Therefore, dilution of the volume with NaCl 0.9 % was required to 20 mL. This antibody infusion was followed by a 10 mL saline flush. Any suspected extravasation was documented in the CRF and the patient was imaged.

An emergency unit available with resuscitation equipment, anti-histamines, corticosteroids and epinephrine was within reach to counteract possible anaphylaxis. Adverse events and changes in the concomitant therapy were recorded daily.

Part A

Vital signs were recorded at 10, 60 and 120 minutes p.i. Blood samples for safety and soluble CD44v6 were collected 21, 48 and 144 hrs post infusion.

Blood samples for pharmacokinetics were drawn at the end of the infusion and at 5, 10, 30 minutes and 1, 2, 4, 16, 21, 48, 72 hrs after the end of the infusion, and on day 7 (144-hrs p.i. including a serum sample for HAHA and soluble CD44v6 assessment).

Urine for pharmacokinetics was collected from 0–4 hrs, 4–8 hrs, 8–12 hrs and 12–24 hrs during the first 24 hrs and a 24-hr sample until 48 hrs p.i.

Whole body scintigraphic images were made directly after the infusion and 21 hours after the infusion. Twenty-one hours after infusion, in addition to the whole body image, single photon emission computed tomography (SPECT) and planar images of the head and neck region were made.

The patient was operated at 48 hrs p.i. and stayed in the hospital for post-operative care.

On day 7 (144 hrs p.i.) safety urine samples were collected. Adverse events and changes in the concomitant therapy were recorded daily.

Part B

Vital signs were recorded at 10, 60, 120 and 240 minutes post infusion. Blood samples for safety and for soluble CD44v6 were collected 21, 48 and 144 hrs post infusion. A blood sample for HAHA assessment was collected 144 hrs after the infuision. A urine sample for safety was also collected 144 hrs p.i.

Blood samples for pharmacokinetics were drawn at the end of the infusion and at 5 and 30 minutes and 1, 2, 4, 16, 21, 48, 72 hours after the end of the infutsion and on day 7 (144-hrs p.i.) after infuision. The originally planned sample at 10 minutes was omitted as per amendment 1.

Urine for pharmacokinetics was collected from 0–4 hrs, 4–8 hrs, 8–12 hrs and 12–24 hrs during the first 24 hrs and in 24-hr samples until 96 hrs p.i.

Whole body scintigraphic images were made directly after, at 21, 48, 72 and 144 hrs p.i. and optionally at two weeks p.i. if counting statistics permnitted.

Planar images of the head and neck region were made at 21, 48 (optional), 72 and 144 hrs p.i. and optionally at two weeks p.i., if counting statistics permitted.

SPECT imaging was only performed seventy-two hours after the infuision.

Adverse events and changes in the concomitant therapy were recorded daily.

Patients were allowed to leave the hospital after three days.

Visit 3: Follow-up Visits

Part A

Patients visited the outpatient clinic six weeks after the infusion. A physical examination was performned, safety blood and urine samples collected, body weight and vital signs measured and adverse events recorded. Blood samples for pharmnacokinetics, HAHA assessment and soluble CD44v6 were also obtained. A pregnancy test was required for women with childbearing potential. Follow-up of adverse events was recorded. Any changes in the concomitant therapy were recorded.

Part B

Patients visited the outpatient clinic weekly for at least six weeks for recording of adverse events and collection of safety blood samples. Blood samples for pharmacokinetics were drawn at 240 hours and 336 hours after infusion. The originally planned sample at 6 weeks p.i. was omitted as per amendment 1. Any changes in the concomitant therapy were also recorded. The disease assessment performed at baseline was repeated six weeks after the infusion and thereafter if indicated (the assessment was done after six weeks rather than after four weeks as mentioned once in the protocol). Six weeks after the infusion blood samples for safety, HAHA assessment and soluble CD44v6 were collected, vital signs recorded and body weight measured. A physical examination was done during this visit. A urine sample for safety was collected. A pregnancy test was required for women with childbearing potential.

Visits 4 and 5: Second Treatment (Part B)

A second treatment as outlined in the original protocol was not performed due to the premature termination of the trial because of the linker change. Instead patients who responded to the first dose of $^{186}$Re-BIWA 4 were eligible for a second administration. They underwent the same visit schedule as for the first administration.

Discussion of Study Design, Including the Choice of Control Groups

The aim of the present study was to assess the preferential accumulation of $^{99m}$Tc-labelled BIWA 4 in the tumour (Part A) and to evaluate the maximum tolerated dose of $^{186}$Re-BIWA 4 (Part B) as well as the pharmacokinetics of BIWA 4 in patients suffering from advanced head and neck cancer (Part A and B).

An open design was used as is general practice in these types of Phase I trials in oncology. A minimum of two patients in the lower radiation dose tiers and three patients in the higher radiation dose tiers were included in Part B of the trial. In case of occurrence of drug-related Common Toxicity Criteria (CTC) grade 4 haematology and grade 3 non-haematology toxicity a further three patients were treated with the respective dose tier (for further dosing details refer to section 3.4.4. and 3.4.5).

The dose of BIWA 4 administered was based on previous results with mMAb BIWA 1 indicating that a dose of 50 mg yielded a high and selective uptake in tumour tissue with a low uptake in non-tumour tissues and the results from Part A of the trial (see also section 3.4.4.1).

The starting dose level for radioactivity chosen was based on previous data suggesting that a dose of 20 mCi/m$^2$ may be a safe dose (see also section 3.4.4.2).

The criteria for efficacy which applied as well as the criteria for ssessing tolerability are well-established for this patient population and can also be evaluated in an open design.

Selection of Study Population

Inclusion Criteria

Patients with histological confirmation of squamous cell carcinoma in the head and neck.

Patients destined for surgery by means of a neck dissection (Part A) or:

Patients with either local and/or regional recurrent disease for which curative treatment options were not available, or distant metastases. The tumour deposits had to be measurable either clinically or by one or more radiological technique(s) (CT, MRI, bone scintigraphy). Because RIT was expected to be more effective in smaller size tumour deposits, patients with lesions measuring <3 cm in greatest dimension were preferred (Part B).

Patients over 18 years of age.

Patients younger than 80 years of age.

Patients who had given "written informed consent".

Patients with a life expectancy of at least 3 months.

Patients with a good performance status: Karnofsky>60.

Exclusion Criteria

Life-threatening infection, allergic diathesis, organ failure (bilirubin>30 μmol/l and/or creatinine>150 μmol/l) or evidence of a recent myocardial infarction on ECG or unstable angina pectoris.

Pre-menopausal women (last menstruation ≦1 year prior to study start):

Not surgically sterile (hysterectomy, tubal ligation) and

Not practising acceptable means of birth control, (or not planned to be continued throughout the study). Acceptable methods of birth control include oral, implantable or injectable contraceptives.

Women with a positive serum pregnancy test at baseline.

Chemotherapy or radiotherapy within 4 weeks before inclusion in the study.

White blood cell count <3000/mm$^3$, granulocyte count <1500/mm$^3$ or platelet count <100,000/mm$^3$.

Haematological disorders, congestive heart failure, bronchial asthma, alimentary or contact allergy, severe atopy or allergy.

Removal of Subjects from Therapy or Assessment

Criteria for Stopping Subject Treatment

The infusion had to be terminated immediately if the patient developed tachycardia (pulse rate greater than 120 per minute), hypotension (blood pressure less than 100 mm Hg systolic), respiratory distress, chest pain, or any symptoms intolerable to the patient.

Dropouts and Withdrawals

The subjects were free to discontinue their participation in this study at any time.

Evaluation of radiolabelled hMAb BIWA 4 was considered not to be feasible if the patient was prematurely removed from the study because of voluntary withdrawal. A case was considered not evaluable if adequate follow-up information was not available. Any unevaluable patients were planned to be replaced.

If the patient discontinued early from the study, the reason had to be documented on the CRF. If a patient did not return for the post-infusion blood samples for HAHA determination or pharmacokinetics, the reason had to be documented. If a patient developed a serious adverse event the study schedule had to be followed as closely as possible depending on the serious adverse events (SAE).

Treatments

Treatments Administered

Patients in Part A were administered $^{99m}$Tc-BIWA 4 at a radioactivity dose of 20 mCi. The dose of BIWA 4 administered was 25 mg, 50 mg or 100 mg for three patients each. The drug was administered intravenously as a single dose.

Patients in Part B received 50 mg BIWA 4 labelled with Rhenium 186. The lowest radioactivity dose was 20 mCi/M$^2$ which was increased in dose tiers of 10 mCi/m$^2$. The trial drug was administered intravenously as a single dose.

Identity of Investigational Product

| Part A: | |
|---|---|
| Substance (INN): | BIWA 4 (bivatuzumab) |
| Pharmaceutical form: | solution for injection |
| Chiffre number: | BIWA 4 LOI 99 1D 1A |
| Batch number: | B981101 |
| Source: | Boehringer Ingelheim Pharma KG |
| Unit strength: | 5 mg/mL |
| Daily dose: | 25 mg |
| Duration of use: | single dose |
| Route of administration: | intravenous |
| Posology: | infusion over five minutes |
| Substance (INN): | BIWA 4 (bivatuzumab) |
| Pharmaceutical form: | solution for injection |
| Chiffre number: | BIWA 4 LOI 99 1D 1A |
| Batch number: | B981101 |
| Source: | Boehringer Ingelheim Pharma KG |
| Unit strength: | 5 mg/mL |
| Daily dose: | 50 mg |
| Duration of use: | single dose |
| Route of administration: | intravenous |
| Posology: | infusion over five minutes |
| Substance (INN): | BIWA 4 (bivatuzumab) |
| Pharmaceutical form: | solution for injection |
| Chiffre number: | BIWA 4 LOI 99 1D 1A |
| Batch number: | B981101 |
| Source: | Boehringer Ingelheim Pharma KG |
| Unit strength: | 5 mg/mL |
| Daily dose: | 100 mg |
| Duration of use: | single dose |
| Route of administration: | intravenous |
| Posology: | infusion over five minutes |

BIWA 4 was administered as radioconjugate linked with $^{99m}$Tc. Linker molecule was MAG3. MAG3 was purchased from Mallinckrodt, Petten, The Netherlands.

$^{99m}$Tc was ordered locally via the laboratory where the radioimmunoconjugate was prepared (laboratory of Prof. Dr. van Dongen, Section Tumor Biology, Department of Otorhinolaryngology/Head and Neck Surgery, Vrije Universiteit University Medical Center, De Boelelaan 1117, 1081 HV Amsterdam, The Netherlands).

| Part B: | |
|---|---|
| Substance (INN): | BIWA 4 (bivatuzumab) |
| Pharmaceutical form: | solution for injection |
| Chiffre number: | BIWA 4 LOI 99 1D 1A |
| Batch number: | B981101 |
| Source: | Boehringer Ingelheim Pharma KG |
| Unit strength: | 5 mg/mL |
| Daily dose: | single dose |
| Route of administration: | intravenous |
| Posology: | infusion over five minutes |

BIWA 4 was administered as radioconjugate linked with $^{186}$Re. Linker molecule was MAG3. MAG3 was purchased from Mallinckrodt, Petten, The Netherlands.

$^{186}$Re was ordered locally via the laboratory where the radioimmunoconjugate was prepared (laboratory of Prof. Dr. van Dongen, Section Tumor Biology, Department of Otorhinolaryngology/Head and Neck Surgery, Vrije Universiteit University Medical Center, De Boelelaan 1117, 1081 HV Amsterdam, The Netherlands).

Characteristics and Quality of the Trial Drug

Antibody Characteristics

The antigen recognised by hMAb BIWA 4 is a transmembrane glycoprotein located on the outer cell surface and is only to a small extent internalised (<20%). Further analysis revealed that hMAb BIWA 4 recognises an epitope encoded by variant exon v6 of CD44. The antigen was shown to be expressed by all primary head and neck tumours (n=54) and by the majority of cells within these tumours. A comparable expression was observed for sixty-eight tumour infiltrated lymph nodes from neck dissection specimens (R97-2054). The reactivity pattern of hMAb BIWA 4 in human normal tissues is provided in Appendix III of the protocol. Reactivity of hMAb BIWA 4 was found to be essentially restricted to squamous epithelia. As demonstrated by the previous RIS study with murine monoclonal antibody (mMAb) BIWA 1, reactivity with normal squamous epithelium was not a limiting factor for utility in tumour targeting with respect to tumour uptake.

Quality control of $^{99m}$Tc- or $^{186}$Re-labelled hMAb BIWA 4

The antibody was labelled with $^{99m}$Tc or $^{186}$Re according to a method described by Fritzberg et al. (R96-2106: See protocol Appendix IV) which was modified according to Visser et al. (R96-2094) and Van Gog et al. R96-2111).

The procedures for radiolabelling hMAb BIWA 4 with $^{99m}$Tc and $^{186}$Re had been validated with respect to the final quality of the prepared conjugate. In five independent labelling experiments, performed according to the procedure described in appendix IV of the protocol, the percentage of label bound to the antibody was found to be 96–99%.

In this clinical investigation the radiochemical purity of each $^{99m}$Tc- or $^{186}$Re-labelled antibody batch prepared was assessed by thin layer chromatography (TLC) or high performance liquid chromatography (HPLC) and passage through a PD-10 gel filtration column, and had to be more than 90% to allow administration to a patient.

The immunoreactive fraction of each $^{99m}$Tc/$^{186}$Re-labelled antibody batch was checked after administration by use of validated methods and had to be above 60%. In brief, analyses were essentially performed according to a procedure as described by Lindmo et al. (R96-2104). UM-SCC 11B cells (human larynx carcinoma), containing the CD44v6 antigen, were fixed in 0.1% glutaraldehyde. Six dilutions, ranging from $5 \times 10^6$ cells per tube to $3.1 \times 10^5$ cells per tube, were made with 1% bovine serun albumine (BSA) in phosphate buffered saline (PBS).

To the tubes, 80,000 counts per minute (cpm) of the $^{99m}$Tc- or 10,000 of the $^{186}$Re-labelled hMAb BIWA 4 were added and incubated overnight at room temperature.

To the last sample, excess unlabelled hMAb BIWA 4 was added to determine non-specific binding. Cells were spun down and the radioactivity in pellet and supernatant were determined in a gamfma counter and the percentage bound and free radiolabelled MAb calculated (LKB-Wallac 1218 CompuGamma).

Data were graphically analysed in a modified Lineweaver Burk plot and the immunoreactive fraction was determined by linear extrapolation to conditions representing infinite antigen excess.

In case the discharge level of 60% was not reached in this binding assay the preparation for infusion was re-evaluated in a second binding assay. For this purpose the antibody preparation was labelled with $^{131}$I. The immunoreactive fraction in at least one of both assays, had to be larger than 60% for each patient to be evaluable and for the study to continue with the next patient.

Antibody Safety

BIWA 4 used for radiolabelling with $^{99m}$Tc and $^{186}$Re in this study is a well-characterised monoclonal antibody product which was produced by chinese hamster ovary (CHO)-cell culture fermentation. A master cell bank was established under Good Manufacturing Practice (GMP) conditions and thoroughly examined for microbiological status (bacteria, fungi, mycoplasma) as well as viral status (adventitious viruses, retroviruses). With the exception of endogenous retroviruses, which were known to be present in most CHO cells, no contaminants were detected.

In accordance with the Food and Drug Administration (FDA) 1994 "Points to consider" document on MAbs used in clinical phase I studies in cancer patients, a standardised downstream purification process, which has been validated for efficient virus removal, was applied to the purification of BIWA 4 material. Four model viruses were included in the validation (MuLV, PsRV, REO-3, SV 40). The concentrated bulk harvest was examined for the retrovirus titer to ensure that the subsequent downstream purification process was capable of adequately removing the retrovirus. Data on removal of endotoxins were within the acceptance limits ($\leq 0.01$ EU/mg) and were available for the bulk product. Furthermore pyrogenicity testing according to European Pharmacopoea guidelines had been successfully performed.

The final hMAb BIWA 4 to be used for further radiolabelling was analysed in great detail and was proven to be a highly pure (SDS page, isoelectric focusing), sterile solution containing minimal endotoxin levels ($\leq 0.01$ EU/mg). Results of testing for pyrogenicity were conform to European Pharmacopoea standard. The equality of the BIWA 4 product from the manufacture for pre-clinical and clinical supplies was demonstrated by analytical results.

Radiolabelling of hMAb BIWA 4 with $^{99m}$Tc or $^{186}$Re was performed by the department of Otolaryngology and Head & Neck Surgery of the Vrije Universiteit University Medical Center according to Standard Operating Procedures (SOPs). Sterility of the final product was guaranteed. Absence of endotoxins was tested during validation runs. For drug administration to a patient in the University Hospital Nijmegen the proper amount of radiolabelled hMAb BIWA 4 was transported in a special container directly after preparation to the study centre in Nijmegen. Twenty-four hours were allowed between labelling of the compound and administration to the patient.

See also appendix 16.1.6 for an allocation of the individual Rhenium batches to the patients.

Packaging, Labelling and Supply

BIWA 4 was supplied by Boehringer Ingelheim The Netherlands. It was produced by Boehringer Ingelheim, Germany using a GMP manufacturing and purification process and filled in vials as a sterile, non-pyrogenic solution containing 25 mg hMAb BIWA 4 in 5 mL isotonic PBS, pH 7.2. Examples of the vial labels of the native and also of the labelled antibody were included in the Clinical Trial Manual.

One batch with a total amount of 27 g of hMAb BIWA 4 had been prepared and filled into vials. Labelling of hMAb BIWA 4 with $^{99m}$Tc or $^{186}$Re was performed in a class B certified nuclear laboratory of the Vrije Universiteit University Medical Center, Amsterdam.

Storage Conditions

The unlabelled hMAb BIWA 4 had to be stored in the hospital pharmacy in a limited access area for study materials at a monitored temperature between +2 and +8° C.

Method of assigning subjects to treatment groups

No randomisation was used. Patients were assigned to the different dose groups according to the sequence of inclusion.

Selection of Doses in the Study

Selection of the BIWA 4 Doses

Part A:

Since hMAb BIWA 4 had never been administered to patients before, it was essential to be informed about its safety and biodistribution before starting RIT trials. Its biodistribution might strongly depend on the MAb dose used for tumour targeting and would need careful consideration. On the basis of MAb protein dose escalation studies with the low affinity anti-CD44v6 mMAb U36 and the high affinity anti-CD44v6 mMAb BIWA 1, it was anticipated that the optimal dose was in the range of 25–100 mg, with 50 mg being optimal for mMAb U36.

To confirm that this dose also was adequate for the intermediate affinity of hMAb BIWA 4 and to obtain initial information on the variability of the tumour uptake the biodistribution was assessed at 25, 50 and 100 mg total hMAb BIWA 4 and three evaluable patients were planned to be treated at each of these dose levels.

All evaluable patients received a single intravenous infusion of 2 mg hMAb BIWA 4 labelled with 20 mCi $^{99m}$Tc, measured by a radiation calibration system just prior to administration. Patients scheduled to receive 25 mg, 50 mg or 100 mg received 23 mg, 48 mg or 98 mg, respectively of unlabelled hMAb BIWA 4 administered together with this 2 mg hMAb BIWA 4 labelled with 20 mCi $^{99m}$Tc.

Selection of the BIWA 4 Dose for Part B:

On theoretical grounds a hMAb BIWA 4 dose of 50 mg was calculated as most suited for development. Part A of this study was performed to confirm the tumour preferential uptake of hMAb BIWA 4 at the three dose levels tested (25 mg, 50 mg and 100 mg). It was expected that the tumour uptake (expressed as percent injected dose per kilogram, % ID/kg) and tumour to non-tumour uptake ratio for these three dose levels would not differ much. If this was the case the hMAb BIWA 4 dose to be used for Part B of the study was 50 mg. However, if there was a clinically relevant difference between these dose levels, which favoured one over the other levels, the dose level with the best pattern of biodistribution would have been selected.

In this case a clinically relevant difference was defined as a difference of the tumour (mean of the tumour uptake) to bone marrow uptake ratio (mean of the bone marrow uptake=the cellular fraction and the supernatant) of more than 50 %.

Finally the dose selected was 50 mg hMAb BIWA 4 basing on the results of Part A.

Selection of the Radiation Starting Dose
Part B:

The hMAb BIWA 4 dose selected in Part A of the study was labelled with escalating doses of $^{186}$Re.

It has been reported that the maximum tolerated dose of $^{186}$Re-labelled murine MAb NR-LU-10 was 90 mCi/m$^2$ for heavily pre-treated patients, while dose-limiting myelosuppression was observed at 120 mCi/m$^2$. For chimeric MAb NR-LU-13, recognising the same antigen as NR-LU-10, reversible myelosuppression occurred at 60 mCi/m$^2$. In a study with cMAb U36, performed at the Vrije Universiteit University Medical Center dose limiting myelosuppression was observed at 41 mCi/m$^2$.

In the light of the above-mentioned results a radiation dose of 20 mCi/m$^2$ administered as $^{186}$Re-labelled hMAb BIWA 4 was considered a safe starting dose.

The dose was escalated with 10 mCi/m$^2$ increments. Two evaluable patients were entered at the lower dose levels. When ≧grade 2 drug-related toxicity according to the CTC was observed a minimum of three patients were treated per dose level.

Before entering patients at a next higher dose level it had to be sure that the patients at the ongoing dose level did not experience dose limiting toxicity (DLT) defined as: drug-related CTC grade 3 non-haematologic toxicity or drug-related CTC grade 4 haematologic toxicity excluding nausea and vomiting without adequate antiemetic treatment. For this purpose all patients at such an ongoing dose level had to be observed long enough to ensure that possibly induced toxicity was reversible.

When at the ongoing dose level one patient experienced DLT the number of patients treated at that dose level was increased to a total of six patients maximum. When 1 out of 6 patients experienced DLT the dose was escalated to the next level. When two or more of the patients experienced DLT, the next lower dose level was expanded (if not previously done) to a total of six patients in order to establish MTD and a safe recommended dose for phase II.

It was originally planned that in case of acceptable toxicity (less than two patients with DLT) at that dose level additional patients could be entered who received this dose and an escalating, lower second dose. This plan was not pursued due to the change of the linker. MAG3 will be replaced by MAG2GABA-TFP, a comparable linker, but with a more convenient linkage procedure. The present development programme with MAG3 has been finished.

Alternatively patients who responded to and tolerated the first administration of $^{186}$Re-BIWA 4 were eligible for a second administration with a dose of 50 mCi/m$^2$ $^{186}$Re-BIWA 4.

Selection and Timing of Dose for Each Subject
Dosage and Treatment Schedule

The investigators were allowed to administer the trial drug at any time. The time elapsed between radiolabelling and administration, however, should not exceed 24 hours.

Blinding

This was an open uncontrolled trial. No blinding was done.

Prior and Concomitant Therapy or Procedures
Rescue Medication and Additional Treatment(s)

Anaphylaxis was considered to be the most serious potential side effect and would have mandated immediate cessation of antibody infusion and the institution of appropriate resuscitative measures. Precautions to be taken were: Resuscitation equipment, within reach: anti-histaminics, corticosteroids and epinephrine. Any patient experiencing this type of adverse reaction was not allowed to receive additional monoclonal antibody.

Patients were allowed to receive other treatment(s) either for the study indication or for unrelated illnesses providing the inclusion and exclusion criteria were met. All concomitant therapy had to be recorded in the CRF.

In case of serious haematologic toxicity (CTC grade 4) cytokine intervention or other methods for alleviating bone marrow toxicity were allowed.

Restrictions

Additional chemotherapy or radiotherapy was not allowed and the last chemotherapy or radiotherapy should have stopped more than 4 weeks before inclusion in this study. All prior chemotherapy and radiotherapy was to be recorded in the CRF.

Treatment Compliance

The study medication was given as a single intravenous infusion. The compliance was verified with pharmacokinetic assessments and with radioimmunoscintigraphic images.

Efficacy/clinical Pharmacology and Safety Variables
Efficacy/pharmacodynamics and Safety Measurements Assessed and Flow Chart
Flow Charts:
Part A The investigations performed in Part A and the respective times are detailed in the flow chart given below. A description of the investigations is given in the following sections:

TABLE 3.5.1: 1

| FLOW CHART: Part A: Biodistribution study with $^{99m}$Tc-labelled hMAb BIWA 4 | | | | | | | | |
|---|---|---|---|---|---|---|---|---|
| | Visit 1 | Visit 2 | | | | | | Visit 3 |
| | screening | Day 1* | | | | | | Follow-Up |
| | visit* | pre-inj. | Post-inj. | Day 2 | Day 3 | Day 4 | Day 7 | Week 6 |
| Signed informed consent | x | | | | | | | |
| Demographics | x | | | | | | | |
| Conc. Therapy | x | x | x | x | x | x | x | X |
| Medical History | x | | | | | | | |
| Physical Examination | x | | | | | | | x |
| ECG | x | | | | | | | |
| Chest X-ray | x | | | | | | | |
| Blood safety analysis | $x^1$ | $x^1$ | | $x^1$ | $x^1$ | | $x^1$ | $x^1$ |
| Urine safety analysis | x | | | | | | x | x |
| Pregnancy test | x | | | | | | | x |
| HAHA assessment | $x^2$ | | | | | | $x^2$ | $x^2$ |
| ENT examination | x | | | | | | | |
| CT or MRI | x | | | | | | | |
| In-/exclusion criteria | x | | | | | | | |
| Adverse events | | x | x | x | x | x | x | X |
| Vital signs | $x^3$ | $x^3$ | $x^3$ | | | | | $x^3$ |
| body weight | x | x | | | | | | x |
| Immunoscintigraphy: | | | | | | | | |
| Whole Body Scan | | | $x^4$ | $x^4$ | | | | |
| Planar Scan | | | | $x^5$ | | | | |
| SPECT Scan | | | | $x^5$ | | | | |
| Pharmacokinetics: | | | | | | | | |
| Blood samples | | $x^6$ | $x^6$ | $x^6$ | $x^6$ | $x^6$ | $x^6$ | 6 |
| Urine collection | | $x^6$ | $x^6$ | $x^6$ | $x^6$ | | | |
| Serum soluble CD44v6 | | $x^7$ | | $x^7$ | $x^7$ | | $x^7$ | 6 |
| Surgery | | | | | x | | | |

*The pre-infusion assessments should occur no more than 3 weeks prior to the actual infusion.
$x^1$Blood samples were tested for: Glucose, sodium, potassium, calcium, chloride, creatinine, total protein, albumin, serum glutamic oxalacetic transaminase (sGOT), serum glutamic pyruvic transaminase (sGPT), Alkaline Phosphatase, Gamma Glutaryl Transpeptidase (GGT), bilirubin, urea, uric-acid, thyroid stimulating hormone (TSH), haemoglobin (Hb), haematocrit (Ht), mean corpuscular volume (MCV), reticulocytes, leucocytes, neutrophils,bands, lymphocytes, basophils, eosinophils, monocytes and platelets at the screening visit or on day 1 pre-infusion at 21, 48 and 144 hrs p.i. and at six weeks post infusion (p.i.).
$x^2$HAHA was assessed in a serum sample obtained at the screening visit, after one week (144 hrs) and after six weeks p.i.
$x^3$Vital signs were assessed at the screening visit, pre-infusion, at 10, 60 and 120 minutes post infusion and after 6 weeks.
$x^4$Whole body scan was done immediately after infusion and 21 hrs p.i.
$x^5$The SPECT scan and planar scan was done once 21 hrs p.i.
$x^6$Blood samples for pharmacokinetics were obtained pre-infusion, at the end of the infusion, at 5, 10, 30 minutes; 1, 2, 4, 16, 21, 48, 72 and 144 hrs post end of infusion and six weeks p.i. Blood samples were drawn for enzyme-linked immuno-sorbent assay (ELISA) and for measurement of radioactivity (for details see section 9.5.4.1). Urine was collected from 0–4 hrs, 4–8 hrs, 8–12hrs, and 12–24 hrs during the first 24 hrs and in a 24-hr sample for the remaining time until 48 hrs p.i.
$x^7$Soluble CD44v6 was measured from a serum sample obtained pre-infusion, at 21, 48 and 144 hrs p.i and six weeks p.i. 6 week six Part B
The investigations performed and the respective times are given in the flow chart below. The individual investigations are described in more detail in the following sections.

TABLE 3.5.1: 2

| FLOW CHART: Part B: Dose escalation study with $^{186m}$Re-labelled hMAb BIWA 4 | | | | | | | | |
|---|---|---|---|---|---|---|---|---|
| | Visit 1 | Visit 2 | | | | | | Visit 3 |
| | screening | Day 1* | | | | | | Follow-Up |
| | visit* | pre-inj. | Post-inj. | Day 2 | Day 3 | Day 4 | Day 7 | Week No. |
| Signed informed consent | x | | | | | | | |
| Demographics | x | | | | | | | |
| Conc. Therapy | x | x | x | x | x | x | x | 2, 3, 4, 5, 6 |
| Medical History | x | | | | | | | |
| Physical Examination | x | | | | | | | 6 |
| ECG | x | | | | | | | |
| Chest X-ray | x | | | | | | | |

TABLE 3.5.1: 2-continued

FLOW CHART: Part B: Dose escalation study with $^{186m}$Re-labelled hMAb BIWA 4

| | Visit 1 | Visit 2 | | | | | Visit 3 |
|---|---|---|---|---|---|---|---|
| | screening | Day 1* | | | | | Follow-Up |
| | visit* | pre-inj. | Post-inj. | Day 2 | Day 3 | Day 4 | Day 7 | Week No. |
| Blood safety analysis | $x^1$ | $x^1$ | | $x^1$ | $x^1$ | | $x^1$ | 2, 3, 4, 5, 6 |
| Urine safety analysis | x | | | | | | x | 6 |
| Pregnancy test | x | | | | | | | 6 |
| HAHA assessment | $x^2$ | | | | | | $x^2$ | 6 |
| ENT examination | x | | | | | | | 6 $x^8$ |
| CT or MRI | x | | | | | | | 6 $x^8$ |
| CT thorax | $x^8$ | | | | | | | |
| In-/exclusion criteria | x | | | | | | | |
| Adverse events | | x | x | x | x | x | x | 2, 3, 4, 5, 6 |
| Vital signs | $x^3$ | $x^3$ | $x^3$ | | | | | 6 |
| Body weight | x | x | | | | | | 6 |
| Immunoscintigraphy: | | | | | | | | |
| Whole Body Scan | | | $x^4$ | $x^4$ | $x^4$ | $x^4$ | $x^4$ | |
| Planar Scan | | | | $x^5$ | ($x^5$) | $x^5$ | $x^5$ | |
| SPECT Scan | | | | | | $x^5$ | | |
| Pharmacokinetics: | | | | | | | | |
| Blood samples | | $x^6$ | $x^6$ | $x^6$ | $x^6$ | $x^6$ | $x^6$ | 6 |
| Urine collection | | $x^6$ | $x^6$ | $x^6$ | $x^6$ | $x^6$ | | |
| Serum soluble CD44v6 | | $x^7$ | | $x^7$ | $x^7$ | | $x^7$ | 6 |

*The pre-infusion assessment had to occur no more than 3 weeks prior to the actual infusion.
$x^1$Blood samples were tested for: Glucose, sodium, potassium, calcium, chloride, creatinine, total protein, albumin, sGOT, sGPT, Alkaline Phosphatase, GGT, bilirubin, urea, uric-acid, TSH, Hb, Ht, MCV, reticulocytes, leucocytes, neutrophils, bands, lymphocytes, basophils,eosinophils, monocytes and platelets at the screening visit or on day 1 pre-infusion, at 21 hrs p.i., at 48 hrs p.i. and at 144 hrs p.i.. During weeks 2–6 p.i. safety blood samples were obtained at least weekly.
$x^2$HAHA was assessed in a serum sample obtained at the screening visit, at 144 hrs and six weeks post infusion.
$x^3$Vital signs were assessed once at the screening visit, pre-infusion, at 10, 60, 120 and 240 minutes post infusion and after 6 weeks.
$x^4$Whole body scan was done immediately p.i., at 21, 48, 72, 144 hrs p.i, and optionally at two weeks p.i.
$x^5$The planar scan was done at 21, 48 (optional), 72, 144 hrs p.i. and optionally at two weeks p.i. The SPECT scan was done at 72 hrs p.i.
$x^6$Blood samples for pharmacokinetics were obtained pre-infusion, at the end of the infusion, at 5, 30 minutes; 1, 2, 4, 16, 21, 48, 72, 144, 240 and 336 hrs post end of infusion. Blood samples were drawn for ELISA and for measurement of radioactivity. Urine was collected from 0–4 hrs, 4–8 hrs, 8–12hrs, and 12–24 hrs during the first 24 hrs and in 24-hr samples for the remaining time until 96 hrs p.i.
$x^7$Soluble CD44v6 was measured from a serum sample obtained pre-infusion, at 21, 48 and 144 hrs p.i and six weeks p.i.
$x^8$Disease assessment was to be repeated every 6 weeks until disease progression or loss to follow-up. CT thorax was done at baseline and repeated at follow-up if there were abnormalities. Radioimmunoscintigraphy and dosimetry The data obtained from radioimmunoscintigraphy (RIS) were presented qualitatively for both Part A and B (i.e. uptake in tumour, bone marrow, liver,lung, intestine, kidney and additional organs expressed as low, medium or high) and quantitatively for Part B.

For qualitative assessment the rating scale was transformed into numbers (0 being no uptake, 1 being low uptake, 2 being medium uptake and 3 being high uptake). Mean values were calculated and presented.

For Part B the quantitative presentation of RIS results used dosimetric calculations as outlined in section 5.1.4 of the protocol by including the following parameters:

Actual organ activity at a given time point expressed in MBq.

The residence time of radioactivity in organs expressed in hours.

The absorbed (radiation) dose expressed in mGy/MBq.

The effective (radiation) dose expressed in mSv.

More details concerning the analysis of dosimetry can be found in the dosimetry report (dated Nov. 21, 2001).

Radioimmunoscintigraphic Procedures

A description of the methods used for Part A and B and the time points are given in the following section:

Part A

With a large field of view dual headed gamma camera equipped with a low energy collimator, digital whole body images (anterior posterior (a.p.) and posterior anterior (p.a.)) were obtained directly after and 21 hrs after infusion. At 21 hrs p.i. planar and SPECT images of the head and neck were acquired. A calibration source also was acquired. Data was stored to enable quantitative analysis.

Part B

With a large field of view dual headed gamma camera equipped with a low energy collimator, digital whole body images (a.p. and p.a.) were obtained directly after, at 21, 48, 72 and 144 hrs after administration of the radioimmunoconjugate. Additional planar images of the head and neck region were made at 21, 48 (optional), 72, and 144 hrs p.i. Optionally additional imaging (whole body and planar) were performed two weeks p.i. A calibration source (i.e. an aliquot with a known fraction of the injected dose in a 10 millilitre (ml) vial), inserted in an Adams phantom, had to be placed between the lower legs of the patient during the whole body scan. The initial activity of the calibration source had to be 100–200 MBq $^{186}$Re and this source had to be used during all whole body imaging studies. The energy-window and peak settings, the scanspeed, the scanlength, the scanning date, the time of starting the scan and the scan duration had to be reported. The anterior-posterior thickness of the neck and of the abdomen had to be measured, while the patient was in supine position on the scanning table.

At each imaging session, anterior and planar static images had to be taken and just before or just after this image a static image had to be acquired from the calibration source in the Adams-phantom.

At 72 hr. p.i. a SPECT study of the neck had to be performed. The methods used for reconstruction and the filter functions with cut off frequencies had to be reported.

Single Photon Emission Computed Tomography (SPECT)

SPECT images were obtained using a double headed rotating gamma camera equipped with a low energy collimator. Acquisition required at least thirty minutes. Twenty percent symmetric windows were centred at the 137 keV photon peaks.

Planar and SPECT Data Acquisition Parameters

Planar imaging included the following minimal requirements: matrix 128×128 (detail) or 256×256 (whole body) and a minimum of 400000 counts with a maximum acquisition time of 10 minutes for detail and 60 minutes for whole body.

SPECT imaging included the following minimal requirements: 64 images, matrix size 64×64, 360 degree circular orbit, 60 second acquisitions per angle.

Analysis of the Data

At the 21 hr p.i. anterior whole body images, rectangular regions of interest (ROI's) had to be drawn around the whole body and the calibration source. Also irregular ROI's around the organs which accumulated $^{186}$Re (e.g. liver, spleen and left kidney) and around the tumour had to be drawn. One or more representative background regions had to be drawn. These regions had to be mirrored to the posterior images. Originally it was planned to draw a ROI around the sacrum on the posterior image. This plan was not pursued during the trial. All regions had to be saved on the computer, in order to project these ROI's on images at other time points. The number of pixels and the counts per pixel in each region had to be reported. The number of counts in the regions for all imaging time points had to be recorded digitally in a spreadsheet.

Calculation of the Absorbed Dose in the Organs

The amount of activity in the organs, tumour and the total body was estimated from the geometric mean counts in the ROI's of the anterior and posterior views. Background and attenuation correction were applied when indicated. The activity in the urine was not used to estimate the absorbed dose in the bladder as originally planned. Instead the dynamic bladder model was used. The residence times in the organs and the rest of the body were calculated and imported in the MIRDOSE3 program.

Required Quality Control Tests

Planar Imaging

Routine quality controls were performed at the department of nuclear medicine weekly:
1) 100M flood table.
2) Extrinsic $^{57}$Co flood with the low energy collimator was obtained each week.

SPECT Imaging

Quality control of the SPECT imaging system had to include center of rotation determination.

Tomographic Processing

A filtered back projection algorithm was used for tomographic image reconstruction using a ramp filter.

Data Storage

All planar images and tomographic data had to be stored permanently on magnetic tape or optical disc. For tomographic studies, original projecting images and reconstructed studies had to be written to a back up tape.

Copies of Images and Reports

Copies of all relevant images, pathology and surgery reports were required for all patients. Also copies of MRI and CT reports were required.

Biopsy biodistribution of $^{99m}$Tc-labelled hMAb BIWA 4 (Part A)

Patients entered in Part A of the study underwent surgery 48 hrs after infusion of the radiolabelled hMAb BIWA 4. Biopsies from tumour site(s) and from normal tissues (as many as possible) in the surgical specimen were taken. Then also under general anaesthesia a bone biopsy and a bone marrow aspirate was taken. The bone marrow aspirates were centrifuged to assess the radioactivity in the supernatant (plasma) and in the sediment (cellular fraction).

All biopsies were weighed and the amount of $^{99m}$Tc was measured. Specific uptake of radioactivity into tumour was evaluated by comparing % ID/kg tumour with % ID/kg normal tissue.

CD44v6 antigen expression was assessed by immunohistochemistry using cryostate sections, which were first incubated with mMAb BIWA 1, followed by anti-mouse Immunoglobulin G (IgG) secondary reagent. The surgical specimen and the biopsies were investigated histo/cytopathologically.

Evaluation of Surgical Specimen and Biodistribution

After receiving the surgical specimen it was processed in the following chronological order.

1. Pictures were taken of the specimen. A Polaroid from the front and slides from the front and back.
2. The size of the surgical specimen was assessed.
3. Biopsies of primary tumour, suspect lymph node, and if possible from normal tissues in the surgical specimen like normal mucosa, normal lymph node, fat and muscle were taken. All biopsies were weighed and the amount of $^{99m}$Tc was measured. All data were converted to percentages injected dose/kilogram tissue. Specific uptake of radioactivity into tumour was evaluated by comparing % ID/kg tumour with % ID/kg normal tissue.
4. Next the specimen was nailed to a board and fixed in formaldehyde 4% for at least 36 hours.
5. After dissecting the sternocleidomastoid muscle (a structure with a high radiodensity), a specimen radiograph was made to show the exact size and location of the lymph nodes involved. This radiograph was made while the specimen was being immersed in ethanol 96%, which has the same X-ray absorption as fat.
6. All the nodes visualised with the X-ray were indicated on the Polaroid and specimen radiograph.
7. All the nodes found by examining the surgical specimen and by X-ray were dissected from the specimen.
8. All macroscopically negative nodes were entirely processed for microscopy and one single section was evaluated. Of all macroscopically positive nodes two or more slices were made. Macroscopical evidence for the presence or absence of tumour necrosis were recorded.
9. Furthermore, the number of nodes enclosed and the number, localisation and lymph node level (according to the Memorial Sloan Kettering Cancer Center Classification) of tumour containing nodes were recorded.

Tumour Response (Part B)

The efficacy parameter for the radioimmunotherapy treatment was tumour response. Tumour response was assessed with tumour measurements as assessed clinically and/or with CT, MRI or bone scintigraphy investigations. Evaluation was done according to response criteria of the World Health Organisation (WHO). See Appendix VI of the protocol, (R96-0941).

Physical Examination

Before inclusion in the study the disease status of each patient was evaluated by ENT-examination (palpation included) and by CT or MRI of the tumour site(s).

All head and neck lesions were described per neck side.

Palpation

All patients were examined at baseline by an otolaryngologist/head and neck surgeon. This clinical investigator assessed the number, size, location and mobility of all palpable lymph nodes in the head and neck area. The character of the lymph nodes was described as: not suspected, suspected or tumour infiltrated. The status of the neck lymph nodes was classified according to the Tumour Node Metastasis system for staging rumours (TNM) of the Union Internationale Contre le Cancer (UICC) at diagnosis.

Radiological Examination

Depending on the localisation of the tumour site(s), one or more of the following examinations were required: CT, MRI, bone scintigraphy. For tumour involvement of the head and neck region MRI was generally preferred. In case there were bone lesions, CT was preferred. For Part B all radiological disease assessment parameters obtained at baseline were repeated six weeks after the infusion and every six weeks until progression or lost to follow-up. For patients entered in Part B of the study a CT thorax was obtained at baseline, and was repeated at follow-up if there were tumour lesions in the thorax. Ultrasound might have been employed as additional technique of tumour imaging. Guidelines for the investigations are given below:

Primary Tumour/loco-regional Recurrence

For patients participating in Part A of the study and patients with a loco-regional recurrence (Part B) CT scan and/or MRI of the head and neck region had to be performed.

Computed Tomography

Computed tomography of the Head and Neck region: Dynamic CT was preferred over spiral CT. However, spiral CT might have been helpful in patients who were unable to cooperate.

The patient had to be examined in supine position, the neck slightly hyperextended, the head immobilised and the shoulders relaxed and pushed downwards. The patient had to breath quietly with use of abdominal rather than chest muscles. The area to be scanned was determined from the initial overview made in the lateral projection. The plane of the scan had to be parallel to that of the vocal cords. Contiguous three millimetre-slices had to be used routinely. Imaging had to be performed from skull base to upper mediastinum.

Magnetic Resonance Imaging

The patients had to be examined in supine position, the neck slightly hyperextended and the head immobilised. Quiet breathing was mandatory during the examination with the use of abdominal rather than the chest muscles. The appropriate images to demonstrate the neck anatomy and to assess the extent of the primary lesion and the presence of lymph node spread was obtained. They had to be obtained from the skull base to the upper mediastinum.

Distant Metastases

For all patients participating in Part B of the study CT scanning of the thorax was done at baseline. Additional investigations to visualise metastases, like bone scintigraphy or CT abdomen, were optional.

CT Thorax

Spiral CT-scans were obtained. Patients were examined in supine position and had to raise their arms above their heads. Patients had to breath quietly with use of abdominal rather than chest muscles. The patient was scanned from just above the lungs to the level of the adrenal glands. Images had to be photographed in mediastinal and lung setting.

CT Abdomen

Spiral scans were obtained. Patients were examined in supine position and had to raise their arms above their heads. Patients had to breath quietly. Oral contrast was used in all patients. The area to be scanned ran from just above the diaphragm to the symphysis. Images had to be photographed in abdominal and liver setting.

Bone Scintigraphy

After intravenous infusion of maximally 600 MBq of $^{99m}$Tc-labelled HDP/MDP, the patient was asked to consume enough fluids and to void frequently. Static views were obtained 3 hours after infusion: one whole body view and if necessary 3 more detailed views. Suspect lesions might have needed closer analysis by CT and/or MRI.

Reporting of response of bone metastases were planned to be conducted according to a separate set of response criteria. No data was provided.

Soluble CD44v6

Soluble CD44v6 (sCD44v6) had to be measured in serunm. Concentrations were determined by means of a validated enzyme-linked immuno-sorbent assay (ELISA) that was based on a commercially available test kit and conducted in accordance with current international guidelines at the Boehringer Ingetheim Department of Pharmacokinetics and Drug Metabolism, Biberach, Germany. Blood samples (to be processed to serum) of 5 mL were obtained pre-infusion, at 21, 48 and 144 hrs p.i. and six weeks after the infusion. Samples were allowed to clot and centrifuged to prepare serum. Storage and shipment conditions: The sample for ELISA measurement was put in cryotubes, labelled carefully to enable unique identification, stored at −20° C. until radioactivity has decreased ($^{186}$Re: 4 weeks, $^{99m}$Tc: 3 days) and sent to BI Department of Pharmacokinetics and Drug Metabolism, Biberach, Germany in batches every four weeks. The serum samples were sent on dry ice.

Safety

Protection of Subjects

All patients were monitored carefully during and after administration of the radiolabelled monoclonal antibody. For this purpose at least one of the investigators was present.

Laboratory Assessments

Blood samples were collected for glucose, sodium, potassium, calcium, chloride, creatinine, total protein, albumin, serum glutamic oxalacetic transaminase (sGOT), serum glutamic pyruvic transaminase (sGPT), alkaline phosphatase (AP), gamma glutaryl transpeptidase (GGT), bilirubin, urea, uric-acid, thyroid stimulating hormone (TSH), haemoglobin (Hb), haematocrit (Ht), median corpuscular volume (MCV), reticulocytes, leucocytes, neutrophils, bands, lymphocytes, basophils, eosinophils, monocytes and platelets at the following time points:

At the screening visit or on day one pre-infusion and

At 21, 48 and 144 hrs post infusion.

For Part A at 6 weeks post infusion. For Part B: During weeks 2, 3, 4, 5 and 6 of the study at least once weekly (more often in case of toxicity).

Baseline laboratory assessments pre-infusion could have been obtained either at the screening visit or on day one of the study, provided the samples were obtained less then 21 days before the infusion of radiolabelled hMAb BIWA 4 and all required assessments were done. All required laboratory test results had to be reviewed and checked for eligibility by the responsible physician prior to the antibody infusion. The same also applied to a second hMAb BIWA 4 administration in Part B of the study.

Urine samples were collected for standard hospital screening (protein, blood, and glucose) at the time points:

Screening visit

One week post infusion (144 hrs p.i.)

Six weeks post infusion

A pregnancy test was required for women with childbearing potential at the screening visit and at the study end.

Human-Anti-Human-Antibody Assessment

The presence and/or the development of HAHA was evaluated in serum samples. Therefore blood samples (to be processed to serum) of 5 mL were taken at the screening visit, at one week (144 hrs p.i.) and at six weeks after infusion of the antibody. For patients receiving two BIWA 4 administrations in Part B of the study an additional HAHA sample was collected before the second administration. Serum level was evaluated by means of validated ELISA methods.

Samples were allowed to clot and centrifuged to prepare serum.

Storage and shipment conditions: The samples for ELISA measurement were to be put in cryotubes, labelled carefully to enable unique identification, stored at −20° C. until radioactivity had decreased ($^{186}$Re: 4 weeks, $^{99m}$Tc: 3 days) and sent to BI Department of Pharmacokinetics and Drug Metabolism, Biberach, Germany in batches every four weeks. The serum samples had to be sent on dry ice.

Any elevations in human anti-human antibody levels were compared casewise carefully with the patient's possible adverse events. This data was collected and analysed retrospectively during the course of the study.

Adverse Events

All adverse events were recorded in the CRF. The events were graded according to the US National Cancer Institute CTC (NCI-CTC) version 2.0 (a version of this document had to be downloaded from the Internet at the site: http:/ctep.info.nih.gov/CTC3/ctc.htm. All SAEs had to be reported.

Immunogenicity and Toxicity

Before performance of this trial no human data existed with respect to safety and immunogenicity of hMAb BIWA 4. In the previous study performed with the parental murine antibody BIWA 1 no clinically significant toxicity was encountered. No toxicity was expected from the naked hMAb BIWA 4 antibody alone (no antibody dependent cell-mediated cytotoxicity (ADCC) effector functions in vitro; no interference with proliferation of antigen-expressing cells expected). It was demonstrated that hMAb BIWA 4 could be safely administered to mice (xenograft studies) and monkeys (toxicity studies). Good local tolerability was demonstrated in three local toxicity studies.

Murine and chimeric MAb U36 (anti-CD44v6-epitope with defined overlapping epitope specificity) was so far safe in HNSCC patients; no toxicities except for myelotoxicity (caused by $^{186}$Re-labels) were seen in a Phase I dose-escalation RIT study with cMAb U36. It was theoretically possible that hypersensitivity reactions to radiolabelled hMAb BIWA 4 might occur. Monoclonal antibodies have been administered to several thousands of patients for diagnostic applications.

Although unlikely, potential reactions to intravenously administered BIWA 4 might include hypotension, transient fever and chills, skin rashes, dyspnoea, itching, nausea, and anaphylaxis.

Vital signs (blood pressure, temperature, pulse rate and respiratory rate) were therefore recorded at the screening visit and at the following time points: pre-infusion and 10, 60, 120 minutes post-infusion and after 6 weeks. Additionally vital signs were recorded at 240 minutes post-infusion for patients participating in Part B only.

In this study radionuclides were used. The radiation burden associated with the ganmma emitting radionuclide $^{99m}$Tc (in the current study 20 mCi) was similar to that encountered in many routine nuclear medicine procedures, and was known to be small. To minimise radiation exposure to the bladder and kidneys the patients were well hydrated and asked to void at frequent intervals during the first 48 hours (96 hours after infusion with $^{186}$Re-labelled antibody).

For the beta- and gamma-emitting radionuclide $^{186}$Re, Breitz et al. (R98-2459) found a maximum tolerated dose of $^{186}$Re-labelled MAb IgG in heavily pretreated patients of 90 mCi/M$^2$. One of the aims of this study was to investigate the toxicity of $^{186}$Re-labelled hMAb BIWA 4 in patients who either had local and/or regional recurrent disease for which curative treatment options were not available, or distant metastases. Because bone marrow, thyroid, kidney and liver toxicity might occur, blood samples for organ function testing were taken as described in section 3.5.1.6.

To monitor the occurrence of weight loss or weight gain the body weight was recorded at the screening visit, before the infusion on day 1 and after 6 weeks.

Patients were monitored for the occurrence of local toxicity. Any sign of local toxicity was recorded as adverse event.

Appropriateness of Measurements

The measurements used are well-accepted for this type of trial.

Primary Efficacy/pharmacodynamic Variables(s)

Part A of the Trial

The primary efficacy variables determined in Part A of the trial were the biopsy distribution and the radioimmunoscintigraphy. Description of the methods how to obtain the data is given in section 3.5.1.1 and 3.5.1.2.

The uptake in the normal tissue and tumour was measured in biopsies of the surgical specimen and the uptake expressed as percent of the injected dose per kg (% ID/kg) .The time course of uptake in the tumour and other tissues was evaluated and compared concerning the different doses of BIWA 4.

Part B of the Trial

The primary parameters for efficacy were the analysis of radioimmunoscintigraphy and dosimetry.

Drug Concentration Measurements/pharmacokinetics

Blood concentrations of radiolabelled BIWA 4 were determined in both Part A and Part B of the trial.

Methods and Timing of Sample Collection

Patient blood samples were collected and handled as follows: 7 mL of blood (3.5 mL in potassium EDTA containing tubes and 3.5 mL in coagulation tubes: amount of millilitres requested are given as per amendment 1) were sampled from a peripheral vein of the arm opposite to the infusion site at the designated time points (i.e. just prior to antibody administration, at the end of the infusion and at 5, 10, 30 minutes; 1, 2, 4, 16, 21, 48, 72 hrs post-end of infusion and on day 7 p.i. (144 hrs) and 6 weeks after the infusion). End of infusion was regarded as t=0.

The planned samples at 10 minutes and 6 week p.i. were omitted for Part B of the trial. Instead samples were collected at 240 and 366 hour p.i. as per amendment 1.

Urine was collected during 48 hrs after the $^{99m}$Tc-labelled hMAb BIWA 4 infusion and during 96 hrs after the $^{186}$Re-labelled hMAb BIWA 4 infusion. Urine was collected from 0–4 hrs, 4–8 hrs, 8–12 hrs, and 12–24 hrs during the first 24 hrs and in 24-hr samples for the remaining time. Radioactivity of urine samples was counted to determine the excretion of radioactivity.

Blood samples were centrifuged to prepare serum. Before processing, the radioactivity in whole blood was measured. Radioactivity was also measured in serum. Refrigerated storage of blood samples was obligatory, though samples had not to be frozen down. Using the aliquot retained from the conjugate preparation, a weighted dilution of the injected patient dose was prepared as standard. The counting of the patient samples and standards were performed according to local SOPs. Results were recorded in the appropriate sections of the CRF. The radionuclide content was reported as a percentage of the injected doses (expressed as % ID/kg blood or serum). Apart from radioactivity counting all samples were analysed for presence of immune complexes by means of HPLC analysis.

All sample tubes were labelled with the following information: Trial number, patient number, sample identification (i.e., serum, plasma, or blood), time relative to infusion, actual time, actual date and isotope (i.e., $^{99m}$Tc or $^{186}$Re). The volume of each urine sample was measured and recorded and all urine samples were labelled with the following information: Trial number, patient number, total sample volume, collection interval, actual time, date and isotope (i.e., $^{99m}$Tc or $^{186}$Re).

Dates, times and radioactivity measurement results of all pharmacokinetic samples were recorded in the CRF.

The plasma samples for ELISA measurement were transferred in cryotubes, labelled carefully to enable unique identification, stored at −20° C. until radioactivity had decreased ($^{186}$Re: 4 weeks, $^{99m}$Tc: 3 days) and sent to Boehringer Ingelheim Department of Pharmacokinetics and Drug Metabolism, Biberach, Germany in batches every four weeks. The plasma samples were sent on dry ice.

Analytical Determinations

Plasma samples were measured by validated ELISA methods at the Boehringer Ingelheim Department of Pharmacokinetics and Drug Metabolism, Biberach, Germany. Radioactivity counting of the samples were performed in full blood, serum and urine by the investigator.

Parameters and Evaluation

The following pharmacokinetic parameters using WinNonlin 3.1 Professional (Pharsight Corporation, Mountain View, Calif.) were determined from full blood, plasma, serum levels and imaging data as described below:

The primary pharmacokinetic parameters are the time point at which the maximum drug concentration is observed ($T_{max}$), maximum drug concentration observed ($C_{max}$), area under the concentration-time curve ($AUC)_{0\to\infty}$, terminal elimination half-life ($t_{1/2}$), volume of distribution (terminal phase and predicted steady state), total body clearance (CL), and mean residence time $(MRT)_{0\to\infty}$.

The primary objectives of pharmacokinetic analysis were:

To determine and compare the disposition of total radioactivity and immunoreactive hMAb BIWA 4 following administration of single doses of $^{99m}$Tc-labelled (Part A) and $^{186}$Re-labelled hMAb (Part B) BIWA 4.

To calculate, from imaging data and blood disposition data, the fraction of the injected radioactivity reaching the liver and spleen during the studies. To achieve this objective, the WinNonlin® software package was used to perform non-compartmental pharmacokinetic analysis on the plasma concentration vs. time profiles of immunoreactive hMAb BIWA 4 and of total blood radioactivity levels, as a function of time, following intravenous administration.

The results are reported as summary statistics.

Pharmacokinetic/pharmacodynamic Relationship

A compartmental pharmnacokinetic model was initially intended to describe the distribution and metabolism of $^{186}$Re-labelled BIWA 4 in humans. It was intended to combine data from BIWA 4 plasma levels, full blood and serum radioactivity measurements, radioactivity from whole body images and specific regions of interest, the administered dose $^{186}$Re-labelled BIWA 4, the dose of unlabelled BIWA 4, soluble CD44v6 levels and the assessment of the radiolabelled antibody prior to infusion.

The results were to be reported as summary statistics. However, variability was too high to be used for a reasonable model.

Primary Safety Variable

Determination of maximum tolerated dose and assessment of safety were the primary endpoints in Part B of the trial. The measurements done are described in section 3.5.1.6.

Dose Limiting Toxicity and Maximum Tolerated Dose

DLT was defined as drug-related CTC grade 3 non-haematologic toxicity or drug-related CTC grade 4 haematologic toxicity, excluding nausea and vomiting without adequate antiemetic treatment.

The MTD was defined as the dose level at which less than two out of six patients developed drug-related DLT.

Data Quality Assurance

The trial was in general conducted according to the principles of Good clinical Practice as specified in the appropriate regulations and in the company standard operating procedures reflecting these regulations.

Throughout the course of the study, a representative from Boehringer Ingelheim The Netherlands was contacting and/or visiting the study site to monitor the progress of the study. There were frequent contacts with the investigator and onsite visits for the purpose of data audits, including the comparison of source documents with Case Report Forms and drug accountability checks. The investigator or his/her designee had to be available to the Boehringer Ingelheim The Netherlands representative during these onsite visits.

Duly filled in CRFs were collected on a regular basis. Data were double-data entered in-house. Review of the data was done and implausibilities questioned to the investigator.

Serious adverse events were reported according to the guidelines defined in the protocol and CRF and according to Boehringer Ingelheim SOPs.

Statistical Methods Planned in the Protocol and Determination of Sample Size

Statistical and analytical plans

Statistical design/model

The designs used in this trial are commonly used in Phase I oncology trials.

Part A

Part A of this phase I trial was an uncontrolled, rising dose sequential group study to determine the safety, tolerability, biodistribution and pharmacokinetics of a single infusion of $^{99m}$Tc-labelled hMAb BIWA 4 in patients with advanced squamous cell carcinoma of the head and neck.

Three hMAb BIWA 4 dose levels were used in this part of the study with three patients planned at each dose level. All patients had a proven tumour of the head and neck and were destined for surgery.

Part B

Part B of this phase I trial was an open uncontrolled dose escalation study to determine the safety, tolerability, MTD, pharmacokinetics and preliminary therapeutic effects of a single infusion of $^{186}$Re-labelled hMAb BIWA 4 in patients with advanced squamous cell carcinoma of the head and neck for whom no curative treatment options were available.

In this part of the study the radiation dose was escalated. Two patients were treated at dose levels where <grade 2 CTC toxicity was seen. If ≧grade 2 toxicity was seen at least three patients were treated per dose group.

Safety and Tolerability Evaluation (Parts A+B)

Safety and tolerability of the study were assessed in terms of changes in laboratory parameters, vital signs, development of HAHA and the incidence of adverse experiences. The results were reported for each dose level separately as well as in terms of overall means.

Biodistribution Evaluation (Part A)

The biodistribution of $^{99m}$Tc-labelled hMAb BIWA 4 in solid tissue was assessed by radioimmunoscintigraphy (see sections 3.5.1.1) and by measurements of radioactivity of biopsy specimens (see sections 3.5.1.1 and 3.5.1.2). Because only a maximum of 3 patients were entered per dose level only descriptive statistics were possible.

Immunoscintigraphic Imaging Evaluation (Parts A+B)

At given time-points after the administration of radiolabelled antibody immunoscintigraphic images were obtained (see section 9.5.1.1). Again only descriptive statistics were applicable.

Pharmacokinetic Evaluation (Parts A+B)

The following pharmacokinetic parameters were determined from plasma or serum, urine levels and imaging data as described below:

Primary Parameters (Non-compartmental)

$T_{max}$, $C_{max}$, AUC (0-infinite time), terminal elimination half-life, volume of distribution (terminal phase $V_z$ and predicted steady state $V_{ss}$), CL, and MRT (0-infinite time). Cumulative urinary excretion of radioactivity over time was determined from total urine output.

Secondary Parameters (Compartmental)

A compartmental pharmacokinetic model was planned to be developed to define the distribution and metabolism of $^{186}$Re-labelled hMAb BIWA 4 in humans. The model collated data from serum and urine radioactivity measurements, radioactivity from whole body images and specific regions of interest, the administered dose $^{186}$Re-labelled hMAb BIWA 4, the cold-loading dose of hMAb BIWA 4, soluble CD44v6 levels and the assessment of the radiolabelled antibody prior to infusion.

The results were planned to be reported for each dose level separately and by means of summary statistics.

Therapeutic Efficacy Evaluation (Part B)

Tumour response was the parameter for therapeutic efficacy. Tumour response was assessed according to the WHO guidelines. The sum of the products of the largest perpendicular diameters of all measured tumour lesions were the primary parameter for tumour response. There were separate criteria for the assessment of response of bone lesions.

Null and Alternative Hypotheses

All analyses in this trial were descriptive and exploratory by nature. Any statistical tests were performed only to provide a statistical framework from which to view the results and providing aid for planning further studies. No formal statistical inferences were foreseen and, accordingly, no statistical tests were performed.

Planned Analyses

Two populations were distinguished:

The intention to treat subset consists of all patients who received an infusion of radiolabelled hMAb BIWA 4 and for whom data after baseline were available.

The per protocol subset consists of evaluable patients. A patient was evaluable if the following criteria were met:

Part A:
Fulfilling the criteria for the intention to treat subset.
The follow-up in terms of adverse events, vital signs and safety blood and urine samples was adequate.
The immunoreactive fraction in at least one of both performed assays was larger than 60%.
Adequate biopsies and scintigraphic images were available to assess the biodistribution.

Part B:
1. Fulfilling the criteria for the intention to treat subset.
2. The follow-up in terms of adverse events, vital signs and safety blood and urine samples was adequate.
3. The immunoreactive fraction in at least one of both performed assays was larger than 60%.
4. Response: Patients (Pts.) were evaluable for response if adequate tumour measurements were obtained at baseline and if patients were followed over at least a six week period. If disease progression was observed within this six weeks period, patients were also evaluable for response.

Primary Analyses

The primary analysis was performed for the per protocol subset.

Non evaluable patients were replaced. For Part A therefore the evaluable subset was planned to consist of 9 patients and the intent to treat subset consisted of at least 9 patients. For Part B the number of patients depended on the toxicity encountered. Patients who were evaluable for toxicity but not for response were not replaced.

Pharmacokinetic Data:

The analysis of pharmacokinetic data was performed by Dr. Thomas R. MacGregor, Boehringer Ingelheim Pharmaceuticals Inc. Ridgefield Conn., USA.

The primary objectives of pharmacokinetic analysis were:

To determine and compare the disposition of total radioactivity and imnnunoreactive hMAb BIWA 4 following administration of single doses of $^{99m}$Tc-labelled hMAb BIWA 4 and $^{186}$Re-labelled hMAb BIWA 4.

To identify an appropriate cold-loading dose of hMAb BIWA 4.

T assess the disposition of a second dose of $^{186}$Re-labelled hMAb BIWA 4.

To calculate, from imaging data and blood disposition data, the fraction of the injected radioactivity reaching the liver and spleen during the studies. To achieve this objective, the WinNonLin® software package was used to perform noncompartmental pharmacokinetic analysis on the plasma concentration vs. time profiles of immunoreactive hMAb BIWA 4 and of total blood radioactivity levels, as a function of time, following intravenous administration. Any measurements involving radioactivity were normalised to the fraction of the radiolabel that was protein-bound and immunoreactive prior to infusion. The specific pharmacokinetic parameters that were generated include: $T_{max}$, $C_{max}$, AUC (0-infinite time), terminal elimination half-life, volume of distribution (terminal phase and predicted steady state), total body clearance, and mean residence time (0-infinite time). Cumulative urinary excretion of radioactivity over time were determined from total urine output.

The secondary objective of the pharmacokinetic analysis to develop a pharmacokinetic model to describe the distribution and metabolism of $^{186}$Re-labelled hMAb BIWA 4 in humans was not achieved due to the high variability of the data (especially the radioscintigraphic data).

Secondary Analyses

The secondary analyses were performed for the intention to treat subset of patients participating in Part B of the study.

The secondary analyses were restricted to key endpoints: e.g.: Response rate, duration, of response, time to progression.

Interim Analysis

No interim analyses were made.

Handling of Missing Data

In this phase I study it was anticipated that most data were available for analysis. In case of missing data it was most likely that the reason for missing was not outcome related. No missing data were imputed.

Determination of Sample Size

In Part A three patients per dose level provide some information on safety of the hMAb BIWA 4 and on the anticipated correct dose of 50 mg unlabelled hMAb BIWA 4.

In Part B six patients were regarded sufficient to determine DLT. TABLE 3.7.2:1 exhibits the probabilities of 2 or more out of 6 patients to be observed with DLT for some assumed underlying rates of DLT in the population of all patients.

TABLE 3.7.2: 1

| | Assumed Population Rates of DLT | | |
|---|---|---|---|
| | 0.40 | 0.42 | 0.45 |
| Probability of observing DLT in two or more out of six patients | 0.77 | 0.80 | 0.84 |

Source: Probabilities calculated from the cumulative distribution function of the binomial distribution with n = 6 and varying p's.

With the escalation scheme in this trial, there was a probability of at least 80% for two or more patients to exhibit DLT, if the underlying individual probability for a patient to reach DLT is 42% or larger.

Changes in the Conduct of the Study or Planned Analyses

The following changes from protocol were implemented via an amendment.

Time points for collection of blood samples were adjusted by implementation of amendment No 1 dated 1 Sep. 1999. The samples at 10 minutes and 6 weeks after infusion were dropped while additional samples were collected after 240 and 336 hours post end of infusion in Part B of the trial. It had turned out that the original blood sampling schedule was not sufficient to adequately cover an assumed half-life of 50 hours which was observed in Part A of the trial. A total of 3.5 mL blood was collected in potassium EDTA tubes and 3.5 mL in coagulation tubes.

The protocol stated that patients could be administered a second dose of $^{186}$Re-BIWA 4 after having determined the MTD. This procedure was modified by amendment 2. Patients were considered eligible for a second treatment cycle in case they responded to the first administration of $^{186}$Re-BIWA 4, were free of or had recovered from adverse events and had no HAHA antibodies. Response was defined as stable disease (i.e. no change), partial remission or complete remission. The second dose administered was always 50 mCi/m$^2$. Due to the change in the linker the trial was concluded before having investigated a second dose with the dosing regimen described in the protocol. To allow patients who responded to be treated anyhow, amendment 2 was issued.

The trial was completed and terminated after having reached the MTD due to the change of the linker. MAG3 will be replaced by MAG2GABA-TFP in the future development of the BIWA 4 project.

Samples were available for sCD44v6 determination for more time points than originally planned.

The following changes were made after having evaluated the data and after discussion within the trial team.

The ratio of % ID/kg tumour versus % ID/kg non-tumour tissue was performed for bone marrow only, due to the variability of the results.

The same holds true for the evaluation of the tumour size. Measurements were incomplete thus jeopardising a reasonable evaluation. Therefore, no formal analysis was done.

Study Subjects

Disposition of Subjects

Of the 33 patients screened three patients discontinued the trial due to adverse events before administration of the trial drug (TABLE 6.1:1). These three patients are not included in the analyses. A total of 30 patients were entered and treated in this trial.

Part A

Ten patients of the 30 patients treated were included in Part A with 3 each receiving 25 mg and 100 mg $^{99m}$Tc-BIWA 4, respectively, while four patients received 50 mg $^{99}$Tc-BIWA 4. All patients in Part A completed the trial.

Part B

Two out of the 20 patients treated in Part B discontinued due to adverse events (two patients died). Three patients were administered a second dose of 50 mCi/m$^2$.

TABLE 6.1: 1

Disposition of Patients

| | Part A $^{99m}$Tc-BIWA 4 | | | Part B $^{186}$Re-BIWA 4 [mCi/m$^2$] | | | | | |
|---|---|---|---|---|---|---|---|---|---|
| | 25 mg BIWA 4 | 50 mg BIWA 4 | 100 mg BIWA 4 | 20 | 30 | 40 | 50 | 60 | Total |
| Screened | | | | | | | | | 33 |
| Entered | 3 | 4 | 3 | 2 | 4 | 3 | 6 | 5 | 30 |
| Treated | 3 | 4 | 3 | 2 | 4 | 3 | 6 | 5 | 30 |
| Completed | 3 | 4 | 3 | 2 | 3 | 2 | 6 | 5 | 28 |
| Discontinued | 0 | 0 | 0 | 0 | 1 | 1 | 0 | 0 | 2 |
| due to AE | 0 | 0 | 0 | 0 | 1 | 1 | 0 | 0 | 2 |
| due to lack of efficacy | 0 | 0 | 0 | 0 | 0 | 0 | 0 | 0 | 0 |
| due to other reason | 0 | 0 | 0 | 0 | 0 | 0 | 0 | 0 | 0 |

TABLE 6.1: 1-continued

Disposition of Patients

| | Part A $^{99\,m}$Tc-BIWA 4 | | | Part B $^{186}$Re-BIWA 4 [mCi/m$^2$] | | | | | |
|---|---|---|---|---|---|---|---|---|---|
| | 25 mg | 50 mg | 100 mg | | | | | | |
| | BIWA 4 | BIWA 4 | BIWA 4 | 20 | 30 | 40 | 50 | 60 | Total |

Source Appendix 16.1.9.2 TABLE 1.1
Protocol Deviations

The majority of protocol violations were deviations (>±10%) from the time windows provided in the protocol concerning blood and/or urine sampling. The patients affected were not excluded from the analyses but the actual times of collecting blood or urine were used for determination of blood, plasma, serum and urine concentrations.

Efficacy/clinical Pharmacology Evaluation

Results from Part A confirmed a dose of 50 mg BIWA 4 as the optimal dose for treatment. Data from Part B indicate that patients may clinically benefit from $^{186}$Re-BIWA4 therapy at a radiation dose below that dose at which DLT was observed.

Concentrations of BIWA 4 measured were dose-proportional and a moderate amount of the dose administered was excreted via the kidneys.

Data Sets Analysed

All patients who had received at least one dose of the trial drug were included in the intent-to-treat analysis. Seven patients from Part A were included in the per protocol analysis. No per protocol analysis was performed for Part B.

Demographics and Other Baseline Characteristics

The mean age of all patients included was 56 years (range 37 to 78). Nineteen patients were males and eleven were females (TABLE 5.2:1).

Three patients treated in Part A never smoked while seven were current smokers (pack years range 19–47). Frequent alcohol consumption was ported in eight patients while two were non drinkers (TABLE 5.2:1).

All patients in Part B were either ex-smokers or current smokers (TABLE 5.2:1) with a mean pack-year of 35 (range 10 to 86). Six patients were non-drinkers while the remaining patients were frequent consumers of alcohol (TABLE 5.2:1).

Stage of the disease was local operable for all patients included in Part A while patients from Part B had recurrent disease (15 patients) and/or metastases (3 patients). One patient had local inoperable disease. In one patient the information is missing.

Concomitant diseases or relevant medical history were reported in 28 patients (TABLE 5.2:1). Concomitant therapy was required by all patients. The most often used medications were analgesics, sedatives, lactulose, H$_2$-blockers, anti-emetics and antimicrobial agents.

TABLE 5.2: 1

Demographics and baseline characteristics. Given are means for age. All other figures denote numbers of patients

| | Part A $^{99\,m}$Tc-BIWA 4 | | | Part B $^{186}$Re-BIWA 4 [mCi/m$^2$] | | | | | |
|---|---|---|---|---|---|---|---|---|---|
| | 25 mg | 50 mg | 100 mg | | | | | | |
| | BIWA 4 | BIWA 4 | BIWA 4 | 20 | 30 | 40 | 50 | 60 | Total |
| n | 3 | 4 | 3 | 2 | 4 | 3 | 6 | 5 | 30 |
| age [mean] | 45.7 | 58.5 | 58.7 | 57.0 | 61.0 | 53.0 | 57.0 | 60.4 | 56.4 |
| male/female | 2/1 | 2/2 | 1/2 | 1/1 | 3/1 | 2/1 | 5/1 | 3/2 | 19/11 |
| conc. disease | 3 | 3 | 2 | 2 | 4 | 3 | 6 | 5 | 28 |
| concom. therapy | 3 | 4 | 3 | 2 | 4 | 3 | 6 | 5 | 30 |
| smoker | 2 | 4 | 1 | 0 | 1 | 0 | 3 | 1 | 12 |
| ex-smoker | 0 | 0 | 0 | 2 | 3 | 3 | 3 | 4 | 15 |
| Alcohol yes | 3 | 3 | 2 | 0 | 3 | 3 | 6 | 2 | 22 |

Initial diagnosis of disease was known in patients from Part A about one month before inclusion while patients included in Part B were ill since two years on average (range 0.1 to 17.5 years; TABLE 5.2:2). The Karnofsky score ranged from 70 to 100 in patients from Part A. Patients from Part B had Karnofsky scores of 70 to 90 (TABLE 5.2:2).

Metastases at diagnosis were reported for one patient in Part B of the trial.

All patients in Part B had undergone previous radio- and/or chemotherapy while patients in Part A had neither previous chemo- nor radiotherapy reported (TABLE 5.2:2). Cisplatin, methotrexate and fluorouracil were the most often systemic anticancer drugs used).

Previous surgery was radical in eleven of the 13 patients in Part B who had a previous surgery. Only one patient from Part A, had undergone previous surgery (TABLE 5.2:2).

Lesion sizes (including metastases) of the tumours ranged from 14 mm$^2$ to 10304 mm$^2$. The primary tumour site was moderately differentiated in the majority of the patients. Lymph nodes were affected in 13 patients (TABLE 5.2:2).

TABLE 5.2: 2

Demographics and baseline characteristics. Given are means for years of known disease and Karnofsky score. All other figures denote numbers of patients

| | Part A $^{99m}$Tc-BIWA 4 | | | Part B $^{186}$Re-BIWA 4 [mCi/m$^2$] | | | | |
|---|---|---|---|---|---|---|---|---|
| | 25 mg BIWA 4 | 50 mg BIWA 4 | 100 mg BIWA 4 | 20 | 30 | 40 | 50 | 60 |
| n | 3 | 4 | 3 | 2 | 4 | 3 | 6 | 5 |
| years of known disease | 0.11 | 0.08 | 0.07 | 9.30 | 2.13 | 1.17 | 0.80 | 1.16 |
| Karnofsky score | 90 | 90 | 100 | 80 | 75 | 76.7 | 85 | 80 |
| radical surgery | 0 | 0 | 0 | 2 | 2 | 1 | 2 | 4 |
| lymph nodes affected | 2 | 2 | 0 | 2 | 3 | 2 | 1 | 1 |
| previous chemotherapy | 0 | 0 | 0 | 1 | 3 | 1 | 4 | 1 |
| previous radiotherapy | 0 | 0 | 0 | 2 | 4 | 3 | 6 | 5 |

All medication was administered under the supervision of the investigator or his/her delegate. Blood was collected to determine the pharnacokinetics of BIWA 4. All patients had detectable blood levels of BIWA 4.

Efficacy/Clinical Pharmacology Results

Three out of six patients experienced stable disease at the maximum tolerated dose of 50 mCi/m$^2$. The dose of 50 mg BIWA 4 was confirmed in Part A of the trial to be the optimal dose concerning blood concentrations and selective tumour uptake . The plasma concentrations of BIWA 4 were dose-proportional in the range of 25 mg to 100 mg BIWA 4 in Part A and peaked at 0.9 hours with a terminal elimination half-life of 54–74 hours and 94 hours for Part A and Part B, respectively.

Analysis of Efficacy/pharmacodynamics

Primary Endpoints

Primary endpoint for efficacy was the biodistribution of $^{99m}$Tc-BIWA 4 in Part A. Further primary endpoints were the analyses of the radioimmunoscintigraphic images and the pharmacokinetics (described in section 5.4.2) for Part A and B of the trial, respectively. Dosimetry was done for Part B only.

Biodistribution of $^{99m}$Tc-BIWA 4 in Part A

Tissue samples were obtained during surgery and the uptake of $^{99m}$Tc-BIWA 4 expressed as % injected dose (ID)/kg tissue.

Intent-to-treat (ITT) subset: The relative biodistribution of $^{99m}$Tc-BIWA 4 was highest in the tumour in all three dosing groups except for patient 1 (25 mg BIWA 4), patient 5 (50 mg BIWA 4, no tumour cells) and patient 9 (100 mg BIWA 4), respectively. The uptake in turnour ranged from 6 to 17% ID/kg, 5 to 28% ID/kg and 13 to 17% ID/kg for the dose group 25 mg, 50 mg and 100 mg, respectively. The calculated mean ratio of tumour uptake versus uptake in bone marrow was 1.7, 2.6 and 2 in the 25 mg, 50 mg and 100 mg dose group, respectively, (TABLES 7.2:1 and 7.2:2).

Per-protocol (PP) subset: The relative biodistribution of $^{99m}$Tc-BIWA 4 was highest in the tumour in all three dosing groups except for patient 1 (25 mg BIWA 4). The uptake in tumour ranged from 6 to 17% ID/kg, 23 to 28% ID/kg and 16% ID/kg for the dose group 25 mg, 50 mg and 100 mg, respectively. The calculated mean ratio of tumour uptake versus uptake in bone marrow was 1.7, 3.2 and 2.5 in the 25 mg, 50 mg and 100 mg dose group, respectively, (TABLES 7.2:1 and 7.2:3).

A trend to greater uptake with smaller tumour size appeared to be present for the 25 mg BIWA 4 dose group. A similar evaluation was not possible for the 50 mg and 100 mg BIWA 4 dose groups due to the limited number of patients (TABLE 7.2:4).

High % ID/kg uptake was observed in bone marrow supernatant (up to 17% ID/kg) and plasma or blood (up to 13% ID/kg) which was always below the uptake in the tumour in the per protocol population except for patient 1 (25 mg BIWA 4). Uptake in skin and mucosa was always below the uptake in primary tumour in the per protocol subset.

Radioimmunoscintigraphic Images of $^{99m}$Tc-BIWA 4 in Part A

While no radioactivity uptake was found in the tumour directly after infusion, a medium uptake of 1.9 was recorded after 21 hours. Uptake of radioimmunoconjugate appeared to be low in bone marrow and kidney both directly after infusion and 21 hours after infusion. Uptake was low to medium in lung while liver revealed a higher uptake.

A similar pattern was observed for the per protocol population. The only difference appeared to be a higher uptake in kidney while the uptake was lower in lung as compared to the intent-to-treat population.

Radioimmunoscintigraphic Images of $^{186}$Re-BIWA 4 in Part B

Radioiummunoscintigraphic examinations were done immediately after infusion and 21, 48, 72, 144 and 336 hours after infusion. Hardly any uptake in tumour was observed directly after the infusion. Relative uptake in tumour appeared to be dose-dependent and increased over time reaching medium and high uptake after 72 to 144 hours with a decline after 336 hours.

Biodistribution of radioactivity was similar in bone marrow, lung, liver, kidney and intestine and did not reveal the same dose dependent effect (except for the intestine). Moreover, relative uptake of radioactivity appeared to be constant or modestly decreased over time and was similar for all doses of radioactivity. Uptake in bone marrow was lowest for most treatment groups.

Secondary Endpoint(s)

Secondary endpoints of efficacy were tumour response to therapy in Part B and the level of CD44v6 expression in tumour in Part A, respectively. Soluble CD44v6 expression was determined for both Part A and Part B of the trial.

CD44v6 Expression in Tumour in Part A

Data of determination of CD44v6 antigen expression is available for seven patients. CD44v6 antigen expression was observed in more than 90% and 80% of the tumour cells in five and two patients, respectively, while CD44v6 antigen expression was detected in more than 90% of the cells of lymph node metastases in the four patients for which lymph node was available for evaluation. Homogenous CD44v6 antigen expression was observed in all patients in the mucosa.

Tumour Response in Part B

Patients treated with doses of up to 40 mCi/m² $^{186}$Re-BIWA 4 did not experience a clinical tumour response. All patients experienced progressive disease. One patient was not evaluable due to intercurrent death.

Three of the six patients treated with 50 mCi/m² $^{186}$Re-BIWA 4 developed stable disease or no change after the first cycle. Two of these three patients who were treated with another cycle with 50 mCi/M² $^{186}$Re-BIWA 4 had progressive disease after the second cycle. Progressive disease was observed after a total of 148 days (patient 109) and 127 days (patient 116) after first administration of the trial drug, respectively.

One patient treated with 60 mCi/M² $^{186}$Re-BIWA 4 experienced stable disease after the first cycle. This patient went into progressive disease after a second cycle with 50 mCi/m² $_{186}$Re-BIWA 4 (173 days after the first administration of the trial drug).

The overall time to progression for patients who did not respond to therapy ranged from 0 to 55 days with a mean of about five to six weeks irrespective of the treatment group.

Soluble CD44v6 in Part A and B

Soluble CD44v6 was determined in all patients treated with BIWA 4 in the present trial.

The amount of soluble CD44v6 detected tended to increase for the $^{186}$Re-BIWA 4 treated patients (TABLE 7.2:6) during the trial in Part B while for patients treated with $^{99m}$Tc in Part A no such trend could be observed.

Drug Dose, Drug Concentration, and Relationship to Response

The pharmacokinetics of BIWA 4 will be presented separately for Parts A and B because the radiolabel was different (Part A: $^{99m}$Tc; Part B: $^{186}$Re).

5.4.2.1 Analytical Performance with Regard to BIWA 4, HAHAs and CD44v6

Validated assays were used for analysis of plasma samples. Analysis of quality control samples produced results of high accuracy and precision.

Analytical Performance with Regard to Gamma Counting of Samples

The signal linearity of the scintillation crystal in the gamma counter was not tested. It can be assumed based on the type of instrument at least in the energy range that was used in the current study. Calibration samples showed typically 40000–200000 counts per minute vs less than 50–100 counts per minute in background samples. The precision of the seven measurements per calibration standard was regularly within 2%. The same applies for the precision of the individual triplicate measurements in blood, serum and urine. Blood and serum samples showed typically activities between 2000 and 100000 counts per minute.

There were no quality control samples for radioactivity counting. The precision of repeated measurements of calibration standards and samples derived from the current study indicate that the precision of triplicate measurements was at least better than 2%.

Pharmacokinetics

Part A.

Part A consisted of 10 patients receiving a single BIWA 4 dose ranging from 25 to 100 mg with a constant radiolabelled dose of 20 mCi $^{99m}$Tc. The pharmacokinetic parameters in plasma for BIWA 4 measured by ELISA following a short intravenous infusion are given in TABLE 5.4.2.2:1.

TABLE 5.4.2.2: 1

Pharmacokinetic parameters for BIWA 4 in plasma from Part A of the study

| Patient | BIWA 4 Dose (mg) | tmax (min) | Cmax (ng/mL) | Half-Life (h) | $AUC_{inf}$ (ug · h/mL) | Vz (L) | CL (mL/min) | MRT (h) |
|---|---|---|---|---|---|---|---|---|
| 1 | 25 | 0 | 6634 | 44.1 | 387.4 | 4.1 | 1.076 | 58.0 |
| 2 | 25 | 30 | 6640 | 67.0 | 534.7 | 4.5 | 0.779 | 94.8 |
| 3 | 25 | 10 | 9590 | 53.3 | 542.9 | 3.5 | 0.768 | 71.0 |
| 4 | 50 | 29 | 14900 | 64.9 | 1112.3 | 4.2 | 0.749 | 84.8 |
| 5 | 50 | 121 | 15500 | 102.8 | 1580.2 | 4.7 | 0.527 | 135.2 |
| 8 | 50 | 5 | 13900 | 53.0 | 831.0 | 4.6 | 1.003 | 71.7 |
| 10 | 50 | 41 | 16700 | 83.8 | 1461.6 | 4.1 | 0.570 | 110.0 |
| 6 | 100 | 4 | 30500 | 85.0 | 2548.9 | 4.8 | 0.654 | 112.0 |
| 7 | 100 | 17 | 30600 | 76.0 | 2709.6 | 4.0 | 0.615 | 110.4 |
| 9 | 100 | 30 | 24500 | 44.6 | 1708.1 | 3.8 | 0.976 | 61.1 |
| Geometric mean | | | | | | | | |
| | 25 mg | | 7503 | 54.0 | 482.7 | 4.0 | 0.863 | 73.1 |
| | 50 mg | 29 | 15216 | 73.8 | 1208.8 | 4.4 | 0.689 | 97.5 |
| | 100 mg | 13 | 28383 | 66.0 | 2276.4 | 4.2 | 0.732 | 91.1 |

The increase in $C_{max}$ BIWA 4 plasma concentrations observed and the area under the curve were proportional to the dose administered (FIGS. 4 and 5).

Serum concentrations of the radiolabel ($^{99m}Tc$) were also determined and the pharmacokinetic parameters are presented in TABLE 5.4.2.2:2.

Graphically, there was consistency between plasma BIWA 4 concentrations and serum radioactivity concentrations for each patient and within the three patients that received $^{186}Re$-BIWA 4 on two occasions. This consistency observed graphically contrasts with the perception of a longer half-life for radioactivity when the data was modelled

TABLE 5.4.2.2: 2

Pharmacokinetic parameters for $^{99m}Tc$-BIWA 4 in serum from Part A of the study

| Patient | $^{99m}Tc$-BIWA 4 Dose (mCi) | Tmax (min) | Cmax (% ID/kg) | Half-Life (h) | $AUC_{inf}$ (% ID · h/kg) | Vz (kg) | CL (kg/min) | MRT (h) |
|---|---|---|---|---|---|---|---|---|
| 1 | 19.0 mCi | 117 | 52.66 | 44.6 | 3376.9 | 1.9 | 0.030 | 63.8 |
| 2 | 20.0 mCi | 10 | 28.08 | 55.6 | 2151.7 | 3.7 | 0.048 | 79.1 |
| 3 | 21.4 mCi | 10 | 39.11 | 27.5 | 1445.3 | 2.7 | 0.072 | 41.5 |
| 4 | 19.5 mCi | 29 | 31.84 | 31.3 | 1432.8 | 3.2 | 0.072 | 43.8 |
| 5 | 19.1 mCi | 121 | 32.29 | 39.6 | 1934.8 | 3.0 | 0.054 | 56.3 |
| 8 | 18.8 mCi | 114 | 28.41 | 42.8 | 1620.1 | 3.8 | 0.060 | 60.8 |
| 10 | 19.3 mCi | 41 | 40.31 | 43.1 | 2247.1 | 2.8 | 0.042 | 62.3 |
| 6 | 19.3 mCi | 120 | 30.45 | 45.3 | 1946.5 | 3.4 | 0.054 | 65.2 |
| 7 | 19.8 mCi | 77 | 35.79 | 36.0 | 1628.6 | 3.2 | 0.060 | 51.1 |
| 9 | 18.3 mCi | 238 | 31.94 | 35.5 | 1805.6 | 2.8 | 0.054 | 50.6 |
| Harmonic mean | | | | 38.7 | | | | |
| Geometric mean | | 57.9 | 34.5 | 39.4 | 1898.0 | 3.0 | 0.053 | 56.5 |

The geometric mean half-life for BIWA 4 measured by ELISA in plasma following intravenous infusion ranged from 54 to 73.8 hours for the three treatment groups studied in Part A. The geometric mean half-life for the $^{99m}Tc$-radiolabeled BIWA 4 for the same samples was shorter at 39.4 hours in serum and 46.4 hours in blood. The discrepancy between the two mean estimates was attributed to longer sampling times possible with BIWA 4 due to radioactivity assay restrictions.

Radioactivity was excreted into the urine in the amounts collected in TABLE 5.4.2.2:3. Due to incomplete collections over the 48 hours (i.e. cumulative data may not always be comparable because of varying duration of collection), no further assessment was made of this urinary excretion data. For six patients with complete 48-hour collections, the mean amount of radioactivity collected was 10% of the initial dose.

TABLE 5.4.2.2: 3

Amount of radioactivity ($^{99m}Tc$) excreted (as percent of initial dose) into urine in Part A

| | Collection Interval (h) | | | | | Cumulative |
|---|---|---|---|---|---|---|
| Patient | 0–4 | 4–8 | 8–12 | 12–24 | 24–48 | Amount (% ID) |
| 1 | 2.80 | 10.13 | 5.08 | n.a. | n.a. | 18.01 |
| 2 | 1.94 | 0.97 | 0.52 | 3.09 | 3.23 | 9.75 |
| 3 | 0.29 | 1.44 | 1.19 | n.a. | n.a. | 2.92 |
| 4 | 1.68 | 1.42 | 1.95 | 1.14 | 2.21 | 8.40 |
| 5 | 2.20 | 1.60 | 1.02 | 3.96 | 3.98 | 12.76 |
| 8 | 1.29 | 2.45 | 0.88 | 3.67 | 3.00 | 11.29 |
| 10 | n.a. | n.a. | n.a. | n.a. | n.a. | |
| 6 | 2.55 | 1.59 | 1.80 | 1.89 | 2.00 | 9.83 |
| 7 | n.a. | 3.14 | n.a. | 1.79 | 3.13 | 8.06 |
| 9 | 1.54 | 3.34 | 0.00 | 1.05 | 2.31 | 8.24 | n.a. = not applicable, no data available

Part B:

Part B consisted of 20 patients receiving BIWA 4 doses of 50 mg with varying radiolabelled doses of $^{186}Re$-BIWA 4 ranging from 20–60 mCi/M². Three patients received a second intravenous infusion while the other 17 patients received only a single course of therapy.

(noncompartmental evaluation). The geometric mean half-life of 122 hours for the radioactive portion of the $^{186}Re$-BIWA 4 was longer than the ELISA-determined plasma half-life of 94 hours for BIWA 4.

Grouping (TABLES 5.4.2.2:6 and 5.4.2.2:7) the pharmacokinetic parameters by amount of radioactivity administered showed some trends of longer exposure with increased radioactivity dosed, but the numbers of individuals in each dose group are too small to make any consistent conclusions.

TABLE 5.4.2.2: 6

Geometric means for plasma BIWA 4 pharmacokinetic parameters grouped by amount of radioactivity given.

| $^{186}Re$ Dose (mCi/m²) | n | Cmax (ng/mL) | Half-Life (h) | $AUC_{inf}$ (µg · h/mL) | Vz (L) | CL (mL/h) | MRT (h) |
|---|---|---|---|---|---|---|---|
| 20 | 2 | 12160 | 106.5 | 1217 | 6.3 | 41.1 | 130.3 |
| 30 | 4 | 15239 | 86.2 | 1399 | 4.4 | 35.7 | 116.2 |
| 40 | 3 | 11121 | 90.6 | 1201 | 5.4 | 41.7 | 125.1 |
| 50 | 9* | 12982 | 92.4 | 1055 | 6.3 | 47.4 | 117.4 |
| 60 | 5 | 11927 | 99.8 | 939 | 7.7 | 53.2 | 115.9 |

*patients who received two doses of 50 mCi/m² are included

TABLE 5.4.2.2:7

Geometric means for serum $^{186}Re$-BIWA 4 pharmacokinetic parameters grouped by amount of radioactivity given.

| $^{186}Re$ Dose (mCi/m²) | n | Cmax (% ID/kg) | Half-Life (h) | $AUC_{inf}$ (% ID · h/kg) | Vz (kg) | CL (kg/h) | MRT (h) |
|---|---|---|---|---|---|---|---|
| 20 | 2 | 30.88 | 114.4 | 3296 | 5.01 | 0.030 | 154.6 |
| 30 | 4 | 40.09 | 98.8 | 4365 | 3.27 | 0.023 | 134.5 |
| 40 | 3 | 28.82 | 126.4 | 3856 | 4.73 | 0.026 | 172.4 |
| 50 | 9* | 40.22 | 123.3 | 4182 | 4.25 | 0.024 | 162.5 |
| 60 | 4 | 32.10 | 145.2 | 3493 | 6.00 | 0.029 | 185.5 |

*patients who received two doses of 50 mCi/m² are included

Pharmacokinetic/pharmacodynamic Analysis

A pharmacokinetic/pharmacodynamic analysis was not performed.

Statistical/analytical Issues

The analysis was performed as originally planned. Details are described in section 3.7.1.3.

Primary Endpoint(s)

Not applicable.

Secondary Endpoint(s)

Not applicable.

Drug-drug and Drug-disease Interactions

No tests concerning drug-drug or drug-disease interactions were done.

By-subject Displays

For details see section 6.4.2.2 and 6.4.2.3.

Efficacy/clinical Pharmacology Conclusions

Part A:

Results from Part A confirmed a dose of 50 mg BIWA 4 as the optimal dose for treatment based on blood concentrations and tissue uptake level. The distribution as assessed by radioscintigraphy and biopsy measurements was in almost all cases highest in the tumour as compared to other tissues. Uptake of radioactivity increased in the tumour over time. CD44v6 expression was present in more than 80 % and 90% of the cells of primary tumour and lymph node metastases, respectively, and in all mucosa specimens obtained.

The amount of soluble CD44v6 appeared to be constant before and after $^{99m}$Tc-BIWA 4 administration.

Concentrations of BIWA 4 measured were dose-proportional in the range of 25 mg to 100 mg BIWA 4. A moderate amount of the dose administered was excreted via the kidneys. The % ID excreted in urine was similar for all dosing groups.

Part B:

Data from Part B indicate that patients may clinically benefit from $^{186}$Re-BIWA 4 therapy at MTD. One out of five patients treated with 60 mCi/m$^2$ had stable disease. Three out of six patients experienced stable disease at the maximum tolerated dose of 50 mCi/m$^2$. Time until progression ranged between 127 and 173 days in those patients who received a second dose of 50 mCi/m$^2$. Radioimmunoscintigraphy indicates uptake of radioactivity in tumour tissue. Biodistribution was comparable in other tissues irrespective of dose. Dosimetric analysis did not reveal unexpected high absorbed doses in tissues other than the tumour except for the testes. However, the relevance of the observed testes dose for the impairment of fertility is currently unclear.

The amount of soluble CD44v6 detected tended to increase for the $^{186}$Re-BIWA 4 treated patients.

The plasma concentrations of BIWA 4 peaked at 0.92 hours and the antibody was eliminated with a geometric mean half-life of 94 hours for BIWA 4 determined by ELISA. $C_{max}$ and AUC values (ELISA measurement) were similar to those obtained in Part A of the trial for the 50 mg BIWA 4 dose group.

Safety Evaluation

Dose limiting toxicity occurred at a dose of 60 mCi/m$^2$ while a dose of 50 mCi/m$^2$ $^{186}$Re-BIWA 4 turned out to be the maximum tolerated dose in the present trial. The dose limiting toxicity were adverse events from the bone marrow i.e. thrombocytopenia and leucopenia.

Extent of Exposure

All ten patients treated in Part A of the trial were administered one single dose of $^{99m}$Tc-BIWA 4. Doses of BIWA 4 were either 25 mg, 50 mg or 100 mg while $^{99m}$Tc was 20 mCi.

In Part B, 20 patients were administered one single dose of $^{186}$Re-BIWA 4. Three patients received a second dose of 50 mCi/m$^2$ due to stable disease (no change). The dose of BIWA 4 was kept stable at 50 mg while the radioactivity of $^{186}$Re was increased in 10 mCi/m$^2$ body surface increments.

The dose was calculated according to body surface area (TABLE 6.1:1).

TABLE 6.1:1

Mean dose of radioactivity administered

| | Part A $^{99m}$Tc-BIWA 4 | | | Part B $^{186}$Re-BIWA 4 [mCi/m$^2$] | | | | |
|---|---|---|---|---|---|---|---|---|
| | 25 mg BIWA 4 | 50 mg BIWA 4 | 100 mg BIWA 4 | 20 | 30 | 40 | 50 | 60 |
| N | 3 | 4 | 3 | 2 | 4 | 3 | 6 | 5 |
| mCi $^{99m}$Tc | 20.1 ± 1.2 | 19.2 ± 0.3 | 19.1 ± 0.8 | n.a | n.a | n.a | n.a | n.a |
| mCi $^{186}$Re | n.a. | n.a | n.a | 33.1 ± 1.7 | 52.4 ± 5.6 | 70.6 ± 5.2 | 87.2 ± 8.5 | 97.2 ± 8.3 | n.a. = not applicable, mean values and standard deviation are given

The radiochemical purity of the drug was more than 95% and the immunoreactive fraction was higher than 80%.

An observation period of at least 6 weeks followed the administration of the trial drug.

Adverse Events (AES)

Adverse events were reported in all patients treated. Two patients discontinued the observation period in Part B due to an AE. No action was taken with the trial drug since treatment had been completed.

Brief Summary of Adverse Events

Part A:

The majority of patients in Part A experienced adverse events from body as a whole (50%) which may be also due to the underlying surgery and the associated pain. No special pattern of adverse events was reported and none of the patients developed CTC criteria 3 or 4 which were judged to be drug-related (TABLES 6.2.2:1 and 2).

Three patients experienced serious adverse events which are described in section 6.3.1.

Part B:

Adverse events of the system organ class (SOC) 'body as a whole' were reported in 65% of the patients, followed by adverse events from the system organ class 'platelet, bleeding and clotting disorders' (60% of the patients) and 'white cell and reticulo endothelial system disorders' (50% of the patients). Drug-related thrombocytopenias and leucopenias occurred in 11 (55%) and 10 (50%) patients on average 21 days after start of radioimmunotherapy and were generally reversible after 6 weeks. A dose-response was observed for these events (TABLE 6.2.2:3).

Haematological dose-limiting toxicity defined as drug-related CTC grade 4 was reported in three patients.

Non-haematological dose-limiting toxicity defined as drug-related CTC grade 3 or 4 non-haematological toxicity occurred in 4 patients (at 30 mCi/m$^2$ one patient experienced rash and Quincke's oedema, two patients experienced fever at 60 mCi/m$^2$ and one patient treated with 60 mCi/m$^2$ experienced fatigue.

Six of the nine patients who experienced serious adverse events died. Deaths and serious adverse events are described in section 12.3.1.

Display of Adverse Events

Part A:

The following adverse events sorted by SOC, preferred term and the three dose groups of BIWA 4 were reported in more than one patient in Part A of the trial (TABLE 6.2.2:1). More details as well as the preferred terms can be found in section 7.3.1.

TABLE 6.2.2: 1

Patients with adverse events in Part A (pre-surgical treatment with a single dose of 20 mCi $^{99m}$Tc-BIWA 4)

| | $^{99m}$Tc-BIWA 4 | | | |
| --- | --- | --- | --- | --- |
| | 25 mg BIWA 4 | 50 mg BIWA 4 | 100 mg BIWA 4 | total |
| number of patients (% of patients treated) | 3 (100) | 4 (100) | 3 (100) | 10 (100) |
| number of patients with any adverse event | 3 (100) | 4 (100) | 3 (100) | 10 (100) |
| application site disorders | 2 (66.7) | 0 (0) | 0 (0) | 2 (20.0) |
| body as a whole | 2 (66.7) | 2 (50.0) | 1 (33.3) | 5 (50.0) |
| Pain | 1 (33.3) | 1 (25.0) | 1 (33.3) | 3 (30.0) |
| central and peripheral nervous system | 1 (33.3) | 1 (25.0) | 0 (0) | 2 (20.0) |
| metabolic and nutritional disorders | 1 (33.3) | 2 (50.0) | 1 (33.3) | 4 (40.0) |
| weight decrease | 1 (33.3) | 1 (25.0) | 0 (0) | 2 (20.0) |
| resistance mechanism disorder | 0 (0) | 4 (100) | 0 (0) | 4 (40.0) |
| Infection | 0 (0) | 3 (75.0) | 0 (0) | 3 (30.0) |
| vascular disorders | 1 (33.3) | 1 (25.0) | 1 (33.3) | 3 (30.0) |
| Haemorrhage (not specified) | 1 (33.3) | 1 (25.0) | 0 (0) | 2 (20.0) | given are SOCs and preferred terms in case they were reported in more than one patient; figure in brackets denote percentage of patients treated The events which were considered drug-related by the investigator graded according to CTC criteria are listed in TABLE 6.2.2:2. The events were grade 1 according to CTC.

TABLE 6.2.2: 2

Severity of drug-related (as judged by the investigator) adverse events according to CTC criteria reported in Part A (pre-surgical treatment with a single dose of 20 mCi $^{99m}$Tc-BIWA 4).

| | $^{99m}$Tc-BIWA 4 | | | |
| --- | --- | --- | --- | --- |
| | 25 mg BIWA 4 | 50 mg BIWA 4 | 100 mg BIWA 4 | total |
| number of patients | 3 | 4 | 3 | 10 |
| Number of adverse events considered drug-related | 0 | 2 | 0 | 2 |
| Liver and biliary system disorder | 0 | 2 | 0 | 2 |
| sGOT increased | 0 | 1 | 0 | 1 |
| sGPT increased | 0 | 1 | 0 | 1 | sGOT = serum glutamic oxalacetic transaminase;
sGPT = serum glutamic pyruvic transaminase Part B:

TABLE 6.2.2:3 presents the number of patients with adverse events sorted by SOC, preferred term and the radiation dose groups of $^{186}$Re-BIWA 4.

TABLE 6.2.2:3

Patients with adverse events occurring in Part B (treatment with $^{186}$Re-BIWA 4 first and second doses considered)

| | $^{186}$Re-BIWA 4 [mCi/m$^2$] | | | | | |
|---|---|---|---|---|---|---|
| | 20 | 30 | 40 | 50 | 60 | total |
| number of patients treated | 2 (100) | 4 (100) | 3 (100) | 6 (100) | 5 (100) | 20 (100) |
| number of patients with adverse events | 2 (100) | 4 (100) | 3 (100) | 6 (100) | 5 (100) | 20 (100) |
| body as a whole | 2 (100) | 3 (75.0) | 2 (66.7) | 2 (33.3) | 4 (80.0) | 13 (65.0) |
| allergic reaction | 0 (0) | 1 (25.0) | 0 (0) | 0 (0) | 1 (20.0) | 2 (10.0) |
| Fatigue | 0 (0) | 0 (0) | 0 (0) | 1 (16.7) | 1 (20.0) | 2 (10.0) |
| Fever | 0 (0) | 0 (0) | 2 (66.7) | 0 (0) | 2 (40.0) | 4 (20.0) |
| oedema mouth | 1 (50.0) | 0 (0) | 0 (0) | 1 (16.7) | 0 (0) | 2 (10.0) |
| Pain | 0 (0) | 2 (50.0) | 0 (0) | 1 (16.7) | 1 (20.0) | 4 (20.0) |
| central and peripheral nervous system disorder | 0 (0) | 1 (25.0) | 2 (66.7) | 1 (16.7) | 0 (0) | 4 (20.0) |
| gastro-intestinal system disorder | 0 (0) | 1 (25.0) | 1 (33.3) | 2 (33.3) | 3 (60.0) | 7 (35.0) |
| Mucositis | 0 (0) | 0 (0) | 0 (0) | 1 (16.7) | 3 (60.0) | 4 (20.0) |
| Stomatitis | 0 (0) | 0 (0) | 0 (0) | 1 (16.7) | 1 (20.0) | 2 (10.0) |
| liver and biliary system disorders | 1 (50.0) | 0 (0) | 0 (0) | 0 (0) | 1 (20.0) | 2 (10.0) |
| sGPT increased | 1 (50.0) | 0 (0) | 0 (0) | 0 (0) | 1 (20.0) | 2 (10.0) |
| metabolic and nutritional disorders | 1 (50.0) | 0 (0) | 1 (33.3) | 1 (16.7) | 1 (20.0) | 4 (20.0) |
| Neoplasm | 0 (0) | 0 (0) | 2 (66.7) | 0 (0) | 2 (40.0) | 4 (20.0) |
| neoplasm malignant aggravated | 0 (0) | 0 (0) | 1 (33.3) | 0 (0) | 2 (40.0) | 3 (15.0) |
| platelet, bleeding and clotting disorders | 0 (0.0) | 1 (25.0) | 1 (33.3) | 5 (83.3) | 5 (100) | 12 (60.0) |
| Thrombocytopenia | 0 (0.0) | 1 (25.0) | 1 (33.3) | 4 (66.7) | 5 (100) | 11 (55.0) |
| red blood cell disorder | 0 (0) | 0 (0) | 0 (0) | 2 (33.3) | 3 (60.0) | 5 (25.0) |
| Anaemia | 0 (0) | 0 (0) | 0 (0) | 2 (33.3) | 3 (60.0) | 5 (25.0) |
| respiratory system disorder | 0 (0) | 1 (25.0) | 1 (33.3) | 0 (0) | 2 (40.0) | 4 (20.0) |
| Bronchitis | 0 (0) | 1 (25.0) | 0 (0) | 0 (0) | 1 (20.0) | 2 (10.0) |
| Dyspnoea | 0 (0) | 0 (0) | 0 (0) | 0 (0) | 2 (40.0) | 2 (10.0) |
| Rhinitis | 0 (0) | 0 (0) | 1 (33.3) | 0 (0) | 1 (20.0) | 2 (10.0) |
| skin and appendages disorder | 1 (50.0) | 1 (25.0) | 1 (33.3) | 0 (0) | 1 (20.0) | 4 (20.0) |
| Rash | 0 (0) | 1 (25.0) | 0 (0) | 0 (0) | 1 (20.0) | 2 (10.0) |
| white cell and RES disorder | 0 (0) | 0 (0) | 1 (33.3) | 4 (66.7) | 5 (100) | 10 (50.0) |
| Granulocytopenia | 0 (0) | 0 (0) | 0 (0) | 1 (16.7) | 2 (40.0) | 3 (15.0) |
| Leucopenia | 0 (0) | 0 (0) | 1 (33.3) | 4 (66.7) | 5 (100) | 10 (50.0) | given are SOCs and preferred terms in case they were reported in more than one patient;
sGPT = serum glutamic pyruvic transaminase;
RES = reticulo endothelial system, figure in brackets denote percentage of patients treated Drug-related adverse events were reported in 75% of the patients. Drug-related leucopenia was reported in 50% and thrombocytopenia in 55% of the patients, respectively.

Adverse events considered drug-related are provided in TABLE 6.2.2:4 graded according to the CTC.

TABLE 6.2.2:4

Drug-related (as judged by the investigator) adverse events according to CTC criteria reported in Part B (first and second dose considered)

| | | $^{186}$Re-BIWA 4 [mCi/m$^2$] | | | | | |
|---|---|---|---|---|---|---|---|
| adverse event | | 20 | 30 | 40 | 50 | 60 | total |
| CTC grade 1 | | 1 | 0 | 2 | 6 | 5 | 14 |
| | face oedema | 1 | n.a. | 0 | 0 | 0 | 1 |
| | Leucopenia | 0 | n.a. | 1 | 2 | 0 | 3 |
| | Moniliasis | 0 | n.a. | 0 | 0 | 1 | 1 |

TABLE 6.2.2:4-continued

Drug-related (as judged by the investigator) adverse events according to CTC criteria reported in Part B (first and second dose considered)

| | | $^{186}$Re-BIWA 4 [mCi/m$^2$] | | | | | |
|---|---|---|---|---|---|---|---|
| adverse event | | 20 | 30 | 40 | 50 | 60 | total |
| | Mucositis | 0 | n.a. | 0 | 0 | 1 | 1 |
| | platelets abnormal | 0 | n.a. | 0 | 1 | 0 | 1 |
| | Purpura | 0 | n.a. | 0 | 0 | 1 | 1 |
| | Stomatitis | 0 | n.a. | 0 | 1 | 0 | 1 |
| | thrombocytopenia | 0 | n.a. | 1 | 2 | 2 | 5 |
| CTC grade 2 | | 0 | 1 | 0 | 7 | 7 | 15 |
| | Anaemia | n.a. | 0 | n.a. | 1 | 1 | 2 |
| | Gout | n.a. | 0 | n.a. | 1 | 0 | 1 |
| | Leucopenia | n.a. | 0 | n.a. | 1 | 2 | 3 |
| | Mucositis | n.a. | 0 | n.a. | 2 | 3 | 5 |
| | Stomatitis | n.a. | 0 | n.a. | 0 | 1 | 1 |

TABLE 6.2.2:4-continued

Drug-related (as judged by the investigator) adverse events according to CTC criteria reported in Part B (first and second dose considered)

| | | 186Re-BIWA 4 [mCi/m²] | | | | | |
|---|---|---|---|---|---|---|---|
| | adverse event | 20 | 30 | 40 | 50 | 60 | total |
| | taste loss | n.a. | 0 | n.a. | 1 | 0 | 1 |
| | thrombocytopenia | n.a. | 1 | n.a. | 1 | 0 | 2 |
| CTC grade 3 | | 0 | 2 | 0 | 2 | 8 | 12 |
| | allergic reaction | n.a. | 1 | n.a. | 0 | 0 | 1 |
| | Fatigue | n.a. | 0 | n.a. | 0 | 1 | 1 |
| | Fever | n.a. | 0 | n.a. | 0 | 2 | 2 |
| | Leucopenia | n.a. | 0 | n.a. | 1 | 1 | 2 |
| | Rash | n.a. | 1 | n.a. | 0 | 0 | 1 |
| | thrombocytopenia | n.a. | 0 | n.a. | 1 | 4 | 5 |
| CTC grade 4 | | 0 | 0 | 0 | 3 | 5 | 8 |
| | Anaemia | n.a. | n.a. | n.a. | 0 | 1 | 1 |
| | granulocytopenia | n.a. | n.a. | n.a. | 1 | 2 | 3 |
| | Leucopenia | n.a. | n.a. | n.a. | 1 | 2 | 3 |
| | thrombocytopenia | n.a. | n.a. | n.a. | 1 | 0 | 1 | given is the number of adverse events;
n.a. = not applicable

Analysis of Adverse Events

Part A:

None of the adverse events occurring in Part A of the trial were considered drug-related except for one patient experiencing mild and reversible CTC grade 1 elevation of AST and ALT.

No difference in AB profile was observed when comparing the different BIWA 4 doses.

Part B:

Thrombocytopenia and leucopenia were dose-dependent (TABLES 6.2.2:3 and 6.2.2:4) and dose-limiting. Time course is provided in section 6.4.2.1.

Mucositis up to CTC grade two was reported more often with increasing radiation dose without causing dose-limiting toxicity (TABLES 6.2.2:3 and 6.2.2:4).

An allergic reaction was reported in two patients, one experiencing drug-related Quincke's oedema and rash (30 mCi/m²) and one patient (60 mCi/m²) had an allergic reaction after a thrombocyte concentrate transfusion, which was not considered drug-related. One patient 20 mCi/m²) had urticaria which also was not considered drug-related and one patient (20 mCi/m²) experienced drug-related face oedema.

HAHAs were detected in two patients (see section 12.4.3).

Discontinuations due to adverse events occurred in two patients. Both patients died.

Adverse events required initiation of concomitant therapy in 17 patients. These patients are shortly described in section 6.3.1.

Deaths, Other Serious Adverse Events, and Other Significant Adverse Events

Serious adverse events were reported in 12 patients. Of those six patients died in the course of the trial or follow-up. All patients who died were treated in Part B of the trial. None of the patients treated in Part A died. All fatalities were due to disease progression.

Two patients in Part B discontinued the trial prematurely due to adverse events (death in both patient 112 and 105).

Adverse events requiring therapy were most often thrombocytopenia, leucopenia and fever.

Tables, Figures and Graphs Referred to but not Included in the Text

Demographic Data

Details of Demographics are not Included.

Efficacy/pharmacodynamic Data

TABLE 7.2:1 Tumour to bone marrow uptake ratio—Part A of the trial

TABLE 7.2:2 Tumour to bone marrow uptake ratio (ITT subset)—Part A of the trial

TABLE 7.2:3 Tumour to bone marrow uptake ratio (PP subset)—Part A of the trial

TABLE 7.2:4 Tumour size and % uptake of antibody—Part A of the trial (per protocol population)

TABLE 7.2:5 CD44v6 antigen expression in tumour and other tissue—Part A of the trial TABLE 7.2:6 Soluble CD44v6 in serum. Mean values are given in ng/mL

TABLE 7.2: 1

Tumour to bone marrow uptake ratio - Part A of the trial

| | Part A 99mTc-BIWA 4 patient No | uptake tumour (% ID/kg; calculated) | uptake bone marrow (% ID/kg; calculated) | ratio tumour/bone marrow (calculated) |
|---|---|---|---|---|
| 25 mg BIWA 4 | 1* | 6.14 | 5.58 | 1.10 |
| | 2* | 15.78 | 7.49 | 2.11 |
| | 3* | 16.78 | 8.63 | 1.95 |
| 50 mg BIWA 4 | 4* | 28.10 | 6.98 | 4.03 |
| | 8* | 27.76 | 7.57 | 3.67 |
| | 10* | 22.63 | 11.54 | 1.96 |
| 100 mg BIWA 4 | 6* | 15.89 | 6.47 | 2.46 |
| | 7 | 16.99 | 7.70 | 2.21 |
| | 9 | 13.31 | 10.11 | 1.32 |

No = number;
*= included in per protocol analysis;
% ID = % injected dose; calculations were done by taking different weights of samples into account

TABLE 7.2: 2

Tumour to bone marrow uptake ratio (ITT subset) - Part A of the trial

| | Part A 99mTc-BIWA 4 ratio tumour/bone marrow (calculated) |
|---|---|
| 25 mg BIWA 4 | 1.72 |
| 50 mg BIWA 4 | 2.57 |
| 100 mg BIWA 4 | 1.99 | mean values are given; ITT = intent-to-treat; calculations were done by taking different weights of samples into account

TABLE 7.2:3

Tumour to bone marrow uptake ratio (PP subset) - Part A of the trial

| | Part A 99mTc-BIWA 4 ratio tumour/bone marrow (calculated) |
|---|---|
| 25 mg BIWA 4 | 1.72 |
| 50 mg BIWA 4 | 3.22 |
| 100 mg BIWA 4 | 2.46 | mean values are given; PP = per protocol; calculations were done by taking different weights of samples into account

TABLE 7.2:4

4 Tumour size and % uptake of antibody - Part A of the trial (per protocol population)

| | | Part A $^{99m}$Tc-BIWA 4 | |
|---|---|---|---|
| | patient No | tumour size [mm²] | uptake tumour (% ID/kg; calculated) |
| 25 mg BIWA 4 | 1 | 1350 | 6.14 |
| | 2 | 900 | 15.78 |
| | 3 | 225 | 16.78 |
| 50 mg BIWA 4 | 4 | n.a. | 28.10 |
| | 8 | 1504 | 27.76 |
| | 10 | 1400 | 22.63 |
| 100 mg BIWA 4 | 6 | 800 | 15.89 |

No = patient number,
n.a. = not applicable, only length or width given but not length and width; calculations were done by taking different weights of samples into account

TABLE 7.2:5

5 CD44v6 antigen expression in tumour and other tissue - Part A of the trial

| | | Part A $^{99m}$Tc-BIWA 4 | | |
|---|---|---|---|---|
| | patient No | CD44v6 antigen expression in tumour | CD44v6 expression in mucosa | CD44v6 expression in lymph node metastases |
| 25 mg BIWA 4 | 1* | n.a. | n.a. | n.a. |
| | 2* | ++/+++; >80% | +++ | ++/+++; >90% |
| | 3* | +++; >90% | +++ | +++; >90% |
| 50 mg BIWA 4 | 4* | +++; >90% | +++ | +++; >90% |
| | 8* | n.a. | n.a. | n.a. |
| | 10* | ++; >90% | +++ | +++; >90% |
| 100 mg BIWA 4 | 6* | +++; >80% | +++ | n.a. |
| | 7 | +++; >90% | +++ | n.a. |
| | 9 | +++; >90% | +++ | n.a. |

No = number;
*= included in per protocol analysis,
n.a. = not applicable

TABLE 7.2:6

Soluble CD44v6 in serum. Mean values are given in ng/mL

| | Part A $^{99m}$Tc-BIWA 4 | | | Part B $^{186}$Re-BIWA 4 [mCi/m²] | | | | |
|---|---|---|---|---|---|---|---|---|
| | 25 mg BIWA 4 | 50 mg BIWA 4 | 100 mg BIWA 4 | 20 | 30 | 40 | 50 | 60 |
| N | 3 | 4 | 3 | 2 | 4 | 3 | 6 | 5 |
| pre-dose | 203 | 337 | 174 | 408 | 262 | 346 | 171 | 160 |
| 21 hours | 223 | 301 | 179 | 396 | 177 | 403 | 199 | 170 |
| 48 hours | 200 | 275 | 157 | 384 | 198 | 423 | 199 | 174 |
| 72 hours | 140 | 386 | n.a. | n.a. | n.a. | n.a. | n.a. | n.a. |
| 144 hours | 188 | 282 | 182 | 444 | 284 | 516 | 233 | 195 |
| 240/336 hours | n.a. | n.a. | n.a. | 445 | 337 | n.a. | n.a. | n.a. |
| week 6 | 203 | 310 | 210 | 289 | 220 | 487 | 226 | 162 | n.a. = not applicable, data include the second dosing

Summary—Conclusions:
Efficacy Results:
Part A:

Results from Part A confirmed a dose of 50 mg BIWA 4 as the optimal dose for treatment based on blood concentrations and tissue uptake levels. The distribution as assessed by radioscintigraphy and biopsy measurements was in almost all cases highest in the tumour as compared to other tissues. Uptake of radioactivity increased in the tumour over time. CD44v6 expression was present in more than 80% and 90% of the cells of primary tumour and lymph node metastases, respectively, and in all mucosa specimens obtained.

No correlation was observed between tumour size and uptake of radioactivity in the 50 mg BIWA 4 dose group. The amount of soluble CD44v6 appeared to be constant before and after $^{99m}$T-BIWA 4 administration.

Concentrations of BIWA 4 measured were dose-proportional in the range of 25 mg to 100 mg BIWA 4. A moderate amount of the dose administered was excreted via the kidneys. The percent injected dose (% ID) excreted in urine was similar for all dosing groups.

Part B:

Data from Part B indicate that patients may clinically benefit from $^{186}$Re-BIWA 4 therapy at maximum tolerated dose (MTD). One out of five patients treated with 60 mCi/m² had stable disease. Three out of six patients experienced stable disease at the maximum tolerated dose of 50 mCi/m². Time until progression ranged between 127 and 173 days in those patients who received a second dose of 50 mCi/m². Radioimmunoscintigraphy indicates uptake of radioactivity in tumour tissue. Biodistribution was comparable in other tissues irrespective of dose. Dosimetric analysis did not reveal unexpected high absorbed doses in tissues other than the tumour except for the testes. The amount of soluble CD44v6 detected tended to increase for the $^{186}$Re-BIWA 4 treated patients.

The plasma concentrations of BIWA 4 peaked at 0.92 hours and the antibody was eliminated with a geometric mean half-life of 94 hours for BIWA 4 determined by enzyme-linked immuno-sorbent assay (ELISA) measurement. $C_{max}$ and AUC values (ELISA) were similar to those obtained in Part A of the trial for the 50 mg BIWA 4 dose group.

Safety Results:
Part A:

Tolerability of single dose BIWA 4 coupled to low radiation dose of Technetium-99 was acceptable. Two of the three serious adverse events were due to complications as a result of surgery.

Part B:

The maximum tolerated dose (MTD) was 50 mCi/m$^2$ $_{186}$Re-BIWA 4.

Dose-limiting adverse events were dose dependent reversible reductions in thrombocyte and leucocyte count with subsequent fever in individual patients. Clinical symptoms of thrombocytopenia were mild petechiae.

Mucositis was observed in patients treated with higher radiation doses but was not dose-limiting.

No relevant changes in thyroid stimulating hormone (TSH) values were observed during the course of the trial.

Twelve patients experienced a serious adverse event. Of those, six patients died during the course of Part B of the trial mainly due to progression of the underlying disease.

Allergic reactions were observed rarely with one serious drug-related Quincke's oedema. No allergic reactions occurred during or shortly after infusion of the drug.

Two patients developed HAHAs. Repeated dosing did not induce HAHA development.

Conclusions:

Results indicate uptake of $^{186}$Re-BIWA 4 in tumour tissue and clinical benefit in patients with advanced squamous cell carcinoma of the head and neck. The safety profile appears to be acceptable. BIWA 4 showed dose-proportional pharmacokinetics and tumour uptake did not change relevantly between doses of 50 mg and 100 mg BIWA4.

Example 4

Introduction. Patients with an advanced stage of head and neck squamous cell carcinoma (HNSCC) have an increased risk for development of locoregional recurrent tumors and/or distant metastases. For these patients, development of an effective adjuvant systemic treatment is needed. Knowing that HNSCC are intrinsically radiosensitive, targeting of radionuclides selectively to HNSCC by use of monoclonal antibodies as a form of radioimmunotherapy, might contribute to a more effective therapy.

Objective. To determine the safety, maximum tolerated dose (MTD), immunogenicity and efficacy of radioimmunotherapy with Rhenium-186 ($^{186}$Re)-labelled humanised monoclonal antibody BIWA4 in patients with HNSCC.

Patients and methods. A phase I dose escalation study was conducted in HNSCC patients for whom no curative therapeutic options were available. In a total of 20 patients $^{186}$Re-labelled BIWA4 was administered intravenously in doses of 20, 30, 40, 50 or 60 mCi/m$^2$. Three patients received, at least 3 months after a dose of 50 or 60 mCi/m$^2$, a second dose of 50 mCi/m$^2$.

Results. All single as well as repeated administrations were well tolerated and no signs of acute adverse events were observed. The only significant manifestations of toxicity at the higher doses were oral mucositis and dose-limiting myelotoxicity consisting of thrombo- and leucocytopenia. The MTD was established at 50 mCi/m$^2$. One patient developed a human-anti-human response after one single administration. Stable disease, lasting 4 to 19 weeks, was observed in 5 patients treated at the highest dose levels.

Conclusion. Radioimmunotherapy with $^{186}$Re-labelled BIWA4 in HNSCC patients seems to be safe and tumoricidal doses can be reached. Moreover, due to the low rate of immunogenicity, repeated administrations appear possible. The results of this phase I study encourage the further development of radioimmunotherapy with Rhenium-186 ($^{186}$Re)-labelled humanised monoclonal antibody BIWA4 towards an adjuvant therapy for head and neck cancer patients.

What is claimed is:

1. An isolated or purified humanized CD44v6-specific antibody molecule comprising a heavy chain variable region comprising the amino acid sequence of SEQ ID NO:1 or a glycosylation variant, fusion molecule or a chemical derivative thereof.

2. The antibody molecule of claim 1, wherein said heavy chain variable region consists of the amino acid sequence of SEQ ID NO:1.

3. An isolated or purified humanized CD44v6-specific antibody molecule comprising a light chain variable region comprising the amino acid sequence of SEQ ID NO:2 or a glycosylation variant, fusion molecule or a chemical derivative thereof.

4. The antibody molecule of claim 3, wherein said light chain variable region consists of the amino acid sequence of SEQ ID NO:2.

5. An isolated or purified humanized CD44v6-specific antibody molecule comprising a light chain variable region comprising the amino acid sequence of SEQ ID NO:3 or a glycosylation variant, fusion molecule or a chemical derivative thereof.

6. The antibody molecule of claim 5, wherein said light chain variable region consists of the amino acid sequence of SEQ ID NO:3.

7. The antibody molecule of claim 1, further comprising a light chain variable region comprising the amino acid sequence of SEQ ID NO:2 or a glycosylation variant, fusion molecule or a chemical derivative thereof.

8. The antibody molecule of claim 2, further comprising a light chain variable region consisting of the amino acid sequence of SEQ ID NO:2.

9. The antibody molecule of claim 1, further comprising a light chain variable region comprising the amino acid sequence of SEQ ID NO:3 or a glycosylation variant, fusion molecule or a chemical derivative thereof.

10. The antibody molecule of claim 2, further comprising a light chain variable region consisting of the amino acid sequence of SEQ ID NO:3.

11. An isolated or purified humanized CD44v6-specific antibody molecule comprising a heavy chain variable region encoded by the nucleic acid sequence of SEQ ID NO:4 or a variant based on the degenerative nucleic acid code, fusion molecule or a chemical derivative thereof.

12. The antibody molecule of claim 11, wherein said heavy chain variable region is encoded by the nucleic acid sequence of SEQ ID NO:4.

13. An isolated or purified humanized CD44v6-specific antibody molecule comprising a light chain variable region encoded by the nucleic acid sequence of SEQ ID NO:5 or a variant based on the degenerative nucleic acid code, fusion molecule or a chemical derivative thereof.

14. The antibody molecule of claim 13, wherein said light chain variable region is encoded by the nucleic acid sequence as defined in SEQ ID NO:5.

15. An isolated or purified humanized CD44v6-specific antibody molecule comprising a light chain variable region encoded by the nucleic acid sequence of SEQ ID NO:6 or a variant based on the degenerative nucleic acid code, fusion molecule or a chemical derivative thereof.

16. The antibody molecule of claim 15, wherein said light chain variable region is encoded by the nucleic acid sequence of SEQ ID NO:6.

17. The antibody molecule of claim 11, further comprising a light chain variable region encoded by the nucleic acid sequence of SEQ ID NO:5 or a variant based on the degenerative nucleic acid code, fusion molecule or a chemical derivative thereof.

18. The antibody molecule of claim 12, further comprising a light chain variable region encoded by the nucleic acid sequence of SEQ ID NO:5.

19. The antibody molecule of claim 11, further comprising a light chain variable region encoded by the nucleic acid sequence of SEQ ID NO:6 or a variant based on the degenerative nucleic acid code, fusion molecule or a chemical derivative thereof.

20. The antibody molecule of claim 12, further comprising a light chain variable region encoded by the nucleic acid sequence of SEQ ID NO:6.

21. The antibody molecule of claim 7, wherein said light chain variable region and said heavy chain variable region are separately joined to a human constant region.

22. The antibody molecule of claim 21, wherein said human constant region to which said light chain variable region is joined is a human kappa constant region.

23. The antibody molecule of claim 21, wherein said human constant region to which said heavy chain variable region is joined is a human IgG1 constant region.

24. An isolated or purified humanized CD44v6-specific antibody molecule comprising a heavy chain comprising the amino acid sequence of SEQ ID NO:7 or a glycosylation variant, fusion molecule or a chemical derivative thereof.

25. The antibody molecule of claim 24, wherein said heavy chain consists of the amino acids of SEQ ID NO:7.

26. The antibody molecule of claim 24, further comprising a light chain comprising the amino acid sequence of SEQ ID NO:8 or a glycosylation variant, fusion molecule or a chemical derivative thereof.

27. The antibody molecule of claim 25, further comprising a light chain consisting of the amino acids of SEQ ID NO:8.

28. The antibody molecule of claim 24, further comprising a light chain comprising the amino acid sequence of SEQ ID NO:9 or a glycosylation variant, fusion molecule or a chemical derivative thereof.

29. The antibody molecule of claim 25, further comprising a light chain consisting of the amino acids of SEQ ID NO:9.

30. An isolated or purified humanized CD44v6-specific antibody molecule comprising a heavy chain encoded by the nucleic acid sequence of SEQ ID NO:10 or a variant based on the degenerative nucleic acid code, fusion molecule or a chemical derivative thereof.

31. The antibody molecule of claim 30, wherein said heavy chain is encoded by the nucleic acid sequence of SEQ ID NO:10.

32. The antibody molecule of claim 30, further comprising a light chain encoded by the nucleic acid sequence as defined in SEQ ID NO:11 or a variant based on the degenerative nucleic acid code, fusion molecule or a chemical derivative thereof.

33. The antibody of claim 31, further comprising a light chain encoded by the nucleic acid sequence of SEQ ID NO:11.

34. The antibody molecule of claim 30, further comprising a light chain encoded by the nucleic acid sequence of SEQ ID NO:12 or a variant based on the degenerative nucleic acid code, fusion molecule or a chemical derivative thereof.

35. The antibody of claim 31, further comprising a light chain encoded by the nucleic acid sequence of SEQ ID NO:12.

36. An isolated or purified humanized CD44v6-specific antibody molecule comprising a heavy chain encoded by the nucleic acid sequence of SEQ ID NO:13 or a variant based on the degenerative nucleic acid code, fusion molecule or a chemical derivative thereof.

37. The antibody molecule of claim 36, wherein said heavy chain is encoded by the nucleic acid sequence of SEQ ID NO:13.

38. The antibody molecule of claim 36, further comprising a light chain encoded by the nucleic acid sequence as defined in SEQ ID NO:14 or a variant based on the degenerative nucleic acid code, fusion molecule or a chemical derivative thereof.

39. The antibody molecule of claim 37, further comprising a light chain encoded by the nucleic acid sequence of SEQ ID NO:14.

40. The antibody molecule of claim 36, further comprising a light chain encoded by the nucleic acid sequence of SEQ ID NO:15 or a variant based on the degenerative nucleic acid code, fusion molecule or a chemical derivative thereof.

41. The antibody molecule of claim 37, further comprising a light chain encoded by the nucleic acid sequence of SEQ ID NO:15.

42. An isolated or purified humanized CD44v6-specific antibody molecule comprising a heavy and light chain encoded by the nucleic acid sequence of SEQ ID NO:16 or a variant based on the degenerative nucleic acid code, fusion molecule or a chemical derivative thereof.

43. The antibody molecule of claim 42, wherein said heavy and light chain are encoded by the nucleic acid sequence of SEQ ID NO:16.

44. The antibody molecule of claim 1, wherein said antibody molecule is conjugated to a therapeutic agent.

45. The antibody molecule of claim 44, wherein said therapeutic agent is a therapeutic agent selected from the group consisting of radioisotopes, toxins, toxoids, inflammatory agents and chemotherapeutic agents.

46. The antibody molecule of claim 44, wherein said therapeutic agent is conjugated to said antibody molecule via a linker selected from the group of MAG-3 GABA, MAG-2 GABA and N2S2.

47. The antibody molecule of claim 46, wherein said therapeutic agent is conjugated to said antibody molecule via MAG-2 GABA.

48. The antibody molecule of claim 45, wherein said radioisotope is a β-emiting radioisotope.

49. The antibody molecule of claim 45, wherein said radioisotope is selected from the group consisting of $^{186}$Rhenium, $^{188}$Rhenium, $^{131}$Iodine and $^{90}$Yttrium.

50. The antibody molecule of claim 49, wherein said radioisotope is $^{186}$Rhenium.

51. The antibody molecule of claim 48, wherein said antibody molecule has specific activity of from about 0.5 to about 15 mCi/mg.

52. The antibody molecule of claim 48, wherein said antibody molecule has specific activity of from about 2 to about 6 mCi/mg.

53. The antibody molecule of claim 48, wherein said antibody molecule has specific activity of from about 1 to about 3 mCi/mg.

54. The antibody molecule of claim 1, further comprising a label.

55. The antibody molecule of claim 54, wherein said label is a detectable marker.

56. The antibody molecule of claim 55, wherein said detectable marker is a detectable marker selected from the group consisting of enzymes, dyes, radioisotopes, digoxygenin, and biotin.

57. An antibody molecule according to claim 1, wherein said antibody molecule is conjugated to an imageable agent.

58. The antibody molecule of claim 57, wherein said imageable agent is a radioisotope.

59. The antibody molecule of claim 58, wherein said radioisotope is a γ-emitting radioisotope.

60. The antibody molecule of claim 58, wherein said radioisotope is $^{125}$I.

61. A pharmaceutical composition comprising the antibody molecule of claim 1 and a pharmaceutically acceptable carrier or excipient.

62. The pharmaceutical composition of claim 61, wherein said antibody molecule is conjugated to a radioisotope and wherein said antibody molecule has specific activity of from about 0.5 to about 15 mCi/mg.

63. The pharmaceutical composition of claim 62, wherein the amount of radiolabelled antibody in the pharmaceutical composition to be applied to a patient is from about 10 to about 60 mCi/m$^2$.

64. The pharmaceutical composition of claim 63, wherein the amount of radiolabelled antibody in the pharmaceutical composition to be applied to a patient is about 50 mCi/m$^2$.

65. The pharmaceutical composition of claim 61, further comprising one or more radioprotectants selected from the group consisting of ascorbic acid, gentisic acid, reductic acid, erythorbic acid, p-aminobenzoic acid, 4-hydroxybenzoic acid, nicotinic acid, nicotinamide, 2,5-dihydroxy-1,4-benzenedisulfonic acid, povidone, inositol, and citrate.

66. The pharmaceutical composition of claim 65, wherein said radioprotectant is ascorbic acid.

67. The pharmaceutical composition of claim 61, wherein said antibody molecule comprises (a) a heavy chain variable region comprising the amino acid sequence of SEQ ID NO:1, and (b) a light chain variable region comprising the amino acid sequence of SEQ ID NO:2; wherein said antibody molecule is linked to $^{186}$Rhenium via MAG-2 GABA, and wherein said pharmaceutical composition further comprises ascorbic acid.

68. The CD44v6-specific antibody BIWA4.

* * * * *

SEQUENCE LISTING

```
<160> NUMBER OF SEQ ID NOS: 18

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence:humanized
      antibody sequence

<400> SEQUENCE: 1

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Leu Asp Ser Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Leu Asp Tyr Trp Gly Arg Gly Thr Leu Val Thr Val
            100                 105                 110
```

Ser Ser

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence:humanized
      antibody sequence

<400> SEQUENCE: 2

```
Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Ile Asn Tyr Ile
             20                  25                  30

Tyr Trp Tyr Gln Gln Lys Pro Gly Gln Ala Pro Arg Leu Leu Ile Tyr
         35                  40                  45

Leu Thr Ser Asn Leu Ala Ser Gly Val Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Leu Gln Trp Ser Ser Asn Pro Leu Thr
                 85                  90                  95

Phe Gly Gly Gly Thr Lys Val Glu Ile Lys
            100                 105
```

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence:humanized
      antibody sequence

<400> SEQUENCE: 3

```
Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Ile Asn Tyr Ile
             20                  25                  30

Tyr Trp Leu Gln Gln Lys Pro Gly Gln Ala Pro Arg Ile Leu Ile Tyr
         35                  40                  45

Leu Thr Ser Asn Leu Ala Ser Gly Val Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Leu Gln Trp Ser Ser Asn Pro Leu Thr
                 85                  90                  95

Phe Gly Gly Gly Thr Lys Val Glu Ile Lys
            100                 105
```

<210> SEQ ID NO 4
<211> LENGTH: 342
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 4
gaagtgcagc tggtggagtc tgggggaggc ttagtgaagc ctggagggtc cctaagactc     60

```
tcctgtgcag cctctggatt cactttcagt agctatgaca tgtcttgggt tcgccaggct    120
ccggggaagg ggctggagtg ggtctcaacc attagtagtg gtggtagtta cacctactat    180
ctagacagta taaagggccg attcaccatc tccagagaca atgccaagaa ctccctgtac    240
ctgcaaatga acagtctgag ggctgaggac acggccgtgt attactgtgc aagacagggg    300
ttggactact ggggtcgagg aaccttagtc accgtctcct ca                       342
```

```
<210> SEQ ID NO 5
<211> LENGTH: 318
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 5
gaaattgttc tcacccagtc tccagcaacc ctgtctctgt ctccagggga gagggccacc    60
ctgtcctgca gtgccagctc aagtataaat tacatatact ggtaccagca gaagccagga    120
caggctccta gactcttgat ttatctcaca tccaacctgg cttctggagt ccctgcgcgc    180
ttcagtggca gtgggtctgg aaccgacttc actctcacaa tcagcagcct ggagcctgaa    240
gattttgccg tttattactg cctgcagtgg agtagtaacc cgctcacatt cggtggtggg    300
accaaggtgg agattaaa                                                   318
```

```
<210> SEQ ID NO 6
<211> LENGTH: 318
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 6
gaaattgttc tcacccagtc tccagcaacc ctgtctctgt ctccagggga gagggccacc    60
ctgtcctgca gtgccagctc aagtataaat tacatatact ggctccagca gaagccagga    120
caggctccta gaatcttgat ttatctcaca tccaacctgg cttctggagt ccctgcgcgc    180
ttcagtggca gtgggtctgg aaccgacttc actctcacaa tcagcagcct ggagcctgaa    240
gattttgccg tttattactg cctgcagtgg agtagtaacc cgctcacatt cggtggtggg    300
accaaggtgg agattaaa                                                   318
```

```
<210> SEQ ID NO 7
<211> LENGTH: 444
<212> TYPE: PRT
<213> ORGANISM: Artificial Sequence
<220> FEATURE:
<223> OTHER INFORMATION: Description of Artificial Sequence:humanized
      antibody sequence

<400> SEQUENCE: 7

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Gly Leu Glu Trp Val
         35                  40                  45

Ser Thr Ile Ser Ser Gly Gly Ser Tyr Thr Tyr Tyr Leu Asp Ser Ile
     50                  55                  60
```

-continued

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Gly Leu Asp Tyr Trp Gly Arg Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 8
<211> LENGTH: 213
<212> TYPE: PRT
<213> ORGANISM: Artificial Sequence
<220> FEATURE:
<223> OTHER INFORMATION: Description of Artificial Sequence:humanized
```

-continued antibody sequence

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Asn Tyr Ile
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Leu Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 9
<211> LENGTH: 213
<212> TYPE: PRT
<213> ORGANISM: Artificial Sequence
<220> FEATURE:
<223> OTHER INFORMATION: Description of Artificial Sequence:humanized
      antibody sequence

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Asn Tyr Ile
            20                  25                  30

Tyr Trp Leu Gln Gln Lys Pro Gly Gln Ala Pro Arg Ile Leu Ile Tyr
        35                  40                  45

Leu Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Leu Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr

```
              115                 120                 125
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 10
<211> LENGTH: 2135
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 10
aagctttgac agacgcacaa ccctggactc ccaagtcttt ctcttcagtg acaaacacag      60
acataggata tcacatttgc ttctgacaca actgtgttca ctagcagcct caaacagaca     120
ccatgaactt tgggctcagc ttgattttcc ttgtcctaat tttaaaaggt gtccagtgtg     180
aagtgcagct ggtggagtct gggggaggct tagtgaagcc tggagggtcc ctaagactct     240
cctgtgcagc ctctggattc actttcagta gctatgacat gtcttgggtt cgccaggctc     300
cggggaaggg gctggagtgg gtctcaacca ttagtagtgg tggtagttac acctactatc     360
tagacagtat aaagggccga ttcaccatct ccagagacaa tgccaagaac tccctgtacc     420
tgcaaatgaa cagtctgagg ctgaggaca cggccgtgta ttactgtgca agacaggggt     480
tggactactg gggtcgagga accttagtca ccgtctcctc agctagcacc aagggcccat     540
cggtcttccc cctggcaccc tcctccaaga gcacctctgg gggcacagcg gccctgggct     600
gcctggtcaa ggactacttc cccgaaccgg tgacggtgtc gtggaactca ggcgccctga     660
ccagcggcgt gcacaccttc ccggctgtcc tacagtcctc aggactctac tccctcagca     720
gcgtggtgac cgtgccctcc agcagcttgg gcacccagac ctacatctgc aacgtgaatc     780
acaagcccag caacaccaag gtggacaaga agttggtga gaggccagca cagggaggga     840
gggtgtctgc tggaagcagg ctcagcgctc tgcctggac gcatcccggc tatgcagccc     900
cagtccaggg cagcaaggca ggccccgtct gcctcttcac ccggagcctc tgcccgcccc     960
actcatgctc agggagaggg tcttctggct ttttcccagg ctctgggcag gcacaggcta    1020
ggtgccccta acccaggccc tgcacacaaa ggggcaggtg ctgggctcag acctgccaag    1080
agccatatcc ggaggaccc tgcccctgac ctaagcccac ccaaaggcc aaactctcca    1140 ctccctcagc tcggacacct tctctcctcc cagattccag taactcccaa tcttctctct    1200
gcagagccca aatcttgtga caaaactcac acatgcccac cgtgcccagg taagccagcc    1260
caggcctcgc cctccagctc aaggcgggac aggtgcccta gagtagcctg catccaggga    1320
caggccccag ccgggtgctg acacgtccac ctccatctct tcctcagcac ctgaactcct    1380 gggggaccg tcagtcttcc tcttccccc aaaacccaag gacaccctca tgatctcccg    1440
```

| | |
|---|---:|
| gacccctgag gtcacatgcg tggtggtgga cgtgagccac gaagaccctg aggtcaagtt | 1500 |
| caactggtac gtggacggcg tggaggtgca taatgccaag acaaagccgc gggaggagca | 1560 |
| gtacaacagc acgtaccggg tggtcagcgt cctcaccgtc ctgcaccagg actggctgaa | 1620 |
| tggcaaggag tacaagtgca aggtctccaa caaagccctc ccagccccca tcgagaaaac | 1680 |
| catctccaaa gccaaaggtg ggacccgtgg ggtgcgaggg ccacatggac agaggccggc | 1740 |
| tcggcccacc ctctgccctg agagtgaccg ctgtaccaac ctctgtccta cagggcagcc | 1800 |
| ccgagaacca caggtgtaca ccctgccccc atcccgggat gagctgacca agaaccaggt | 1860 |
| cagcctgacc tgcctggtca aaggcttcta tcccagcgac atcgccgtgg agtgggagag | 1920 |
| caatgggcag ccggagaaca actacaagac cacgcctccc gtgctggact ccgacggctc | 1980 |
| cttcttcctc tacagcaagc tcaccgtgga caagagcagg tggcagcagg ggaacgtctt | 2040 |
| ctcatgctcc gtgatgcatg aggctctgca caaccactac acgcagaaga gcctctccct | 2100 |
| gtctccgggt aaatgagtgc gacggccgcg aattc | 2135 |

<210> SEQ ID NO 11
<211> LENGTH: 785
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 11

| | |
|---|---:|
| aagcttgatc ttcaggatat cacatttgct tctgacacaa ctgtgttcac tagcaacctc | 60 |
| aaacagacac catggatttt caggtgcaga ttttcagctt cctgctaatg agtgcctcag | 120 |
| tcataatgtc caggggagaa attgttctca cccagtctcc agcaaccctg tctctgtctc | 180 |
| caggggagag ggccacccctg tcctgcagtg ccagctcaag tataaattac atatactggt | 240 |
| accagcagaa gccaggacag gctcctagac tcttgattta tctcacatcc aacctggctt | 300 |
| ctggagtccc tgcgcgcttc agtggcagtg gtctggaac cgacttcact ctcacaatca | 360 |
| gcagcctgga gcctgaagat tttgccgttt attactgcct gcagtggagt agtaacccgc | 420 |
| tcacattcgg tggtgggacc aaggtggaga ttaaacggac tgtggctgca ccatctgtct | 480 |
| tcatcttccc gccatctgat gagcagttga aatctggaac tgctagcgtt gtgtgcctgc | 540 |
| tgaataactt ctatcccaga gaggccaaag tacagtggaa ggtggataac gccctccaat | 600 |
| cgggtaactc ccaggagagt gtcacagagc aggacagcaa ggacagcacc tacagcctca | 660 |
| gcagcaccct gacgctgagc aaagcagact acgagaaaca caaagtctac gcctgcgaag | 720 |
| tcacccatca gggcctgagc tcgcccgtca caaagagctt caacagggga gagtgttagg | 780 |
| aattc | 785 |

<210> SEQ ID NO 12
<211> LENGTH: 785
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 12

| | |
|---|---:|
| aagcttgatc ttcaggatat cacatttgct tctgacacaa ctgtgttcac tagcaacctc | 60 |
| aaacagacac catggatttt caggtgcaga ttttcagctt cctgctaatg agtgcctcag | 120 |
| tcataatgtc caggggagaa attgttctca cccagtctcc agcaaccctg tctctgtctc | 180 |

-continued

| | |
|---|---|
| cagggagag ggccaccctg tcctgcagtg ccagctcaag tataaattac atatactggc | 240 |
| tccagcagaa gccaggacag gctcctagaa tcttgattta tctcacatcc aacctggctt | 300 |
| ctggagtccc tgcgcgcttc agtggcagtg ggtctggaac cgacttcact ctcacaatca | 360 |
| gcagcctgga gcctgaagat tttgccgttt attactgcct gcagtggagt agtaacccgc | 420 |
| tcacattcgg tggtgggacc aaggtggaga ttaaacggac tgtggctgca ccatctgtct | 480 |
| tcatcttccc gccatctgat gagcagttga aatctggaac tgctagcgtt gtgtgcctgc | 540 |
| tgaataactt ctatcccaga gaggccaaag tacagtggaa ggtggataac gccctccaat | 600 |
| cgggtaactc ccaggagagt gtcacagagc aggacagcaa ggacagcacc tacagcctca | 660 |
| gcagcaccct gacgctgagc aaagcagact acgagaaaca caaagtctac gcctgcgaag | 720 |
| tcacccatca gggcctgagc tcgcccgtca caaagagctt caacagggga gagtgttagg | 780 |
| aattc | 785 |

<210> SEQ ID NO 13
<211> LENGTH: 1392
<212> TYPE: DNA
<213> ORGANISM: Artificial Sequence
<220> FEATURE:
<223> OTHER INFORMATION: Description of Artificial Sequence:humanized antibody sequence
<400> SEQUENCE: 13

| | |
|---|---|
| atggagtttg ggctgagctg gcttttttctt gtggctattt taaaaggtgt ccagtgtgaa | 60 |
| gtgcagctgg tggagtctgg gggaggctta gtgaagcctg gagggtccct aagactctcc | 120 |
| tgtgcagcct ctggattcac tttcagtagc tatgacatgt cttgggttcg ccaggctccg | 180 |
| gggaaggggc tggagtgggt ctcaaccatt agtagtggtg gtagttacac ctactatcta | 240 |
| gacagtataa agggccgatt caccatctcc agagacaatg ccaagaactc cctgtacctg | 300 |
| caaatgaaca gtctgagggc tgaggacacg gccgtgtatt actgtgcaag acaggggttg | 360 |
| gactactggg gtcgaggaac cttagtcacc gtctcctcag ctagcaccaa gggcccatcg | 420 |
| gtcttccccc tggcaccctc ctccaagagc acctctgggg gcacagcggc cctgggctgc | 480 |
| ctggtcaagg actacttccc cgaaccggtg acggtgtcgt ggaactcagg cgccctgacc | 540 |
| agcggcgtgc acaccttccc ggctgtccta cagtcctcag gactctactc cctcagcagc | 600 |
| gtggtgaccg tgccctccag cagcttgggc acccagacct acatctgcaa cgtgaatcac | 660 |
| aagcccagca acaccaaggt ggacaagaaa gttgagccca atcttgtga caaaactcac | 720 |
| acatgcccac cgtgcccagc acctgaactc ctggggggac cgtcagtctt cctcttcccc | 780 |
| ccaaaaccca aggacaccct catgatctcc cggacccctg aggtcacatg cgtggtggtg | 840 |
| gacgtgagcc acgaagaccc tgaggtcaag ttcaactggt acgtggacgg cgtggaggtg | 900 |
| cataatgcca agacaaagcc gcgggaggag cagtacaaca gcacgtaccg tgtggtcagc | 960 |
| gtcctcaccg tcctgcacca ggactggctg aatggcaagg agtacaagtg caaggtctcc | 1020 |
| aacaaagccc tcccagcccc catcgagaaa accatctcca agccaaaggg cagccccga | 1080 |
| gaaccacagg tgtacaccct gcccccatcc cgggatgagc tgaccaagaa ccaggtcagc | 1140 |
| ctgacctgcc tggtcaaagg cttctatccc agcgacatcg ccgtggagtg ggagagcaat | 1200 |
| gggcagccgg agaacaacta caagaccacg cctcccgtgc tggactccga cggctccttc | 1260 |
| ttcctctaca gcaagctcac cgtggacaag agcaggtggc agcaggggaa cgtcttctca | 1320 |
| tgctccgtga tgcatgaggc tctgcacaac cactacacgc agaagagcct ctccctgtct | 1380 |

-continued

```
ccgggtaaat ga                                                        1392

<210> SEQ ID NO 14
<211> LENGTH: 702
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 14
atggaagccc cagctcagct tctcttcctc ctgctgctct ggctcccaga taccaccgga    60
gaaattgttc tcacccagtc tccagcaacc ctgtctctgt ctccagggga gagggccacc   120
ctgtcctgca gtgccagctc aagtataaat tacatatact ggtaccagca gaagccagga   180
caggctccta gactcttgat ttatctcaca tccaacctgg cttctggagt ccctgcgcgc   240
ttcagtggca gtgggtctgg aaccgacttc actctcacaa tcagcagcct ggagcctgaa   300
gattttgccg tttattactg cctgcagtgg agtagtaacc cgctcacatt cggtggtggg   360
accaaggtgg agattaaacg tacggtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ga                     702

<210> SEQ ID NO 15
<211> LENGTH: 702
<212> TYPE: DNA
<213> ORGANISM: Artificial Sequence
<220> FEATURE:
<223> OTHER INFORMATION: Description of Artificial Sequence:humanized
      antibody sequence

<400> SEQUENCE: 15
atggaagccc cagctcagct tctcttcctc ctgctgctct ggctcccaga taccaccgga    60
gaaattgttc tcacccagtc tccagcaacc ctgtctctgt ctccagggga gagggccacc   120
ctgtcctgca gtgccagctc aagtataaat tacatatact ggtccagca gaagccagga    180 caggctccta gaatcttgat ttatctcaca tccaacctgg cttctggagt ccctgcgcgc   240
ttcagtggca gtgggtctgg aaccgacttc actctcacaa tcagcagcct ggagcctgaa   300
gattttgccg tttattactg cctgcagtgg agtagtaacc cgctcacatt cggtggtggg   360
accaaggtgg agattaaacg tacggtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ga                     702

<210> SEQ ID NO 16
<211> LENGTH: 9568
<212> TYPE: DNA
<213> ORGANISM: Artificial Sequence
<220> FEATURE:
```

<223> OTHER INFORMATION: Description of Artificial Sequence:humanized antibody sequence

<400> SEQUENCE: 16

| | | | | | |
|---|---|---|---|---|---|
| ctgacgcgcc | ctgtagcggc | gcattaagcg | cggcgggtgt | ggtggttacg | cgcagcgtga | 60 |
| ccgctacact | tgccagcgcc | ctagcgcccg | ctcctttcgc | tttcttccct | tcctttctcg | 120 |
| ccacgttcgc | cggctttccc | cgtcaagctc | taaatcgggg | gctcccttta | gggttccgat | 180 |
| ttagtgcttt | acggcacctc | gaccccaaaa | aacttgatta | gggtgatggt | tcacgtaggg | 240 |
| tcgcgacgta | ccgggccccc | cctcgattaa | ttaatcgagc | tactagcttt | gcttctcaat | 300 |
| ttcttatttg | cataatgaga | aaaaaggaa | aattaatttt | aacaccaatt | cagtagttga | 360 |
| ttgagcaaat | gcgttgccaa | aaggatgct | ttagagacag | tgttctctgc | acagataagg | 420 |
| acaaacatta | ttcagaggga | gtacccagag | ctgagactcc | taagccagtg | agtggcacag | 480 |
| cattctaggg | agaaatatgc | ttgtcatcac | cgaagcctga | ttccgtagag | ccacaccttg | 540 |
| gtaagggcca | atctgctcac | acaggataga | gagggcagga | gccagggcag | agcatataag | 600 |
| gtgaggtagg | atcagttgct | cctcacattt | gcttctgaca | tagttgtgcc | agcatggagg | 660 |
| aatcgatcct | ccatgcttga | acaagatgga | ttgcacgcag | gttctccggc | cgcttgggtg | 720 |
| gagaggctat | tcggctatga | ctgggcacaa | cagacaatcg | gctgctctga | tgccgccgtg | 780 |
| ttccggctgt | cagcgcaggg | gcgcccggtt | cttttttgtca | agaccgacct | gtccggtgcc | 840 |
| ctgaatgaac | tgcaggtaag | tgcggccgct | ctaggcctcc | aaaaaagcct | cctcactact | 900 |
| tctggaatag | ctcagaggcc | gaggcggcct | cggcctctgc | ataaataaaa | aaaattagtc | 960 |
| agccatgcat | ggggcggaga | atgggcggaa | ctgggcggag | ttaggggcgg | gatgggcgga | 1020 |
| gttaggggcg | ggactatggt | tgctgactaa | ttgagatgca | tgctttgcat | acttctgcct | 1080 |
| gctgggagc | ctgggggactt | tccacacctg | gttgctgact | aattgagatg | catgctttgc | 1140 |
| atacttctgc | ctgctgggga | gcctggggac | tttccacacc | ctaactgaca | cacattccac | 1200 |
| agaattaatt | cccctagtta | ttaatagtaa | tcaattacgg | ggtcattagt | tcatagccca | 1260 |
| tatatggagt | tccgcgttac | ataacttacg | gtaaatggcc | cgcctggctg | accgcccaac | 1320 |
| gaccccgcc | cattgacgtc | aataatgacg | tatgttccca | tagtaacgcc | aatagggact | 1380 |
| ttccattgac | gtcaatgggt | ggactattta | cggtaaactg | cccacttggc | agtacatcaa | 1440 |
| gtgtatcata | tgccaagtac | gccccctatt | gacgtcaatg | acggtaaatg | gcccgcctgg | 1500 |
| cattatgccc | agtacatgac | cttatgggac | tttcctactt | ggcagtacat | ctacgtatta | 1560 |
| gtcatcgcta | ttaccatggt | gatgcggttt | tggcagtaca | tcaatgggcg | tggatagcgg | 1620 |
| tttgactcac | ggggatttcc | aagtctccac | cccattgacg | tcaatgggag | tttgttttgg | 1680 |
| caccaaaatc | aacgggactt | tccaaaatgt | cgtaacaact | ccgccccatt | gacgcaaatg | 1740 |
| ggcggtaggc | gtgtacggtg | ggaggtctat | ataagcagag | ctgggtacgt | gaaccgtcag | 1800 |
| atcgcctgga | gacgccatca | cagatctctc | accatggaag | ccccagctca | gcttctcttc | 1860 |
| ctcctgctgc | tctggctccc | agataccacc | ggagaaattg | ttctcaccca | gtctccagca | 1920 |
| accctgtctc | tgtctccagg | ggagagggcc | accctgtcct | gcagtgccag | ctcaagtata | 1980 |
| aattacatat | actggtacca | gcagaagcca | ggacaggctc | ctagactctt | gatttatctc | 2040 |
| acatccaacc | tggcttctgg | agtccctgcg | cgcttcagtg | gcagtgggtc | tggaaccgac | 2100 |
| ttcactctca | caatcagcag | cctgagcct | aagattttg | ccgttttatta | ctgcctgcag | 2160 |
| tggagtagta | acccgctcac | attcggtggt | gggaccaagg | tggagattaa | acgtacggtg | 2220 |

-continued

```
gctgcaccat ctgtcttcat cttcccgcca tctgatgagc agttgaaatc tggaactgcc      2280
tctgttgtgt gcctgctgaa taacttctat cccagagagg ccaaagtaca gtggaaggtg      2340
gataacgccc tccaatcggg taactcccag gagagtgtca cagagcagga cagcaaggac      2400
agcacctaca gcctcagcag cacccctgacg ctgagcaaag cagactacga gaaacacaaa     2460
gtctacgcct gcgaagtcac ccatcagggc ctgagctcgc ccgtcacaaa gagcttcaac      2520
aggggagagt gttgaattca gatccgttaa cggttaccaa ctacctagac tggattcgtg      2580
acaacatgcg gccgtgatat ctacgtatga tcagcctcga ctgtgccttc tagttgccag      2640
ccatctgttg tttgcccctc ccccgtgcct tccttgaccc tggaaggtgc cactcccact      2700
gtcctttcct aataaaatga ggaaattgca tcgcattgtc tgagtaggtg tcattctatt      2760 ctgggggtg gggtggggca ggacagcaag ggggaggatt ggaagacaa tagcaggcat        2820 gctggggatg cggtgggctc tatggaacca gctgggacta gtagctttgc ttctcaattt      2880
cttatttgca taatgagaaa aaaggaaaa ttaattttaa caccaattca gtagttgatt       2940
gagcaaatgc gttgccaaaa aggatgcttt agagacagtg ttctctgcac agataaggac      3000
aaacattatt cagagggagt acccagagct gagactccta agccagtgag tggcacagca     3060
ttctagggag aaatatgctt gtcatcaccg aagcctgatt ccgtagagcc acccttggt      3120 aagggccaat ctgctcacac aggatagaga gggcaggagc cagggcagag catataaggt     3180
gaggtaggat cagttgctcc tcacatttgc ttctgacata gttgtgttgg gagcttggat     3240
agcttggaca gctcagggct gcgatttcgc gccaaacttg acggcaatcc tagcgtgaag    3300
gctggtagga ttttatcccc gctgccatca tggttcgacc attgaactgc atcgtcgccg    3360
tgtcccaaaa tatggggatt ggcaagaacg gagacctacc ctggcctccg ctcaggaacg    3420
agttcaagta cttccaaaga atgaccacaa cctcttcagt ggaaggtaaa cagaatctgg    3480
tgattatggg taggaaaacc tggttctcca ttcctgagaa gaatcgacct ttaaaggaca    3540
gaattaatat agttctcagt agagaactca agaaccacc acgaggagct cattttcttg     3600
ccaaaagttt ggatgatgcc ttaagactta ttgaacaacc ggaattggca agtaaagtag    3660
acatggtttg gatagtcgga ggcagttctg tttaccagga agccatgaat caaccaggcc    3720
accttagact ctttgtgaca aggatcatgc aggaatttga aagtgacacg ttttccccag    3780
aaattgattt ggggaaatat aaacttctcc cagaatacc aggcgtcctc tctgaggtcc     3840
aggaggaaaa aggcatcaag tataagtttg aagtctacga gaagaaagac taacaggaag    3900
atgctttcaa gttctctgct ccctcctaa agctatgcat tttataaga ccatgggact      3960 tttgctggct ttagatcagc ctcgactgtg ccttctagtt gccagccatc tgttgtttgc    4020
ccctcccccg tgccttcctt gaccctggaa ggtgccactc ccactgtcct ttcctaataa    4080
aatgaggaaa ttgcatcgca ttgtctgagt aggtgtcatt ctattctggg gggtggggtg   4140
gggcaggaca gcaaggggga ggattggaa gacaatagca ggcatgctgg ggatgcggtg     4200
ggctctatgg aaccagctgg ggctcgaagc ggccgctccg gatatgccaa gtacgccccc    4260
tattgacgtc aatgacggta atggcccgc ctggcattat gcccagtaca tgaccttatg      4320
ggactttcct acttggcagt acatctacgt attagtcatc gctattacca tggtgatgcg   4380
gttttggcag tacatcaatg ggcgtggata gcggtttgac tcacgggat ttccaagtct     4440 ccacccatt gacgtcaatg ggagtttgtt ttggcaccaa atcaacggg actttccaaa     4500 atgtcgtaac aactccgccc cattgacgca aatgggcggt aggcgtgtac ggtgggaggt    4560
ctatataagc agagctgggt acgtcctcac attcagtgat cagcactgaa cacagacccg    4620
```

```
tcgacatgga gtttgggctg agctggcttt tcttgtggc tattttaaaa ggtgtccagt   4680
gtgaagtgca gctggtggag tctgggggag gcttagtgaa gcctggaggg tccctaagac   4740
tctcctgtgc agcctctgga ttcactttca gtagctatga catgtcttgg gttcgccagg   4800
ctccggggaa ggggctggag tgggtctcaa ccattagtag tggtggtagt tacacctact   4860
atctagacag tataaagggc cgattcacca ctctccagaga caatgccaag aactccctgt   4920
acctgcaaat gaacagtctg agggctgagg acacggccgt gtattactgt gcaagacagg   4980
ggttggacta ctgggtcga ggaaccttag tcaccgtctc ctcagctagc accaagggcc   5040
catcggtctt ccccctggca ccctcctcca agagcacctc tgggggcaca gcggccctgg   5100
gctgcctggt caaggactac ttccccgaac cggtgacggt gtcgtggaac tcaggcgccc   5160
tgaccagcgg cgtgcacacc ttcccggctg tcctacagtc ctcaggactc tactccctca   5220
gcagcgtggt gaccgtgccc tccagcagct gggcaccca gacctacatc tgcaacgtga   5280
atcacaagcc cagcaacacc aaggtggaca agaaagttga gcccaaatct tgtgacaaaa   5340
ctcacacatg cccaccgtgc ccagcacctg aactcctggg gggaccgtca gtcttcctct   5400
tccccccaaa acccaaggac accctcatga tctcccggac ccctgaggtc acatgcgtgg   5460
tggtggacgt gagccacgaa gaccctgagg tcaagttcaa ctggtacgtg gacggcgtgg   5520
aggtgcataa tgccaagaca aagccgcggg aggagcagta caacagcacg taccgtgtgg   5580
tcagcgtcct caccgtcctg caccaggact ggctgaatgg caaggagtac aagtgcaagg   5640
tctccaacaa agccctccca gccccatcg agaaaaccat ctccaaagcc aaagggcagc   5700
cccgagaacc acaggtgtac accctgcccc catcccggga tgagctgacc aagaaccagg   5760
tcagcctgac ctgcctggtc aaaggcttct atcccagcga catcgccgtg gagtgggaga   5820
gcaatgggca gccggagaac aactacaaga ccacgcctcc cgtgctggac tccgacggct   5880
ccttcttcct ctacagcaag ctcaccgtgg acaagagcag gtggcagcag gggaacgtct   5940
tctcatgctc cgtgatgcat gaggctctgc acaaccacta cacgcagaag agcctctccc   6000
tgtctccggg taaatgagga tccgttaacg gttaccaact acctagactg gattcgtgac   6060
aacatgcggc cgtgatatct acgtatgatc agcctcgact gtgccttcta gttgccagcc   6120
atctgttgtt tgcccctccc ccgtgccttc cttgaccctg gaaggtgcca ctcccactgt   6180
cctttcctaa taaaatgagg aaattgcatc gcattgtctg agtaggtgtc attctattct   6240
ggggggtggg gtggggcagg acagcaaggg ggaggattgg gaagacaata gcaggcatgc   6300
tggggatgcg gtgggctcta tggaaccagc tggggctcga cagcgctgcg atcgcctcga   6360
ggccgctact aactctctcc tccctccttt tcctgcagg acgaggcagc gcggctatcg   6420
tggctggcca cgacgggcgt tccttgcgca gctgtgctcg acgttgtcac tgaagcggga   6480
agggactggc tgctattggg cgaagtgccg ggcaggatc tcctgtcatc tcaccttgct   6540
cctgccgaga aagtatccat catggctgat gcaatgcggc ggctgcatac gcttgatccg   6600
gctacctgcc cattcgacca ccaagcgaaa catcgcatcg agcgagcacg tactcggatg   6660
gaagccggtc ttgtcgatca ggatgatctg gacgaagagc atcagggct cgcgccagcc   6720 gaactgttcg ccaggctcaa ggcgcgcatg cccgacggcg aggatctcgt cgtgacccat   6780
ggcgatgcct gcttgccgaa tatcatggtg gaaaatggcc gcttttctgg attcatcgac   6840 tgtggccgc tgggtgtggc ggaccgctat caggacatag cgttggctac ccgtgatatt   6900
gctgaagagc ttggcggcga atgggctgac cgcttcctcg tgctttacgg tatcgccgct   6960
```

-continued

```
cccgattcgc agcgcatcgc cttctatcgc cttcttgacg agttcttctg agcgggactc   7020
tggggttcga atgaccgac caagcgacgc ccaacctgcc atcacgagat ttcgattcca   7080
ccgccgcctt ctatgaaagg ttgggcttcg aatcgtttt ccgggacgcc ggctggatga    7140
tcctccagcg cggggatctc atgctggagt tcttcgccca ccccaacttg tttattgcag   7200
cttataatgg ttacaaataa agcaatagca tcacaaattt cacaaataaa gcattttttt   7260
cactgcattc tagttgtggt ttgtccaaac tcatcaatct atcttatcat gtctggatcg   7320
cggccggccg caccgcggtg gagctttaat taaggcgcgc cagctccagc ttttgttccc   7380
tttagtgagg gttaatttcg agcttggcgt aatcatggtc atagctgttt cctgtgtgaa   7440
attgttatcc gctcacaatt ccacacaaca tacgagccgg aagcataaag tgtaaagcct   7500
ggggtgccta atgagtgagc taactcacat taattgcgtt gcgctcactg cccgctttcc   7560
agtcgggaaa cctgtcgtgc cagctgcatt aatgaatcgg ccaacgcgcg gggagaggcg   7620
gtttgcgtat tgggcgctct tccgcttcct cgctcactga ctcgctgcgc tcggtcgttc   7680
ggctgcggcg agcggtatca gctcactcaa aggcggtaat acggttatcc acagaatcag   7740
gggataacgc aggaaagaac atgtgagcaa aaggccagca aaaggccagg aaccgtaaaa   7800
aggccgcgtt gctggcgttt ttccataggc tccgccccc tgacgagcat cacaaaaatc    7860
gacgctcaag tcagaggtgg cgaaacccga caggactata aagataccag gcgtttcccc   7920
ctggaagctc cctcgtgcgc tctcctgttc cgaccctgcc gcttaccgga tacctgtccg   7980
cctttctccc ttcgggaagc gtggcgcttt ctcatagctc acgctgtagg tatctcagtt   8040
cggtgtaggt cgttcgctcc aagctgggct gtgtgcacga accccccgtt cagcccgacc   8100
gctgcgcctt atccggtaac tatcgtcttg agtccaaccc ggtaagacac gacttatcgc   8160
cactggcagc agccactggt aacaggatta gcagagcgag gtatgtaggc ggtgctacag   8220
agttcttgaa gtggtggcct aactacggct acactagaag gacagtattt ggtatctgcg   8280
ctctgctgaa gccagttacc ttcggaaaaa gagttggtag ctcttgatcc ggcaaacaaa   8340
ccaccgctgg tagcggtggt ttttttgttt gcaagcagca gattacgcgc agaaaaaaag   8400
gatctcaaga agatcctttg atcttttcta cggggtctga cgctcagtgg aacgaaaact   8460
cacgttaagg gattttggtc atgagattat caaaaaggat cttcacctag atccttttaa   8520
attaaaaatg aagttttaaa tcaatctaaa gtatatatga gtaaacttgg tctgacagtt   8580
accaatgctt aatcagtgag gcacctatct cagcgatctg tctatttcgt tcatccatag   8640
ttgcctgact ccccgtcgtg tagataacta cgatacggga gggcttacca tctggcccca   8700
gtgctgcaat gataccgcga gacccacgct caccggctcc agatttatca gcaataaacc   8760
agccagccgg aagggccgag cgcagaagtg gtcctgcaac tttatccgcc tccatccagt   8820
ctattaattg ttgccgggaa gctagagtaa gtagttcgcc agttaatagt ttgcgcaacg   8880
ttgttgccat tgctacaggc atcgtggtgt cacgctcgtc gtttggtatg gcttcattca   8940
gctccggttc ccaacgatca aggcgagtta catgatcccc catgttgtgc aaaaaagcgg   9000
ttagctcctt cggtcctccg atcgttgtca gaagtaagtt ggccgcagtg ttatcactca   9060
tggttatggc agcactgcat aattctctta ctgtcatgcc atccgtaaga tgcttttctg   9120
tgactggtga gtactcaacc aagtcattct gagaatagtg tatgcggcga ccgagttgct   9180
cttgcccggc gtcaatacgg gataataccg cgccacatag cagaacttta aaagtgctca   9240
tcattggaaa acgttcttcg gggcgaaaac tctcaaggat cttaccgctg ttgagatcca   9300
gttcgatgta acccactcgt gcacccaact gatcttcagc atcttttact ttcaccagcg   9360
```

```
tttctgggtg agcaaaaaca ggaaggcaaa atgccgcaaa aaagggaata agggcgacac    9420
ggaaatgttg aatactcata ctcttccttt ttcaatatta ttgaagcatt tatcagggtt    9480
attgtctcat gagcggatac atatttgaat gtatttagaa aaataaacaa atagggttc     9540 cgcgcacatt tccccgaaaa gtgccaca                                       9568
```

<210> SEQ ID NO 17
<211> LENGTH: 6414
<212> TYPE: DNA
<213> ORGANISM: Artificial Sequence
<220> FEATURE:
<223> OTHER INFORMATION: Description of Artificial Sequence:plasmid

<400> SEQUENCE: 17

```
tcgacattga ttattgacta gttattaata gtaatcaatt acggggtcat tagttcatag     60
cccatatatg gagttccgcg ttacataact tacggtaaat ggcccgcctg gctgaccgcc    120
caacgacccc cgcccattga cgtcaataat gacgtatgtt cccatagtaa cgccaatagg    180
gactttccat tgacgtcaat gggtggagta tttacggtaa actgcccact ggcagtaca     240 tcaagtgtat catatgccaa gtacgccccc tattgacgtc aatgacggta aatggcccgc    300
ctggcattat gcccagtaca tgaccttatg gactttcct acttggcagt acatctacgt     360
attagtcatc gctattacca tggtgatgcg gttttggcag tacatcaatg ggcgtggata    420
gcggtttgac tcacggggat ttccaagtct ccacccccatt gacgtcaatg ggagtttgtt    480
ttggcaccaa aatcaacggg actttccaaa atgtcgtaac aactccgccc cattgacgca    540
aatgggcggt aggcgtgtac ggtgggaggt ctatataagc agagctctct ggctaactag    600
agaacccact gcttaactgg cttatcgaaa ttaatacgac tcactatagg gagacccaag    660
cttctgcagg tcgacatcga tggatccggt acctcgagcg cgaattctct agaggatctt    720
tgtgaaggaa ccttacttct gtggtgtgac ataattggac aaaactaccta cagagattta    780 aagctctaag gtaaatataa aattttttaag tgtataatgt gttaaactac tgattctaat    840
tgtttgtgta tttagattc caacctatgg aactgatgaa tgggagcagt ggtggaatgc     900
ctttaatgag gaaaacctgt tttgctcaga agaaatgcca tctagtgatg atgaggctac    960
tgctgactct caacattcta ctcctccaaa aaagaagaga aaggtagaag accccaagga   1020 cttttccttca gaattgctaa gttttttgag tcatgctgtg tttagtaata gaactcttgc   1080
ttgctttgct atttcacacca caaggaaaa agctgcactg ctatacaaga aaattatgga   1140
aaaatatttg atgtatagtg ccttgactag agatcataat cagccatacc acatttgtag   1200
aggttttact tgctttaaaa aacctcccac acctcccct gaacctgaaa cataaaatga   1260
atgcaattgt tgttgttaac ttgtttattg cagcttataa tggttacaaa taaagcaata   1320
gcatcacaaa tttcacaaat aaagcatttt tttcactgca ttctagttgt ggtttgtcca   1380
aactcatcaa tgtatcttat catgtctgga tcaattctga gaaactagcc ttaaagacag   1440
acagctttgt tctagtcagc caggcaagca tatgtaaata aagttcctca gggaactgag   1500
gttaaaagat gtatcctgga cctgccagac ctggccattc acgtaaacag aagattccgc   1560
ctcaagttcc ggttaacaac aggaggcaac gagatctcaa atctattact ctaatcggg   1620 taattaaaac ctttcaacta aaacacggac ccacggatgt cacccacttt tccttccccg   1680
gctccgccct tctcagtact ccccaccatt aggctcgcta ctccacctcc acttccgggc   1740
gcgacaccca cgtgccctct cccacccgac gctaaccccg ccctgcccg tctgaccccg   1800
```

```
cccaccacct ggccccgccc cgttgaggac agaagaaacc ccgggcagcc gcagccaagg    1860
cggacgggta gacgctgggg gcgctgagga gtcgtcctct accttctctg ctggctcggt    1920
gggggacgcg gtggatctca ggcttccgga agactggaag aaccggctca gaaccgcttg    1980
tctccgcggg gcttgggcgg cggaagaatg gccgctagac gcggacttgg tgcgaggcat    2040
cgcaggatgc agaagagcaa gcccgccggg agcgcgcggc tgtactaccc cgcgcctgga    2100
gcggccacgc cggactgggc ggggccggcc tggtggaggc ggagtctgac ctcgtggagg    2160
cggggcctct gatgttcaaa taggatgcta ggcttgttga ggcgtggcct ccgattcaca    2220
agtgggaagc agcgccgggc gactgcaatt tcgcgccaaa cttgggggaa gcacagcgta    2280
caggctgcct aggtgatcgc tgctgctgtc atggttcgac cgctgaactg catcgtcgcc    2340
gtgtcccaga atatgggcat cggcaagaac ggagaccttc cctggccaat gctcaggtac    2400
tggctggatt gggttaggga accgaggcg gttcgctgaa tcgggtcgag cacttggcgg    2460
agacgcgcgg gccaactact tagggacagt catgaggggt aggcccgccg gctgctgccc    2520
ttgcccatgc ccgcggtgat ccccatgctg tgccagcctt tgcccagagg cgctctagct    2580
gggagcaaag tccggtcact gggcagcacc acccccgga cttgcatggg tagccgctga    2640
gatggagcct gagcacacgt gacagggtcc ctgttaacgc agtgtttctc taactttcag    2700
gaacgagttc aagtacttcc aaagaatgac caccacctcc tcagtggaag gtaaacagaa    2760
cctggtgatt atgggccgga aaacctggtt ctccattcct gagaagaatc gacctttaaa    2820
ggacagaatt aatatagttc tcagtagaga gctcaaggaa ccaccacaag gagctcattt    2880
tcttgccaaa gtctggacc atgccttaaa acttattgaa caaccagagt tagcagataa    2940
agtggacatg gtttggatag ttggaggcag ttccgtttac aaggaagcca tgaatcagcc    3000
aggccatctc agactctttg tgacaaggat catgcaggaa tttgaaagtg acacgttctt    3060
cccagaaatt gatttggaga atataaaact tctcccagag tacccagggg tcctttctga    3120
agtccaggag gaaaaaggca tcaagtataa atttgaagtc tatgagaaga aaggctaaca    3180
gaaagatact tgctgattga cttcaagttc tactgctttc ctcctaaaat tatgcatttt    3240
tacaagacca tgggacttgt gttggcttta gatcctgtgc atcctgggca actgttgtac    3300
tctaagccac tccccaaagt catgcccag cccctgtata attctaaaca attagaatta    3360
ttttcatttt cattagtcta accaggttat attaaatata ctttaagaaa caccatttgc    3420
cataaagttc tcaatgcccc tcccatgcag cctcaagtgg ctccccagca gatgcatagg    3480
gtagtgtgtg tacaagagac cccaaagaca tagagcccct gagagcatga gctgatatgg    3540
gggctcatag agataggagc tagatgaata agtacaaagg gcagaaatgg gtttaaccag    3600
gcagagctag aactcagact ttaaagaaaa ttagatcaaa gtagagactg aattattctg    3660
cacatcagac tctgagcaga gttctgttca ctcagacaga aaatgggtaa attgagagct    3720
ggctccattg tgctccttag agatgggagc aggtggagga ttatataagg tctgaacat    3780 ttaacttctc cgtttctcat cttcagtgag attccaaggg atactacaat tctgtggaat    3840
gtgtgtcagt tagggtgtgg aaagtccca ggctccccag caggcagaag tatgcaaagc    3900
atgcatctca attagtcagc aaccaggtgt ggaaagtccc caggctcccc agcaggcaga    3960
agtatgcaaa gcatgcatct caattagtca gcaaccatag tcccgcccct aactccgccc    4020
atcccgcccc taactccgcc cagttccgcc cattctccgc cccatggctg actaattttt    4080
tttatttatg cagaggccga ggcgcctctg agctattcca gaagtagtga ggaggctttt    4140
ttggaggcct aggcttttgc aaaaaagcta attcagcctg aatggcgaat gggacgcgcc    4200
```

-continued

```
ctgtagcggc gcattaagcg cggcgggtgt ggtggttacg cgcagcgtga ccgctacact    4260
tgccagcgcc ctagcgcccg ctcctttcgc tttcttccct tcctttctcg ccacgttcgc    4320
cggctttccc cgtcaagctc taaatcgggg ctcccttta gggttccgat ttagtgcttt     4380
acggcacctc gaccccaaaa acttgattag ggtgatggtt cacgtagtgg gccatcgccc    4440
tgatagacgg ttttcgccc tttgacgttg gagtccacgt tctttaatag tggactcttg     4500
ttccaaactg gaacaacact caaccctatc tcggtctatt cttttgattt ataagggatt    4560
ttgccgattt cggcctattg gttaaaaaat gagctgattt aacaaaaatt taacgcgaat    4620
tttaacaaaa tattaacgtt tacaatttca ggtggcactt ttcggggaaa tgtgcgcgga    4680
acccctattt gtttattttt ctaaatacat tcaaatatgt atccgctcat gagacaataa    4740
ccctgataaa tgcttcaata atattgaaaa aggaagagta tgagtattca acatttccgt    4800
gtcgccctta ttccctttttt tgcggcattt tgccttcctg tttttgctca cccagaaacg    4860
ctggtgaaag taaaagatgc tgaagatcag ttgggtgcac gagtgggtta catcgaactg    4920
gatctcaaca gcggtaagat ccttgagagt tttcgccccg aagaacgttt tccaatgatg    4980
agcacttta aagttctgct atgtggcgcg gtattatccc gtattgacgc cgggcaagag     5040
caactcggtc gccgcataca ctattctcag aatgacttgg ttgagtactc accagtcaca    5100
gaaaagcatc ttacggatgg catgacagta agagaattat gcagtgctgc cataaccatg    5160
agtgataaca ctgcggccaa cttacttctg acaacgatcg gaggaccgaa ggagctaacc    5220
gcttttttgc acaacatggg ggatcatgta actcgccttg atcgttggga accggagctg    5280
aatgaagcca taccaaacga cgagcgtgac accacgatgc ctgtagcaat ggcaacaacg    5340
ttgcgcaaac tattaactgg cgaactactt actctagctt cccggcaaca attaatagac    5400
tggatggagg cggataaagt tgcaggacca cttctgcgct cggcccttcc ggctggctgg    5460
tttattgctg ataaatctgg agccggtgag cgtgggtctc gcggtatcat tgcagcactg    5520
gggccagatg gtaagccctc ccgtatcgta gttatctaca cgacggggag tcaggcaact    5580
atggatgaac gaaatagaca gatcgctgag ataggtgcct cactgattaa gcattggtaa    5640
ctgtcagacc aagtttactc atatatactt tagattgatt taaaacttca ttttttaattt    5700
aaaaggatct aggtgaagat cctttttgat aatctcatga ccaaaatccc ttaacgtgag    5760
ttttcgttcc actgagcgtc agaccccgta gaaaagatca aggatcttc ttgagatcct     5820
ttttttctgc gcgtaatctg ctgcttgcaa acaaaaaaac caccgctacc agcggtggtt    5880
tgtttgccgg atcaagagct accaactctt tttccgaagg taactggctt cagcagagcg    5940
cagataccaa atactgtcct tctagtgtag ccgtagttag gccaccactt caagaactct    6000
gtagcaccgc ctacatacct cgctctgcta atcctgttac cagtggctgc tgccagtggc    6060
gataagtcgt gtcttaccgg gttggactca agacgatagt taccggataa ggcgcagcgg    6120
tcgggctgaa cggggggttc gtgcacacag cccagcttgg agcgaacgac ctacaccgaa    6180
ctgagatacc tacagcgtga gcattgagaa agcgccacgc ttcccgaagg gagaaaggcg    6240
gacaggtatc cggtaagcgg cagggtcgga acaggagagc gcacgaggga gcttccaggg    6300
ggaaacgcct ggtatctta tagtcctgtc gggtttcgcc acctctgact tgagcgtcga    6360
tttttgtgat gctcgtcagg gggcggagc ctatggaaaa acgccagcaa cgcc            6414
```

<210> SEQ ID NO 18
<211> LENGTH: 6062
<212> TYPE: DNA

<213> ORGANISM: Artificial Sequence
<220> FEATURE:
<223> OTHER INFORMATION: Description of Artificial Sequence:plasmid

<400> SEQUENCE: 18

```
tcgacattga ttattgacta gttattaata gtaatcaatt acgggtcat tagttcatag      60
cccatatatg gagttccgcg ttacataact tacggtaaat ggcccgcctg gctgaccgcc    120
caacgacccc cgcccattga cgtcaataat gacgtatgtt cccatagtaa cgccaatagg    180
gactttccat tgacgtcaat gggtggagta tttacggtaa actgcccact tggcagtaca    240
tcaagtgtat catatgccaa gtacgccccc tattgacgtc aatgacggta atggcccgc     300
ctggcattat gcccagtaca tgaccttatg gactttcct acttggcagt acatctacgt     360
attagtcatc gctattacca tggtgatgcg gttttggcag tacatcaatg ggcgtggata    420
gcggtttgac tcacggggat ttccaagtct caccccatt gacgtcaatg ggagtttgtt     480
ttggcaccaa aatcaacggg actttccaaa atgtcgtaac aactccgccc cattgacgca    540
aatgggcggt aggcgtgtac ggtgggaggt ctatataagc agagctcgtt tagtgaaccg    600
tcagatcgcc tggagacgcc atccacgctg ttttgacctc catagaagac accgggaccg    660
atccagcctc cgcggccggg aacggtgcat tggaacgcgg attccccgtg ccaagagtca    720
ggtaagtacc gcctatagag aagactcttg gtttctgat aggcactgac tctctctgcc     780
tattggtcta ttttcccacc cttaggctgc tggtgcttaa ctggcttatc gaaattaata    840
cgactcacta tagggagacc caagcttctg caggtcgaca tcgatggatc cggtacctcg    900
agcgcgaatt ctctagagat atcttgttta ttgcagctta taatggttac aaataaagca    960
atagcatcac aaatttcaca aataaagcat ttttttcact gcattctagt tgtggtttgt   1020
ccaaactcat caatgtatct tatcatgtct ggatcaattc tgaaaaacta gccttaaaga   1080
cagacagctt tgttctagtc agccaggcaa gcatatgtaa ataaagttcc tcagggaact   1140
gaggttaaaa gatgtatcct ggacctgcca gacctggcca ttcacgtaaa cagaagattc   1200
cgcctcaagt tccggttaac aacaggaggc aacgagatct caaatctatt acttctaatc   1260
gggtaattaa aacctttcaa ctaaaacacg gacccacgga tgtcacccac ttttccttcc   1320
ccggctccgc ccttctcagt actccccacc attaggctcg ctactccacc tccacttccg   1380
ggcgcgacac ccacgtgccc tctcccaccc gacgctaacc ccgcccctgc ccgtctgacc   1440
ccgcccacca cctggccccg ccccgttgag gacagaagaa accccgggca gccgcagcca   1500
aggcggacgg gtagacgctg ggggcgctga ggagtcgtcc tctaccttct ctgctggctc   1560
ggtgggggac gcggtggatc tcaggcttcc ggaagactgg aagaaccggc tcagaaccgc   1620
ttgtctccgc ggggcttggg cggcggaaga atggccgcta cgcggact tggtgcgagg    1680
catcgcagga tgcagaagag caagcccgcc gggagcgcgc ggctgtacta ccccgcgcct   1740
ggagcggcca cgccggactg gcggggccg gcctggtgga ggcggagtct gacctcgtgg    1800
aggcggggcc tctgatgttc aaataggatg ctaggcttgt tgaggcgtgg cctccgattc   1860
acaagtggga agcagcgccg ggcgactgca atttcgcgcc aaacttgggg gaagcacagc   1920
gtacaggctg cctaggtgat cgctgctgct gtcatggttc gaccgctgaa ctgcatcgtc   1980
gccgtgtccc agaatatggg catcggcaag aacggagacc ttccctggcc aatgctcagg   2040
tactggctgg attgggttag ggaaaccgag gcggttcgct gaatcgggtc gagcacttgg   2100
cggagacgcg cgggccaact acttagggac agtcatgagg ggtaggcccg ccggctgctg   2160
cccttgccca tgcccgcggt gatccccatg ctgtgccagc ctttgcccag aggcgctcta   2220
```

```
gctgggagca aagtccggtc actgggcagc accacccccc ggacttgcat gggtagccgc    2280
tgagatggag cctgagcaca cgtgacaggg tccctgttaa cgcagtgttt ctctaacttt    2340
caggaacgag ttcaagtact tccaaagaat gaccaccacc tcctcagtgg aaggtaaaca    2400
gaacctggtg attatgggcc ggaaaacctg ttctccatt  cctgagaaga atcgaccttt    2460
aaaggacaga attaatatag ttctcagtag agagctcaag gaaccaccac aaggagctca    2520
ttttcttgcc aaaagtctgg accatgcctt aaaacttatt gaacaaccag agttagcaga    2580
taaagtggac atggtttgga tagttggagg cagttccgtt tacaaggaag ccatgaatca    2640
gccaggccat ctcagactct ttgtgacaag gatcatgcag gaatttgaaa gtgacacgtt    2700
cttcccagaa attgatttgg agaaatataa acttctccca gagtacccag ggtcctttc     2760 tgaagtccag gaggaaaaag gcatcaagta taaatttgaa gtctatgaga agaaaggcta    2820
acagaaagat acttgctgat tgacttcaag ttctactgct ttcctcctaa aattatgcat    2880
ttttacaaga ccatgggact tgtgttggct ttagatcctg tgcatcctgg gcaactgttg    2940
tactctaagc cactccccaa agtcatgccc cagcccctgt ataattctaa acaattagaa    3000
ttattttcat tttcattagt ctaaccaggt tatattaaat atactttaag aaacaccatt    3060
tgccataaag ttctcaatgc ccctcccatg cagcctcaag tggctcccca gcagatgcat    3120
agggtagtgt gtgtacaaga gaccccaaag acatagagcc cctgagagca tgagctgata    3180
tgggggctca tagagatagg agctagatga ataagtacaa agggcagaaa tgggttttaa    3240
ccagcagagc tagaactcag actttaaaga aaattagatc aaagtagaga ctgaattatt    3300
ctgcacatca gactctgagc agagttctgt tcactcagac agaaaatggg taaattgaga    3360
gctggctcca ttgtgctcct tagagatggg agcaggtgga ggattatata aggtctggaa    3420
catttaactt ctccgtttct catcttcagt gagattccaa gggatactac aattctgtgg    3480
aatgtgtgtc agttagggtg tggaaagtcc ccaggctccc cagcaggcag aagtatgcaa    3540
agcatgcatc tcaattagtc agcaaccagg tgtggaaagt ccccaggctc cccagcaggc    3600
agaagtatgc aaagcatgca tctcaattag tcagcaacca tagtcccgcc ctaactccg     3660 cccatcccgc ccctaactcc gcccagttcc gcccattctc cgccccatgg ctgactaatt    3720
ttttttattt atgcagaggc cgaggcgcct ctgagctatt ccagaagtag tgaggaggct    3780
tttttggagg cctaggcttt tgcaaaaaag ctaattcagc ctgaatggcg aatgggaaat    3840
tgtaaacgtt aatattttgt taaaattcgc gttaaatttt tgttaaatca gctcatttt    3900 taaccaatag gccgaaatcg gcaaaatccc ttataaatca aaagaataga ccgagatagg    3960
gttgagtgtt gttccagttt ggaacaagag tccactatta agaacgtgg  actccaacgt    4020 caaagggcga aaaccgtct  atcagggcga tggcccacta cgtgaaccat caccctaatc    4080
aagtttttgg ggtcgaggtg ccgtaaagca ctaaatcgga accctaaagg gagccccga    4140 tttagagctt gacggggaaa gccggcgaac gtggcgagaa aggaagggaa gaaagcgaaa    4200
ggagcgggcg ctagggcgct ggcaagtgta gcggtcacgc tgcgcgtaac caccacaccc    4260
gccgcgctta atgcgccgct acagggcgcg tcaggtggca cttttcgggg aaatgtgcgc    4320 ggaacccta  tttgtttatt tttctaaata cattcaaata tgtatccgct catgagacaa    4380
taaccctgat aaatgcttca ataatattga aaaggaaga gtatgagtat tcaacatttc     4440
cgtgtcgccc ttattccctt ttttgcggca ttttgccttc ctgttttgc  tcacccagaa    4500 acgctggtga aagtaaaaga tgctgaagat cagttgggtg cacgagtggg ttacatcgaa    4560
```

-continued

```
ctggatctca acagcggtaa gatccttgag agttttcgcc ccgaagaacg ttttccaatg    4620
atgagcactt ttaaagttct gctatgtggc gcggtattat cccgtattga cgccgggcaa    4680
gagcaactcg gtcgccgcat acactattct cagaatgact tggttgagta ctcaccagtc    4740
acagaaaagc atcttacgga tggcatgaca gtaagagaat tatgcagtgc tgccataacc    4800
atgagtgata acactgcggc caacttactt ctgacaacga tcggaggacc gaaggagcta    4860
accgcttttt tgcacaacat gggggatcat gtaactcgcc ttgatcgttg ggaaccggag    4920
ctgaatgaag ccataccaaa cgacgagcgt gacaccacga tgcctgtagc aatggcaaca    4980
acgttgcgca aactattaac tggcgaacta cttactctag cttcccggca acaattaata    5040
gactggatgg aggcggataa agttgcagga ccacttctgc gctcggccct tccggctggc    5100
tggtttattg ctgataaatc tggagccggt gagcgtgggt ctcgcggtat cattgcagca    5160
ctggggccag atggtaagcc ctcccgtatc gtagttatct acacgacggg gagtcaggca    5220
actatggatg aacgaaatag acagatcgct gagataggtg cctcactgat taagcattgg    5280
taactgtcag accaagttta ctcatatata ctttagattg atttaaaact tcatttttaa    5340
tttaaaagga tctaggtgaa gatccttttt gataatctca tgaccaaaat cccttaacgt    5400
gagttttcgt tccactgagc gtcagacccc gtagaaaaga tcaaaggatc ttcttgagat    5460 ccttttttc tgcgcgtaat ctgctgcttg caaacaaaaa aaccaccgct accagcggtg    5520
gtttgtttgc cggatcaaga gctaccaact cttttccga aggtaactgg cttcagcaga    5580
gcgcagatac caaatactgt ccttctagtg tagccgtagt taggccacca cttcaagaac    5640
tctgtagcac cgcctacata cctcgctctg ctaatcctgt taccagtggc tgctgccagt    5700
ggcgataagt cgtgtcttac cgggttggac tcaagacgat agttaccgga taaggcgcag    5760
cggtcgggct gaacggggggg ttcgtgcaca cagcccagct tggagcgaac gacctacacc    5820
gaactgagat acctacagcg tgagcattga gaaagcgcca cgcttcccga agggagaaag    5880
gcggacaggt atccggtaag cggcagggtc ggaacaggag agcgcacgag ggagcttcca    5940
gggggaaacg cctggtatct ttatagtcct gtcgggtttc gccacctctg acttgagcgt    6000 cgattttgt gatgctcgtc aggggggcgg agcctatgga aaaacgccag caacgcagct    6060
gc                                                                   6062
```